(12) United States Patent
Carter et al.

(10) Patent No.: US 7,422,693 B2
(45) Date of Patent: Sep. 9, 2008

(54) MONITORING AND CONTROL SYSTEM FOR BLOOD PROCESSING

(75) Inventors: Lee F. Carter, Lakewood, CO (US); Jeremy P. Kolenbrander, Brighton, CO (US); James R. Ladtkow, Broomfield, CO (US); Joseph A. Scibona, Littleton, CO (US); Jeffrey A. Steward, Lakewood, CO (US); Chris Fletcher, Superior, CO (US)

(73) Assignee: Caridianbct, Inc., Lakewood, CO (US)

( * ) Notice: Subject to any disclaimer, the term of this patent is extended or adjusted under 35 U.S.C. 154(b) by 419 days.

(21) Appl. No.: 10/884,877

(22) Filed: Jul. 1, 2004

(65) Prior Publication Data
US 2005/0051466 A1 Mar. 10, 2005

Related U.S. Application Data

(60) Provisional application No. 60/485,015, filed on Jul. 2, 2003.

(51) Int. Cl.
*B04B 9/10* (2006.01)
(52) U.S. Cl. ............... 210/745; 210/94; 210/512.1; 210/787; 250/573; 250/574; 494/1; 494/7; 494/10; 494/37
(58) Field of Classification Search .......... 210/94, 210/96.1, 512.1, 745, 787, 739; 494/1, 10, 494/11, 37, 7; 422/72, 82.05; 436/164, 177; 356/39, 552, 553; 250/573–576; 73/61.48
See application file for complete search history.

(56) References Cited

U.S. PATENT DOCUMENTS 4,151,844 A 5/1979 Cullis et al.

(Continued)

FOREIGN PATENT DOCUMENTS

DE 3301113 A1 7/1983

(Continued)

OTHER PUBLICATIONS

Salgaller, Michael L. (2003) "A Manifesto on the Current State of Dendritic Cells in Adoptive Immunotherapy," *Transfusion* 43(4):422-424.

(Continued)

*Primary Examiner*—Joseph W Drodge
(74) *Attorney, Agent, or Firm*—Greenlee, Winner and Sullivan, P.C.

(57) ABSTRACT

The invention relates generally to methods of monitoring and controlling the processing of blood and blood samples, particularly the separation of blood and blood samples into its components. In one aspect, the invention relates to optical methods, devices and device components for measuring two-dimensional distributions of transmitted light intensities, scattered light intensities or both from a separation chamber of a density centrifuge. In embodiment, two-dimensional distributions of transmitted light intensities, scattered light intensities or both measured by the methods of the present invention comprise images of a separation chamber or component thereof, such as an optical cell of a separation chamber. In another aspect, the present invention relates to multi-functional monitoring and control systems for blood processing, particularly blood processing via density centrifugation. Feedback control systems are provided wherein two-dimensional distributions of transmitted light intensities, scattered light intensities or both are measured, processed in real time and are used as the basis of output signals for controlling blood processing. In another aspect, optical cells and methods of using optical cells for monitoring and control blood processing are provided.

86 Claims, 29 Drawing Sheets

U.S. PATENT DOCUMENTS

| | | | |
|---|---|---|---|
| 4,493,691 A | | 1/1985 | Calari |
| 4,557,719 A | | 12/1985 | Neumann et al. |
| 4,567,373 A | * | 1/1986 | O'Meara et al. ............ 250/573 |
| 4,670,002 A | | 6/1987 | Koreeda et al. |
| 4,671,102 A | * | 6/1987 | Vinegar et al. ............ 73/61.48 |
| 4,724,317 A | | 2/1988 | Brown et al. |
| 4,834,890 A | | 5/1989 | Brown et al. |
| 5,076,911 A | | 12/1991 | Brown et al. |
| 5,104,526 A | | 4/1992 | Brown et al. |
| 5,260,598 A | | 11/1993 | Brass et al. |
| 5,316,667 A | | 5/1994 | Brown et al. |
| 5,322,620 A | | 6/1994 | Brown et al. |
| 5,653,887 A | | 8/1997 | Wahl et al. |
| 5,948,271 A | * | 9/1999 | Wardwell et al. ........... 210/739 |
| 6,053,856 A | | 4/2000 | Hlavinka |
| 6,254,784 B1 | * | 7/2001 | Nayak et al. ............... 210/745 |
| 6,334,842 B1 | | 1/2002 | Hlavinka et al. |
| 6,338,820 B1 | * | 1/2002 | Hubbard et al. ............... 422/64 |
| 6,354,986 B1 | * | 3/2002 | Hlavinka et al. .............. 494/37 |
| 6,514,189 B1 | | 2/2003 | Hlavinka et al. |
| 6,632,399 B1 | * | 10/2003 | Kellogg et al. ................ 422/72 |
| 6,790,371 B2 | | 9/2004 | Dolecek |
| 2002/0147094 A1 | | 10/2002 | Dolecek |

FOREIGN PATENT DOCUMENTS

| | | |
|---|---|---|
| DE | 3413065 A1 | 10/1984 |
| DE | 3301113 C2 | 1/1985 |
| EP | 0 392 475 A2 | 10/1990 |
| EP | 0 729 790 A2 | 9/1996 |
| EP | 0 729 790 B1 | 5/2001 |
| WO | WO 96/39618 | 5/1996 |

OTHER PUBLICATIONS

International Search Report for PCT/US2004/021344 mailed Nov. 17, 2004.

* cited by examiner

MONITORING AND CONTROL SYSTEM FOR BLOOD PROCESSING

CROSS-REFERENCE TO RELATED APPLICATIONS

This application claims priority under 35 U.S.C. 119(e) to provisional patent application 60/485,015, filed Jul. 2, 2003, which is hereby incorporated by reference in its entirety to the extent not inconsistent with the disclosure herein.

BACKGROUND OF INVENTION

Large scale blood collection and processing play important roles in the worldwide health care system. In conventional large scale blood collection, blood is removed from a donor or patient, separated into its various blood components via centrifugation, filtration and/or elutriation and stored in sterile containers for future infusion into a patient for therapeutic use. The separated blood components typically include fractions corresponding to red blood cells, white blood cells, platelets and plasma. Separation of blood into its components can be performed continuously during collection or can be performed subsequent to collection in batches, particularly with respect to the processing of whole blood samples. Separation of blood into its various components under highly sterile conditions is critical to most therapeutic applications.

Recently, apheresis blood collection techniques have been adopted in many large scale blood collection centers wherein a selected component of blood is collected and the balance of the blood is returned to the donor during collection. In apheresis, blood is removed from a donor and immediately separated into its components by on-line blood processing methods. Typically, on-line blood processing is provided by density centrifugation, filtration and/or diffusion-based separation techniques. One or more of the separated blood components are collected and stored in sterile containers, while the remaining blood components are directly re-circulated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once every fourteen days.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation. Alternatively, apheresis techniques may be used to perform red blood cell exchange for patients with hematological disorders such as sickle cell anemia and thalassemia, whereby a patient's red blood cell component is removed and donated packed red blood cells are provided to the patient along with his remaining blood components. Further, apheresis may be used to perform therapeutic platelet depletion for patients having thrombocytosis and therapeutic plasma exchange for patients with autoimmune diseases.

Both conventional blood collection and apheresis systems typically employ differential centrifugation methods for separating blood into its various blood components. In differential centrifugation, blood is circulated through a sterile separation chamber which is rotated at high rotational speeds about a central rotation axis. Rotation of the separation chamber creates a centrifugal force directed along rotating axes of separation oriented perpendicular to the central rotation axis of the centrifuge. The centrifugal force generated upon rotation separates particles suspended in the blood sample into discrete fractions having different densities. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887 and U.S. patent application Ser. No. 10/413,890.

To achieve continuous, high throughput blood separation, extraction or collect ports are provided in most separation chambers. Extraction ports are capable of withdrawing material from the separation chamber at adjustable flow rates and, typically, are disposed at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase. For example, if the fraction containing white blood cells resides too close to the extraction port corresponding to platelet enriched plasma, white blood cells may enter the platelet enriched plasma stream exiting the separation chamber, thereby degrading the extent of separation achieved during blood processing. Although conventional blood processing via density centrifugation is capable of efficient separation of individual blood components, the purities of individual components obtained using this method is often not optimal for use in many therapeutic applications. For example, centrifugation separation of blood samples is unable to consistently (99% of the time) produce separated platelet components which have less than $1 \times 10^6$ white blood cells per every $3 \times 10^{11}$ platelets collected. The presence of white blood cells in platelet products increases the risks of viral exposure and immunological complications upon infusion into a patient.

As a result of the inability to achieve optimal purity levels using centrifugation separation alone, a number of complementary separation techniques based on filtration, elutriation and affinity-based techniques have been developed to achieve the optimal purities needed for use of blood components as therapeutic agents. These techniques, however, often reduce the overall yield realized and may reduce the therapeutic efficacy of the blood components collected. Exemplary methods and devices of blood processing via filtration, elutriation and affinity based methods are described in U.S. Pat. No. 6,334,842 and International Patent Application Serial No. PCT/US03/117764.

The purity of extracted blood components using density centrifugation is currently limited by the control of the position of phase boundary layers between separated components provided by conventional centrifugation devices and methods. The position of phase boundaries along the separation axis depends on a number of variables. First, phase boundary positions depend on the relative flow rates of individual blood components out of the separation chamber. Second, phase boundary positions depend on the rotational velocity of the separation chamber about the central rotation axis and the temperature of the blood undergoing separation. Third, phase boundary positions vary with the composition of the blood undergoing processing. Blood sample composition may vary considerably from donor to donor and/or from patient to patient. In addition, blood composition may vary significantly as function of time for a given donor or patient, especially as blood is recycled through the separation chamber multiple times. Given the sensitivity of the phase boundary position to many variables which change from person to person and during processing, it is important to monitor the position of the phase boundaries during blood processing to ensure optimal separation conditions are maintained and the desired purity of selected blood components is achieved. In addition, accurate characterization of the positions of phase boundaries allows for separation conditions to be adjusted and optimized for changes in blood composition during processing.

Although capable of measuring the position of one or more phase boundaries, conventional optical monitoring and control methods for blood processing have substantial limitations. First, conventional optical monitoring systems and methods, such as those discussed in U.S. Pat. Nos. 5,316,667 and 5,260,598, utilize one-dimensional optical detection or one-dimensional optical scanning. Accordingly, these methods are unable to characterize the intensities of transmitted and/or scattered light from a two-dimensional or three-dimensional region of a blood processing device. Moreover, these methods are unable to measure the flux or purities of cellular material exiting the separation chamber through a selected extraction port. Second, conventional optical monitoring methods lack the signal-to-noise ratios needed for many blood processing applications because light intensities characterized are limited to a single optical axis. For example, conventional optical monitoring methods lack the sensitivity needed to accurately resolve the position of the phase boundaries between white blood cells and other blood components because white blood cells comprise less than 1% of total blood volume. Therefore, these methods are not capable of providing blood components, such as platelets and red blood cells, with white blood cell levels reduced to the extent needed to avoid immunological complications and viral transmission. Third, conventional optical monitoring methods are limited to fixed optical geometries and are incapable of monitoring regions of the density centrifuge device located on a plurality of different optical axes. As a result, the functional capabilities of conventional optical methods for monitoring and controlling separation by density centrifugation are substantially limited to monitoring the position of phase boundaries in the separation chamber.

It will be appreciated from the foregoing that a need exists for methods and devices for monitoring and controlling the processing of whole blood samples and blood component samples. Particularly, optical monitoring methods and devices are needed which are capable of accurately characterizing the separation, extraction and collection of blood components processed by density centrifugation. In addition, multifunctional optical monitoring and control systems for blood processing are needed which are capable of simultaneously monitoring a plurality of regions corresponding to a separation region, sample identification region and a blood component extraction region. Accordingly, it is an object of the present invention to provide methods, devices and device components for blood processing which are capable of high throughput separation, characterization and collection of individual blood components, particularly red blood cells, white blood cells, platelet enriched plasma and plasma.

SUMMARY OF THE INVENTION

This invention provides methods, devices and device components for improving the processing of fluids comprising fluid components, such as blood, components of blood and fluids derived from blood. Methods, devices and device components of the present invention are capable of monitoring and controlling separation of blood into discrete components and subsequent collection of selected components. The present invention includes methods, devices and device components for optically monitoring blood processing via a wide range of separation techniques, including density centrifugation, centrifugal elutriation, size and shape filtration, affinity chromatography or any combination of these techniques. The methods, devices and device components of the present invention are capable of characterizing the composition and purity of a collected blood component and capable of measuring the rate in which a blood component is extracted and collected. In addition, the methods, devices and device components of the present invention are capable of controlling blood processing by optimizing separation and extraction conditions to reproducibly achieve a desired selected purity and/or composition of a blood component. The present invention improves processing of static blood samples or flowing blood samples.

In one aspect, this invention provides methods, devices and device components for improving the separation of whole blood via density centrifugation and subsequent collection of selected, separated blood components. Particularly, the invention relates to optical methods, devices and device components for measuring two-dimensional distributions of light intensities corresponding to light transmitted and/or scattered by separated blood components in a rotating separation chamber, particularly a separation chamber having an optical cell with one or more extraction ports. In one embodiment, two-dimensional distributions of light intensities measured by the present invention comprise two- or three-dimensional images of device components of a density centrifuge systems, such as a separation chamber, an optical cell and/or one or more extraction ports, and materials disposed therein. The measured two-dimensional distributions of light intensities comprising images of device components of a density centrifuge provide quantitative information relating to important optimizing operating conditions of the centrifugation device. First, two-dimensional distributions of light intensities measured by the present invention provide an in situ and real time measurement of the position of one or more phase boundaries between optically differentiable blood components undergoing separation. Second, measured two-dimensional distributions of transmitted and/or scattered light intensities provide an in situ and real time measurement of the composition of one or more separated blood components such as separated blood components exiting an extraction port of an optical cell. Third, measured two-dimensional distributions of transmitted and/or scattered light intensities provide an in situ and real time measurement of the flux of cellular blood components exiting the separation chamber through one or more extraction ports of an optical cell. Fourth, measured two-dimensional distributions of transmitted and/or scattered light intensities provide a means of sensing identity information, such as identification number and/or lot identification number corresponding to a blood sample undergoing processing and the kit or container holding the blood sample. Automated sample and lot identification is beneficial because this information can be used to confirm that the appropriate blood processing procedure is selected and carried out for a given sample. Finally, measured two-dimensional distributions of transmitted and/or scattered light intensities provide a means of monitoring the alignment of the separation chamber in a blood processing device and identifying leakage of fluid out of the separation chamber.

In one aspect, the present invention relates to multifunctional optical monitoring systems for a blood processing device, particularly a density centrifuge. An optical monitoring system is provided which is capable of measuring a two dimensional distribution of transmitted and/or scattered light intensities corresponding to patterns of light transmitted and/or scattered from an observation region positioned on a density centrifuge, such as an observation region corresponding to an optical cell of a separation chamber. In an embodiment, a dynamic optical monitoring system of the present invention is capable of measuring a two-dimensional distribution of scattered any/or transmitted light comprising an image of an observation region having a position which is selectively adjustable before, during and/or after processing. Alternatively, the optical monitoring system of the present invention is capable of measuring a two-dimensional distribution of scattered any/or transmitted light corresponding to an observation region having a selectively adjustable size. Alternatively, the present invention includes optical monitoring systems having a selected, fixed position observation region. Use of a fixed position observation region provides highly stable monitoring systems capable of generating very reproducible images. Monitoring systems of the present invention are capable of monitoring the position of boundary layers between optically differentiable components, identifying and tracking a blood sample undergoing processing, detecting leaks and misalignment of the separation chamber, monitoring the composition of extracted blood components, monitoring the composition of a blood sample prior to processing, regulating the administration of anti-coagulation agents or other blood treatment agents added to the blood sample and characterizing the flux of cellular blood components extracted from the centrifuge.

In another aspect, the present invention relates to multifunctional control systems for a blood processing device, particularly a density centrifuge. Feedback control systems are provided wherein two-dimensional distributions of transmitted and/or scattered light intensities corresponding to patterns of light originating from an observation region on a separation chamber are generated and processed, preferably in real time. The two-dimensional distributions of transmitted and/or scattered light intensities acquired serve as the basis for control signals transmitted to various components of a density centrifuge. These control signals can be used to selectively adjust the separation conditions of the blood sample undergoing processing, such as the position of phase boundaries between optically differentiable components, and the composition, purities and flow rates of separated components out of the density centrifuge. In a preferred embodiment, images of the separation chamber identifying the positions of phase boundaries between separated blood components are used to select flow rates of these components out of the separation chamber. In this embodiment, flow rates can be selected to provide and maintain a desired extent of separation during processing and extraction. In another exemplary embodiment, two-dimensional distributions of transmitted and/or scattered light intensities comprising images of one or more extraction ports are acquired and processed in real time to determine the composition and/or fluxes of cellular material exiting the separation chamber via extraction ports. In this embodiment, fluxes of separated components can be utilized to select the processing times and flow rates needed to collect a selected amount of a particular blood component or can be utilized to determine the return rate of a selected blood component to a donor or patient in apheresis blood processing. In another embodiment, flow rates of blood components are selectively adjusted to select a desired composition and/or purity of an extracted blood component An exemplary optical monitoring system for a density centrifuge having a separation chamber rotating about a central rotation axis comprises at least one light source, a light collection element and a two-dimensional detector. Rotation of the separation chamber about a central rotation axis results in separation of the blood components in the separation chamber according to density along rotating separation axes oriented perpendicular to the central rotation axis of the centrifuge. Both the light source and light collection element are arranged such that they are periodically in optical communication with an observation region positioned on the density centrifuge. In one embodiment, the light source and two dimensional detector are arranged such that an optical cell of the separation chamber is periodically rotated into and out of the observation region. The light source is capable of providing an incident light beam which illuminates at least a portion of the density centrifuge, preferably an optical cell of the rotating separation chamber, thereby generating light which is transmitted, scattered, or both, by blood components undergoing separation. Preferred light sources are capable of generating an incident light beam comprising light having a selected wavelength range including, but not limited to, visible light, infrared light and/or ultraviolet light. In one embodiment, a plurality of light sources are provided capable of illuminating a plurality of sides of an optical cell of a separation chamber.

The light collection element is capable of collecting light from an observation region. In one embodiment, collected light from the observation region corresponds to light which is transmitted and/or scattered by blood components undergoing separation, light which is transmitted and/or scattered by components of the centrifugation device, such as the separation chamber, or both. The light collection element directs the collected light onto the two-dimensional detector. The two-dimensional detector detects the light received from the light collection element and measures a two-dimensional distribution of transmitted and/or scattered light intensities corresponding to patterns of transmitted and/or scattered light. In one embodiment, the light collection element and two-dimensional detector are arranged such that the relative spatial distribution of scattered and/or transmitted light from the observation region is preserved during collection and detection. In a preferred embodiment, the two-dimensional detector is also capable of generating one or more output signals corresponding to the two-dimensional distribution of transmitted and/or scattered light intensities from the observation region. In one embodiment, the output signal is transmitted to a device, such as a computer, capable of displaying the two-dimensional distribution of intensities, storing the two-dimensional distribution of intensities and/or processing the two-dimensional distribution of intensities. Alternatively, the output signal is transmitted to a device, such as a computer, capable of controlling operating settings of the density centrifuge. In a preferred embodiment, the output signal is sent to a device controller which ascertains a number of important operating parameters from the two-dimensional distribution of intensities acquired. Device controllers of the present invention are capable of determining the position of phase boundaries between optically differentiable blood components, the fluxes of cellular materials and noncellular materials out of the separation chamber, the composition of extracted blood components, hematocrit, and the extent of hemolysis in a blood sample. In one embodiment, the device controller is also capable of quantifying in real time the uncertainty in operating parameters ascertained from two-dimensional distribution of scattered and/or transmitted light intensities.

In an embodiment having a dynamic observation region, the position of the observation region on the blood processing device is selectively adjustable. In an exemplary embodiment, the position of the observation region is adjusted by varying the position and/or field of view of the light collection element. For example, in one embodiment the light collection element and two-dimensional detector are arranged such that they are selectively positionable along a detection axis positioned orthogonal to the central rotation axis. In this embodiment, translation of the light collection element and two-dimensional detector along the detection axis allows selective adjustment of the position of the observation region along a separation axis of the centrifugation device. In an alternative embodiment, the size of the observation region is selectively adjustable, for example by adjusting the length, width, or radius of the observation region or any combination of these. For example, the size of the observation region can be adjusted by varying the field of view of one or more lenses or lens systems comprising the light collection element. In an embodiment, the ability to selectively adjust the position, size, or both, of the observation region before, during and after processing provides multifunctional optical monitoring systems capable of observing and controlling a plurality of important device operating conditions.

In another aspect, the present invention comprises an optical monitoring and control system capable of measuring the position of phase boundaries between optically differentiable blood components. In this embodiment, the observation region is positioned such that phase boundaries between optically differentiable components are viewable, for example once per rotation of the centrifuge. For example, in an embodiment, an interface area is periodically rotated into the observation region upon rotation of the separation chamber. Reference to an interface region in the present invention refers to an area of the separation chamber wherein two or more separated phases are viewable. Exemplary interface regions refer to a region of the separation chamber having one or more windows for transmitting light through the separated blood components, such as an optical cell. For example, in a preferred embodiment, the interface area is defined by an optical cell wherein the phase boundaries between optically differentiable blood components are viewable, such as the phase boundary between red blood cells and the buffy coat layer and the phase boundary between the buffy coat layer and the plasma. In an exemplary, phase boundaries within a mixed-phase layer, such as the buffy coat layer, are viewable. For example, the present invention provides a means of monitoring the phase boundary between a white blood cell-containing layer and a platelet enriched plasma layer.

In a preferred embodiment, illumination of the separation chamber generates patterns of light transmitted and/or scattered from separated blood fractions in the interface region. Optically differentiable blood components generate different intensities of transmitted or scattered light. Therefore, detection of patterns of transmitted light, scattered light, or both, corresponding to an observation region provides a direct measurement of the positions of phase boundaries along the separation axis of a density centrifuge. In a preferred embodiment optically differentiable components have transmitted and/or scattered light intensities that differ by about 30 relative intensity units, wherein a relative intensity unit reflects a range of 0-255 intensity units and a value of 0 corresponds to no detected light and a value of 255 corresponds to an intensity which saturates the detector. In an exemplary embodiment, at least one calibration marker is provided in the observation region. Calibration markers of the present invention have well known optical properties, such as absorption coefficients, scattering cross sections, lengths and widths, and provide spatial reference points for resolving the positions of optically differentiable blood components along the separation axis. Calibration markers also provide a reference for optimizing focusing of the light collection element and providing a brightness and/or color index to calibrate measured light intensities.

Measurement of a two-dimensional distribution of scattered and/or transmitted light intensities in the present invention is beneficial because it provides a sensitive measurement of the position of one or more phase boundaries along the separation axis. For example, acquisition of a two-dimensional distribution of scattered and/or transmitted light intensities from a 0.2-0.4 inches$^2$ observation region provides a measurement of the position of a phase boundary accurate to within about 0.0005±0.0002 inch$^2$.

In another preferred embodiment, the present invention comprises an optical monitoring system capable of providing in situ measurements of the composition of one or more blood component undergoing processing in a density centrifuge, such as an extracted blood component. Reference to composition in this context relates to the amount, identity and purity of cellular materials, such as erythrocytes, leukocytes and thrombocytes, and non-cellular materials, such as blood plasma proteins, in a given blood component, such as an extracted component. Measurement of the composition of a selected blood component includes, but is not limited to, measurement of cell types and concentration, and purity of a given separated fraction or mixed fraction. Composition measurements can be used to predict yield and quality. Exemplary composition measurements are also be the basis of control signals for optimizing separation and extraction conditions to achieve desired compositions of one or more extracted components. In an embodiment of the present invention, the observation region is positioned such that at least one separated blood component is viewable. For example, in one embodiment a composition-monitoring region is periodically rotated into the observation region as the separation chamber is rotated about the central rotation axis. Reference to a composition-monitoring region in the present invention relates to a portion of the separation chamber occupied by at least one separated component, such as an extraction port of an optical cell of a separation chamber. In one embodiment, the separation chamber is arranged such that upon illumination, light is transmitted through at least one separated component to provide a measurement of composition. Transmitted light is collected by the light collection element and detected by the two-dimensional detector. In one embodiment, the observation region is positioned to provide a continuous measurement of composition along the separation axis. Alternatively, light collection element and detector are positioned such that one or more extraction port is periodically rotated into the observation region as the centrifuge rotates. Use of two-dimensional optical imaging allows for the accurate characterization of sample composition along a plurality of separation axes which allows for desirable signal-to-noise ratio averaging that enhances sensitivity.

The intensity of light transmitted by blood or a blood component depends on the concentrations and optical properties of cellular and noncellular components and the optical path length of light through the separation chamber. Accordingly, measurement of a pattern of light intensities transmitted through the separation chamber provides a plurality of measurements of the composition of a selected blood component. Measurement of a two-dimensional distribution of scattered and/or transmitted light intensities in the present invention is beneficial because it provides a method of measuring the purity and/or flux of an extracted, separated fraction, in contrast to conventional one-dimensional optical detection or scanning methods.

In another aspect, the present invention comprises an optical monitoring system capable of measuring the flux and/or composition of one or more cellular blood components exiting an extraction port of the separation chamber, such as an extraction port of an optical cell. In this embodiment, the observation region is positioned on the density centrifuge such that at least one extraction port of the separation chamber is viewable. For example, in one embodiment, at least one extraction port is periodically rotated into the observation region as the separation chamber is rotated about the central rotation axis. In a preferred embodiment, the separation chamber is illuminated in a manner such that light is transmitted through at least one extraction port. As cellular components pass through an extraction port, light is absorbed and/or scattered by a given component. By monitoring the two-dimensional distribution and temporal profile of transmitted and/or scattered light intensities, cellular matter exiting the separation chamber are able to be quantified and type-characterized as a function of time. In an embodiment, the observation region of the present invention is positioned such that a two-dimensional distribution of scattered and/or transmitted light intensities is acquired showing the passage of cellular and non-cellular materials out of the separation chamber, preferably for some applications showing the passage of cellular and non-cellular materials out of an optical cell of a separation chamber. As cellular material absorbs and/or scatters incident light, the flux of cellular material passing through a selected extraction port is determined by measuring the transmitted light area intensity as a function of time. In some instances, for example, larger transmitted and/or scattered light intensities correspond to larger concentrations of cellular material than smaller transmitted and/or scattered light intensities. The present invention includes embodiments wherein at least a portion of the observation region is positioned such that extraction ports in contact with separated fractions corresponding to red blood cells, white cells, platelet enriched plasma and/or plasma are periodically rotated into the observation region.

In another aspect, the present invention comprises an optical monitoring system capable of monitoring the composition of a blood sample prior to blood processing. For example, optical monitoring systems of the present invention generate a two-dimensional distribution of scattered and/or transmitted intensities of light from one or more inlets of a blood processing devise, such as the inlets of a density centrifuge. The levels of light transmitted and/or scattered by a blood sample flowing through the inlet provides real time measurements of important qualities of the incoming blood sample, such as the extent of hemolysis in the blood sample, hematocrit, abundance of lipids in the blood sample and other measurements of blood sample composition. A benefit of this aspect of the invention is that measurements of the composition of a blood sample prior to processing correlates to blood sample and blood component composition measurements taken during and after blood processing to provide a better understanding of a selected blood processing procedure or therapy.

The present invention includes embodiments wherein a plurality of centrifuge operating parameters is measured and analyzed upon acquisition of every two-dimensional distribution of scattered and/or transmitted light intensities. In an embodiment, for example, the present invention comprises an optical monitoring system capable of simultaneously determining the position of at least one phase boundary between at least two optically differentiable blood components, the composition of at least one separated blood component and the flux and/or composition of one or more cellular blood components exiting an extraction port of the separation chamber. In this embodiment, the observation region is positioned on the density centrifuge such that phase boundaries between optically differentiable components, one or more separated components, one or more inlets and at least one extraction port are each viewable upon rotation of the separation chamber about the central rotation axis. An exemplary separation chamber, for example, is designed such that phase boundaries, extraction ports, inlet ports and separated components are readily observable in an image provided by a single two-dimensional distribution of scattered and/or transmitted intensities of light from the separation chamber. This functional aspect of the present invention provides simultaneous monitoring of a plurality of operating conditions of a blood system, which allow correlations between two or more operating parameter to be analyzed and used for accurate device control. Further, methods of the present invention include device control methods wherein a blood processing system is controlled using output signals corresponding to real time measurements of a plurality of operating conditions of a density centrifuge. This functional capability provides improved device control with respect to the control provided by conventional one dimensional scanning or imaging techniques.

Observation regions of the present invention also includes regions other than those selected for viewing separated blood components in the separation chamber. In one embodiment, the observation region includes an identifying region of the blood sample, such as a bar code or other sample designation. This embodiment allows efficient identification and tracking of processed blood products. Alternatively, the observation region includes a region for detecting leaks of blood in the density centrifuge device or an alignment region for detecting improper or proper alignment of the separation chamber before, during or after blood processing. In addition, the present invention can detect spillover of one blood component into the collection port of another blood component. In this context, spillover refers to processes whereby the position of a separated layer in separation chamber changes such that the separated layer contact the orifice of an extraction port corresponding to different separated component.

In another aspect, the present invention comprises a control system for a density centrifuge device. In this embodiment, the optical monitoring system of the present invention is operationally coupled to one or more centrifugation device controllers. In an embodiment, centrifuge device controllers of the present invention receive an output signal from the two-dimensional detector, process the output signal in real time and adjust operating conditions of said centrifugation device to achieve a desired extent of separation and a desired composition of an extracted blood component. In another embodiment comprising a feedback device controller, the device controller and optical monitoring system are operationally coupled in a manner whereby an output signal corresponding to a two-dimensional distribution of scattered and/or transmitted intensities of light from an interface region including one or more phase boundaries and/or one or more extraction ports is sent to a controller capable of adjusting the flow rate of one or more separated blood components out of the separation chamber. In this embodiment, the controller adjusts the flow rates of individual blood components in a manner to selectively adjust the positions of one or more phase boundaries along the separation axis such that a selected extraction port is in fluid communication with a single blood component. Similarly, the present invention includes feedback device controllers, wherein output signals corresponding to a two-dimensional distribution of scattered and/or transmitted light intensities from light from one or more extraction port is sent to a controller capable of adjusting the flow rate of one or more separated blood components from the separation chamber. In this embodiment, the controller adjusts the flow rates of individual blood components in a manner to achieve desired compositions of extracted blood fractions.

In another aspect, the present invention is capable of measuring a two-dimensional distribution of scattered and/or transmitted light intensities comprising a three dimensional image of a region of the separation chamber occupied by one or more blood components, such as a region of an extraction port. In this embodiment, light produced upon illumination of an observation region is collected and detected. In one embodiment, a three dimensional image is generated statistically by modeling the scattering of light by cellular components located in different layers in the region of the separation chamber monitored. Generating a three dimensional image is beneficial because it provides a measurement of the composition of separated blood components along a third axis corresponding to the depth in the separation chamber. This measurement is useful for characterizing the flows of different blood components into the separation chamber and/or through exit ports disposed at different separation chamber depths. In an alternative embodiment, the present invention is capable of measuring a two dimensional distribution of light intensities from fluorescent materials present in the separation chamber. This aspect of the present invention is capable of generating two or three dimensional images from the acquired two-dimensional distributions of fluorescent light intensities. In this embodiment, fluorescence is excited by illumination with an excitation beam. The fluorescence generated is then collected and detected in a manner generating two-dimensional or three-dimensional images. This embodiment is especially useful for monitoring and controlling the separation of fluorescently labeled materials, such as fluorescently labeled cells or blood proteins.

In another embodiment, the present invention provides control systems for centrifuge blood processing of batch samples of blood, preferably whole blood samples or blood samples comprising one or more blood components contained in containers or bags. Exemplary methods and devices for processing batch samples are described in U.S. application Ser. No. 10/413,890. In one embodiment, one or more blood samples residing in an initial fluid containment container are connected to the rotors of a density centrifuge in a manner allowing rotation of the blood samples about a central rotation axis. Rotation of the centrifuge generates a centrifugal force which separates components of the sample according to density along rotating separation axes oriented orthogonal to the central rotation axis. Once the blood sample undergoes separation, discrete components are sequentially extracted out of the initial fluid containment container via one or more outlet ports operationally connected to a plurality of physically separated fluid-receiving containers. Discrete components are extracted via pumping or by the introduction of an inert fluid which is capable of forcing the fractionated sample to exit the fluid containment container. In a preferred embodiment, the present invention provides a means of monitoring and controlling the flow rates and the fluid paths of blood components to selected fluid-receiving containers corresponding to extracted components.

In one embodiment, the optical monitoring and control systems of the present invention is operationally coupled to a batch sample centrifuge in a manner such that phase boundaries between optically differentiable materials, purity and composition of extracted components and the flux of extracted components is monitored during processing in real time. Further, the present invention provides a means of controlling the withdrawal of separated blood components such that the discrete fractions can be separately collected in separate fluid-receiving containers. For example, two-dimensional distributions of scattered and/or transmitted light intensities comprising images of the rotating initial fluid containment container is used to select pumping rates out of the initial fluid containment container or inert fluid flow rates into the fluid containment container in a manner ensuring that only a selected component is directed to a selected fluid-receiving container. In a preferred embodiment, the monitoring system of the present invention is capable of monitoring the change in container of a given component as it is extracted by measuring two-dimensional distributions of scattered and/or transmitted light intensities of light from the separation chamber corresponding to phase boundaries between optically differentiable components or corresponding to one or more extraction ports. A optical monitoring and control system of the present invention is also capable of switching the fluid-receiving container in fluid communication with the initial fluid containment container upon substantially complete extraction of a selected component. Alternatively, an optical monitoring and control system of the present invention is capable of adjusting the pumping rate of a component being extracted to ensure that an adjacent component is not collected in the same fluid-receiving container. In a preferred embodiment, the optical monitoring and control system of the present invention is capable of generating an output signal triggering a multi-channel valve or clamp to divert the flow of sample corresponding to an adjacent component into separate fluid-receiving container.

Collection and processing two-dimensional distributions of scattered and/or transmitted light intensities corresponding to an image of an observation region have a number of advantages over conventional one-dimensional optical monitoring or scanning methods applied to centrifugation of blood samples. First, two-dimensional distributions of scattered and/or transmitted light intensities comprising images of an observation region provide a substantially improved means for discriminating between optically differentiable blood components and measuring the position of phase boundaries between these components as compared to one-dimensional measurements. One-dimensional optical scanning or monitoring provides a single profile of light intensities corresponding to a single optical axis. In contrast, two-dimensional distributions of scattered and/or transmitted light intensities provided by the present invention comprise a pattern of light intensities corresponding to a plurality of optical axes. Therefore, each two-dimensional distribution of scattered and/or transmitted light intensities provides a plurality of multiple measurements of the positions of phase boundaries along the separation axes. Averaging light intensities from each optical axis monitored improves signal-to-noise ratios over measurements derived from one-dimensional measurements by a factor of approximately 10. The improvement in signal-to-noise ratio observed in the present invention provides more reproducible measurements of the relative positions of phase boundaries and provides more accurate calibration of absolute phase boundary positions. In addition, the improved signal-to-noise ratio provides the present systems the capability of providing direct measurements of the composition and purity of any portion of a blood sample, particularly the composition and purity of a given separate blood component, in contrast to conventional one-dimensional scanning and imaging methods.

Second, measurement of light intensities over a two-dimensional area reduces problems arising from heterogeneity in the separated blood components. The various cellular components of blood exhibit distributions of cell types, sizes, shapes and optical properties, such as absorption constants and scattering coefficients. As a result, profiles of scattered and/or transmitted light intensities at different points along the separation axes show a substantial degree of variability for different regions of the separation chamber. Collecting light associated with a plurality of optical axes allows the effects of heterogeneity in the various cellular components to be treated statistically. In one aspect of the present invention, each two-dimensional distribution of scattered and/or transmitted light intensities is statistically analyzed to provide a measure of the average optical properties of a given blood component. Further, the devices and methods of the present invention provide a quantitative measurement of the uncertainties associated with compositions of blood components disposed along the separation chamber, which allows accurate characterization of the reproducibility in the purity levels of extracted components achieved. The ability to characterize uncertainty in the purity levels achieved allows for the quantitative assessment of quality assurance useful for establishing regulatory approval. Third, collection and detection of scattered light corresponding to a two-dimensional area allows for direct measurements of the composition and flux of cellular materials out of an extraction port of a separation chamber. Cellular components of blood undergoing separation are extracted from a separation chamber via extraction ports, which comprise tubes extending selected distances along the separation axis. The flux of cellular components through the extraction port is not spatially uniform.

Rather, the flow of cellular components routinely exhibits substantial spatial inhomogeniety. Therefore, to accurately measure the flux of cellular material exiting the separation chamber at a given time, a profile of transmitted light intensities across an area perpendicular to the flow of exiting cellular components is required. Two-dimensional distributions of scattered and/or transmitted light intensities provide measurements corresponding to a plurality of axes perpendicular to the flow of material out of the separation chamber. This provides a sensitive means of measuring fluxes and compositions of cellular material out of the separation chamber. Two dimensional detection is critical for characterizing fluxes and compositions of cellular material exiting the separation chamber because such material are typically inhomogeneously dispersed through an extraction port.

Fourth, detection of light corresponding to a two-dimensional area also provides optical systems capable of simultaneously monitoring a plurality of operating conditions important to controlling blood processing. In contrast to conventional optical monitoring techniques, the methods and devices of the present invention are capable of multifunctional operation because the measured two-dimensional distribution of scattered and/or transmitted light intensities correspond to a plurality of different optical axes. In the present invention reference to multifunctional operation relates to the ability of an optical monitoring system to monitor and/or control a plurality of operating or experimental conditions important to optimal operation of a density centrifuge. The ability to simultaneously generate and analyze a plurality of measurements from a single two-dimensional distribution of scattered and/or transmitted light intensities is beneficial in the present invention because it allows diverse measurements to be correlated and analyzed in combination to provide a greater understanding of the operating conditions of the centrifuge during blood processing. For example, optical methods of the present invention are capable of simultaneously monitoring the position of phase boundaries, the composition of extracted components, the fluxes of components out extraction ports, the identity of blood samples, the presence of leaks of blood components out of the separation chamber or any combination of these. In addition, the ability to selectively adjust the position and size of the observation region expands the functional capabilities of the optical monitoring system of the present invention. Optical monitoring and control systems capable of multifunctional operation are beneficial because they substantially reduce the time, effort and expense associated with personnel overseeing a blood processing device. In addition, the devices and methods of the present information provide highly reproducible separation conditions capable of generating separated blood components having well-characterized and highly reproducible compositions namely purities. Furthermore, multifunctional monitoring and control systems are capable of dealing with rapid changes in blood separation conditions and are well designed for overseeing processing of blood samples having atypical compositions, such as the samples encountered during therapeutic procedures.

In another aspect, the present invention provides optical monitoring and control systems for blood processing utilizing separation methods other than pure density centrifugation, such as separation on the basis of shape, size, sedimentation velocity, diffusion rate, surface chemistry characteristics or any combination of these techniques. For example, the present invention is capable of monitoring and controlling blood processing via multiple stage processing. In a preferred embodiment of multiple stage processing, a blood sample is first fractionated into discrete blood components by density centrifugation. Next, one or more selected blood components are extracted from the density centrifuge and further separated by shape and size filtration, centrifugal elutriation, affinity chromatography or any combination of these methods. In this embodiment, optical monitoring and control systems of the present invention control the extent of separation achieved in both stages.

In a preferred embodiment, two stage blood processing is achieved by a combination of density centrifugation and centrifugal elutriation methods. Exemplary methods and devices for blood processing by centrifugal elutriation are described in U.S. Pat. No. 6,334,842. In a preferred embodiment, a blood sample is separated into components via density centrifugation in a first stage and a selected blood component or plurality of blood components is extracted and subjected to further processing via centrifugal elutriation. In a preferred embodiment, the selected component is introduced into a flow of liquid elutriation buffer and passed into a funnel-shaped separation chamber located in a spinning centrifuge. As the liquid buffer flows through the separation chamber, the liquid sweeps smaller sized, slower sedimenting cells toward an elutriation boundary within the chamber. Larger, faster-sedimenting cells, however, migrate toward an area of the chamber having the greatest centrifugal force. By selecting the proper fluid flow rates through the funnel-shaped separation chamber, faster sedimenting cells and slower-sedimenting cells are separately extracted from the separation chamber and subsequently collected. Therefore, the combination of density centrifugation and centrifugal elutriation provides a method of separating blood components based on both density and sedimentation velocity.

The methods, devices and device components of the present invention are capable of monitoring and controlling multiple stage blood processing. Particularly, the optical monitoring and control systems of the present invention are capable of generating two-dimensional distribution of scattered and/or transmitted light intensities comprising images of blood separation in first and second stages of a blood processing device. First, the monitoring system of the present invention is capable of measuring two-dimensional distributions of scattered and/or transmitted intensities of light from a separation chamber of the density centrifuge, which characterize the composition, purity and extraction rate of the blood component selected for additional processing via centrifugal elutriation. Further, in one aspect of the present invention two-dimensional distributions of scattered and/or transmitted light intensities are used to optimize separation and extraction conditions in the first stage to achieve a desired composition for additional processing in the second stage. In one embodiment, for example, phase boundary positions in the first stage are selected and maintained in a manner minimizing the presence of red blood cells and/or white blood cells in a platelet-containing blood component selected for additional processing in the second stage. Second, the optical monitoring and control systems of the present invention are capable of measuring two-dimensional distributions of scattered and/or transmitted light intensities comprising images of the elutriation chamber itself as it is rotated about the central axis of a centrifuge. Two-dimensional distributions of scattered and/or transmitted light intensities of light from the elutriation chamber provide direct measurements of the composition of the blood component undergoing additional processing, which can be compared to measurements acquired by monitoring separation achieved in the first stage to evaluate the degree of separation achieved during extraction. For example, the brightness or color of a two-dimensional distribution of scattered and/or transmitted light intensities of light from an elutriation chamber provide measurements of the composition of a blood component selected for further processing, for example the abundance of red blood cells in the elutriation chamber.

In addition, two-dimensional distributions of scattered and/or transmitted light intensities generated by the present invention provide direct measurements of the composition, and flux of sub-components separated in the second stage. Characterization of the composition of a selected subcomponent is beneficial because it ensures that the collected sub-component is adequate for use in transfusion or infusion therapies. For example, the methods of the present invention are useful for leukoreduction methods by optically characterizing platelet-containing sub-components to ensure levels of white blood cells are low enough as to avoid complication upon infusion related to undesirable immune responses and viral transmission. Alternatively, the methods of the present invention are useful in immunotherapy for characterizing extracted white blood cell-containing sub-components and to optimizing separation conditions in a second stage to minimize the levels of red blood cells and platelets in the purified sub-component or to collect a particular white blood cell-type.

The methods, devices and device components of the present invention are useful for monitoring and controlling blood processing other than separation of blood into components. Exemplary processing applications capable of being monitored and controlled by the present invention include, but are not limited to, blood component washing, pathogen reduction and pathogen removal, red blood cell deglycerolization and the addition of blood components and/or blood processing agents to blood samples.

In another aspect, the present invention provides a method of detecting the occurrence and extent of hemolysis of red blood cells during blood processing, particularly centrifugation. Hemolysis can occur during blood processing when motion of the blood sample results in a degradation of red blood cells leading to the release of hemoglobin. Upon its release, hemoglobin migrates to less dense blood components, such as the plasma containing component. The release and migration of free hemoglobin to lower density blood components is able to be optically monitored in the present invention because hemoglobin absorbs light strongly in the visible region of the spectrum, particularly over the wavelength range of about 500 nm to about 600 nm, and thus, decreases detected light intensities. Accordingly, measured two-dimensional distributions of scattered and/or transmitted light intensities can be used to determine light absorption over this wavelength range to characterize the extent of hemolysis during blood processing. In these measurements, large absorption over the wavelength range of 500 nm to 600 nm corresponds to separation conditions resulting in substantial hemolysis. Further, in one embodiment such measurements are used as the basis of control signals to optimize the flow conditions in a blood processing device to minimize the occurrence of hemolysis. In a one embodiment, the lower density blood component is illuminated with both green light and red light, and transmitted light, scattered light, or both, is collected and detected corresponding to each illumination color. A comparison of the intensities of scattered and/or transmitted light corresponding to each illumination color provides an accurate measurement of the extent of hemolysis in the sample.

In another aspect, the present invention provides methods of monitoring and controlling a density centrifuge capable of separating at least two optically differentiable components of a fluid and having a separation chamber rotating about a central rotation axis wherein said components in the centrifuge separation chamber separate along a separation axes which rotate about the central rotation axis, comprising the steps of: (1) illuminating the density centrifuge with an incident light beam provided by a light source; (2) collecting light from a observation region on the density centrifuge and directing said light onto a two-dimensional detector; (3) positioning at least a portion of said observation region such that phase boundaries are viewable; and (4) detecting said light with said two-dimensional detector, which generates a two-dimensional distribution of scattered and/or transmitted intensities of light from of said observation region; (5) measuring the position of at least one phase boundary between said components along said separation axis. Optionally, the methods of the present invention further comprise the step of measuring the composition of a component exiting the separation chamber via an extraction port. Optionally, the methods of the present invention also include the step of adjusting the operating conditions of said centrifugation device to achieve substantial separation of said optically differentiable components.

The invention is further illustrated by the following description, examples, drawings and claims.

BRIEF DESCRIPTION OF THE DRAWINGS

In FIGS. 6A and 6B, triangles schematically represent white blood cells and platelets, circles schematically represent red blood cells and areas having lines schematically represent plasma.

In FIG. 7, triangles schematically represent white blood cells and platelets, circles represent red blood cells and areas having lines represent plasma.

DETAILED DESCRIPTION OF THE INVENTION

Figure 1:
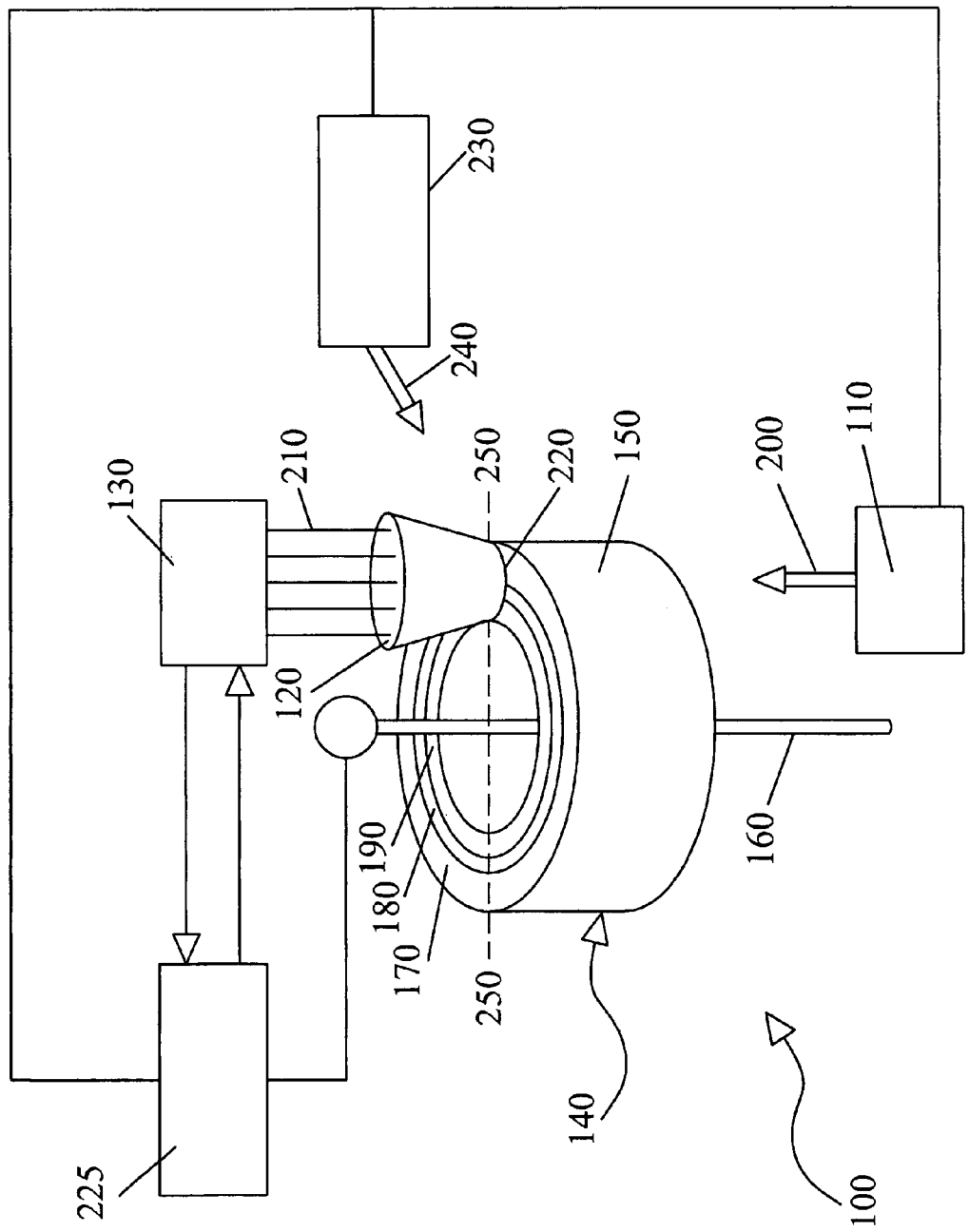
FIG. 1 is a schematic drawing showing an optical monitoring and control system of the present invention.

Referring to the drawings, like numerals indicate like elements and the same number appearing in more than one drawing refers to the same element. In addition, hereinafter, the following definitions apply:

The terms "light" and "electromagnetic radiation" are used synonymously and refer to waves of electric and magnetic fields that also exhibit particle-like behavior. Light useful for the methods of the present invention includes gamma rays, X-rays, ultraviolet light, visible light, infrared light, microwaves, radio waves or any combination of these. "Depth of field" refers to the zone of acceptable sharpness in a picture and/or image extending in front of and behind the plane of the subject. Depth of field may by quantitatively characterized as the range of distances reproduced in a picture and/or image over which the image is not unacceptably less sharp than the sharpest part of the image. The term "depth of field" is intended to be interpreted consistently with the mean of this term as understood by those having skill in the art. A light collection element may be characterized in terms of its depth of field.

"Optically differentiable" refers to differences in the optical characteristics of two or more illuminated materials. Optically differentiable materials can have different absorption coefficients, extinction coefficients, scattering cross sections, fluorescence excitation wavelengths, phosphorescence excitation wavelengths, emission wavelengths or any combinations of these characteristics. As the optical characteristics of most materials depend on wavelength, materials can be optically differentiable when illuminated by light having a selected wavelength range. Exemplary optically differentiable materials useable in the present invention include, but are not limited to, erythrocytes, eosinophils, basophils, monocytes, lymphocytes, granulocytes, platelets (thrombocytes), plasma proteins, and plasma. Exemplary optically differentiable materials further include the materials comprising a blood processing device or blood sample container, such as polymeric materials such as plastics, metals, and glass.

"Flux of cellular material exiting the separation chamber" refers to the amount of cells, such as erythrocytes, leukocytes, thrombocytes or any combination of these, which cross a defining area, such as the cross-sectional area of an extraction port of blood processing device, such as a density centrifuge, elutriation separation chamber or filtration separation device, per unit time. Flux of cellular material can be expressed in units of: (number of cells) $cm^{-2} s^{-1}$.

"Optical communication" refers to the orientation of two or more elements such that light is capable of propagating from one element to another element. Elements can be in optical communication via one or more additional elements such as reflectors, lenses, fiber optic couplers, wave guides or any combinations of these. In one embodiment of the present invention, one or more light sources and a light collection element can be positioned in optical communication with an observation region on a blood processing device, such as a density centrifuge. In this embodiment, at least a portion of light from one or both of the light sources is directed onto an observation region and the light collection element is positioned such that it is capable of collecting at least a portion of light scattered transmitted, or both from the observation region.

"Light collection element" refers to a device or device component which collects light and distributes the collected light in a desired way. Light collection elements useable in the present invention are capable of collecting at least a portion of transmitted light, scattered light or both generated upon illumination of an observation region on a blood processing device. Exemplary light collection elements of the present invention are capable of collecting light in a manner generating an image of an observation region on a two dimensional detector. Light collection elements of the present invention include, but are not limited to, fixed focus lenses, spherical lenses, cylindrical lenses, aspheric lenses, wide angle lenses, zoom lenses, concave lenses, convex lenses, biconcave lenses, biconvex lenses, lens systems comprising a plurality of lenses, wave guides, fiber optic couplers, reflectors, spherical mirrors, aspherical mirrors, prisms, apertures, lenses, or any combination or equivalents of these. Light collection elements of the present invention are capable of directing collected light onto another optical device or device component, such as a two-dimensional detector. Light collection elements include at least one lens system having a selectively adjustable field of view and/or focal length. Light collection elements can be translatable along a detection axis, which is perpendicular to a central rotation axis.

"Field of view" refers to the angular distribution of light rays which are collected and detected by an optical detection system, such as a light collection element in optical communication with a two dimensional detector. The field of view of a two dimensional imaging system of the present invention is the portion of an illuminated object or plurality of objects which is represented in a two dimensional image. Optical detection systems of the present invention can have a fixed field of view or a field of view which is selectively adjustable.

"Blood processing" refers to the manipulation of a blood sample or component thereof, to realize a change in composition. Blood processing includes methods of separating blood or a component thereof into components or subcomponents, leukoreduction, pathogen inactivation, blood filtering, oxygenating blood and blood components, dialysis, blood purification or clearing, pathogen removal, blood and blood component warming, blood component washing, and red blood cell deglycerolization. The present invention provides improved methods of blood processing wherein a blood sample or component thereof is separated into components or subcomponents on the basis of density, size, diffusion rate, sedimentation velocity, surface chemistry properties or combinations of these characteristics.

"Observation region" refers to an illuminated portion of an object or plurality of objects which generates transmitted light, scattered light or both at least a portion of which that is collected by a light collection element and detected by a two-dimensional detector. In preferred embodiments of the present invention, the observation region is positioned on a blood processing device, component of a blood processing device, such as an optical cell, or a blood sample container. The size and position of the observation region is determined by the field of view of the light collection element, the position of the light collection element from the blood processing device, the area of the two-dimensional detector and the position of the two-dimensional detector with respect to the light collection element. In an embodiment, the size, shape and position of the observation region is selectively adjustable by controlling the position of the light collection element with respect to the blood processing device and the field of view of the light collection element. In an embodiment of the present invention, one or more phase boundaries between optically differentiable components are viewable in the observation region. In another preferred embodiment, at least one separated component is viewable in the observation region. In another preferred embodiment, at least one extraction port is viewable in the observation region.

"Interface region" refers to a region of the a blood separation device wherein two or more optically differentiable phases are viewable. For example, in one embodiment the interface area is defined by a region of the separation chamber wherein the phase boundary between a red blood cell containing component and a plasma containing component is viewable. In another embodiment, the interface area is defined by a region of the separation chamber wherein the phase boundary between a red blood cell containing component and a mixed-phase white blood cell and platelet containing component and the phase boundary between the mixed-phase white blood cells and platelet containing component and plasma containing component are viewable. In another embodiment, the phase boundary between a white blood cell containing component and a platelet containing component are viewable. In the present invention, a two-dimensional distribution of scattered and/or transmitted light intensities of light from an interface region provides a measurement of the position of one or more boundary layers along a plurality of separation axes. In an exemplary embodiment, the interface region is an optical cell of a separation chamber.

"Composition-monitoring region" refers to portion of a blood processing device occupied by at least one separated phase. For example, the composition-monitoring region can be defined by a region of a separation chamber in a density centrifuge wherein light is transmitted through one or more discrete phase in the separation chamber upon illumination by an incident light beam. As the transmission of light through a separated compound depends on identity and concentration of cellular and non-cellular material, monitoring scattered light, transmitted light, or both, from a composition-monitoring region provides a measurement of the identity, concentration, cell type, purity of at least one component or any combination of these. In an exemplary embodiment, the composition monitoring region is an extraction port in an optical cell of a separation chamber.

"Blood sample" and "blood" are used synonymously to refer to whole blood, one or more blood component, one or more blood products, or any combination of these. "Blood component" and "blood product" as used herein include cellular components, noncellular components of blood and combinations of cellular and noncellular components of blood. Exemplary cellular components include but are not limited to erythrocytes (red blood cells), leukocytes (white blood cells), and thromobocytes (platelets) and combinations of these materials. Leukocytes comprise monocytes, granulocytes, agranulocytes, lymphocytes. Exemplary noncellular components include but are not limited to plasma, dissolved salts and minerals and plasma proteins. A blood component can be further fractionated into blood sub-components.

"Two-dimensional detector" refers to any detector capable of measuring a two-dimensional distribution of scattered and/or transmitted light intensities, such as a two-dimensional distribution of scattered and/or transmitted light intensities corresponding to an image of a portion or component of a blood processing system. Exemplary two-dimensional detectors measure two-dimensional distributions of scattered and/or transmitted light intensities comprising images of an observation region on a separation chamber of a blood processing system. Optionally, two-dimensional detectors generate one or more output signals which are received by another device component as input. Preferred two-dimensional detectors of the present invention include, but are not limited to, a charge coupled device (CCD), a two-dimensional photodiode array, a two-dimensional photoconductive array, a two-dimensional pyroelectric array, a digital camera, a complimentary metal oxide semiconductor (CMOS) detector, a plurality of photodiodes and a plurality of photomultiplier tubes. Two dimensional detectors may measure two-dimensional distribution of scattered and/or transmitted light intensities corresponding to a monochrome image or a color image. In one embodiment, two dimensional-detectors of the present invention have the ability to selectively detect light corresponding to a selected wavelength range. In one embodiment, two dimensional-detectors of the present invention measure a plurality of two-dimensional distribution of scattered and/or transmitted light intensities corresponding to a plurality of selected wavelength ranges, such as wavelength ranges corresponding to red light, green light and blue light.

"Separation axis" refers to the axis along which blood components having different densities are separated in a density centrifuge. As a separation chamber is rotated about a central rotation axis in a density centrifuge, the centrifugal force is directed along separation axes. Accordingly, a plurality of axes rotates about the central rotation axis of a density centrifuge. In a preferred embodiment, the optical monitoring methods of the present invention are capable of measuring the positions of one or more phase boundaries between optically differentiable components along the separation axis.

"Flux" refers to the rate at which cellular material, non-cellular material, or both, crosses a defining plane. Flux can be expressed by the following unit: (number of X) $cm^{-2}$ $s^{-1}$, where in X is a cellular component or non-cellular component of blood. In a preferred embodiment, the optical monitoring methods of the present invention are capable of measuring the flux of cellular components including, but not limited to, red blood cells, neutrophils, esinophils, basophils, monocytes, lymphocytes, platelets or any combination of these, through an extraction port of a separation chamber.

"Image" refers to a visual representation of one or more patterns of light originating from an observation region. Images of the present invention can be two dimensional images or three dimensional images. The present invention provides methods and devices whereby a measured two-dimensional distribution of scattered and/or transmitted light intensities provides an image corresponding to an observation region, such as an observation region positioned on a separation chamber an/or optical cell of a density centrifuge. In one embodiment, images generated by the methods and devices or the present invention correspond to light scattered, transmitted, or both, from one or more components undergoing density centrifugation, such as components of a blood sample. Alternatively, images generated by the methods and devices or the present invention correspond to light scattered, transmitted, or both, from a region of the density centrifuge itself, such as the optical cell of a separation chamber. Two-dimensional distributions of scattered and/or transmitted light intensities and images measured by the methods and devices of the present invention can be used to determine the position of phase boundaries between optically differentiable components along a separation axis, the composition of selected components, the flux and composition of cellular or non-cellular materials out of the separation chamber, the identity of a blood sample and the identity of the kit or container containing a blood sample.

"Resolution" refers generally to the ability of an optical measurement to illustrate an image comprising patterns of light originating from an observation region. The greater the resolution the sharper the image. Resolution of a two-dimensional optical measurement is commonly expressed in terms of number of pixels on the horizontal and vertical axis by the following equations:

$$\text{horitonal resolution} = \frac{(P_h)}{L_h} \quad (I)$$

$$\text{vertical resolution} = \frac{(P_v)}{L_v} \quad (II)$$

wherein $P_h$ and $P_v$ are the number of pixels extending along the horizontal and vertical axes, respectively, and $L_h$ and $L_v$ are the lengths of the image along the horizontal and vertical axes, respectively. Optical monitoring systems of the present invention are capable of generating high resolution images of an observation region.

"Epi-illumination" refers to the illumination of an object and generation of scattered light. In epi-illumination, light is directed to the object along an axis of illumination which is different than the optical axis whereby scattered light is collected and detected.

"Parallel" refers to a geometry in which two surfaces are equidistant from each other at all points and have the same direction or curvature. Substantially parallel refers to a geometry in which angular deviations from absolute parallelism are less than 10 degrees, and preferably less than 0.5 degrees for some applications. The present invention includes optical cells for blood processing comprising a plurality of optical surfaces positioned in substantially parallel planes.

In the following description, numerous specific details of the devices, device components and methods of the present invention are set forth in order to provide a thorough explanation of the precise nature of the invention. It will be apparent, however, to those of skill in the art that the invention can be practiced without these specific details. Reference in the specification to "a preferred embodiment," "a more preferred embodiment" or "an exemplary embodiment" means that a particular feature, structure, or characteristic set forth or described in connection with the embodiment is included in at least one embodiment of the invention. Reference to "preferred embodiment," "a more preferred embodiment" or "an exemplary embodiment" in various places in the specification do not necessarily refer to the same embodiment.

This invention provides methods, devices and device components for monitoring and controlling blood processing, preferably by density centrifugation, centrifugal elutriation and/or filtration. In particular, the present invention provides a multifunctional optical monitoring system capable of measuring two-dimensional distributions of scattered and/or transmitted light intensities comprising images corresponding to an observation region, which is particularly useful for achieving effective separation of blood into individual components and subsequent collection of separated components.

FIG. 1 schematically illustrates an exemplary embodiment of the optical monitoring system of the present invention capable of measuring a two-dimensional distribution of scattered and/or transmitted light intensities corresponding to patterns of light originating from an observation region on a separation chamber. The illustrated monitoring system 100 comprises light source 110, light collection element 120, and two-dimensional detector 130. Light source 110 is in optical communication with a density centrifuge 140 comprising separation chamber 150 which rotates about central rotation axis 160. Rotation about central rotation axis 160 results in separation of a blood sample in the separation chamber into discrete blood components along a plurality of rotating separation axes oriented orthogonal to the central rotation axis 160. In a preferred embodiment, separation chamber 150 is held in a circular filler (not shown in FIG. 1), which is also capable of rotation about central rotation axis 160. In one embodiment of the present invention, a filler comprises a disc having an internal, circular groove wherein the separation chamber is positioned and fastened. During operation of the density centrifuge, the filler is operationally connected to a rotating means such that both filler and separation chamber are rotated about the central rotation axis 160. In the schematic shown in FIG. 1, the blood sample is separated into an outer higher density phase corresponding to a red blood cell component 170, an intermediate density phase corresponding to a white blood cell and platelet-containing component (e.g. buffy coat) 180 and a lower density inner phase corresponding to a platelet enriched plasma component 190.

Light source 110 provides incident light beam 200, which illuminates an observation region 220 on separation chamber 150, preferably in a manner generating scattered and/or transmitted light from the blood sample undergoing separation. In one embodiment, light source 110 is capable of generating an incident light beam, a portion of which is transmitted through at least one blood component undergoing separation in separation chamber 150. At least a portion of scattered and/or transmitted light 210 from the observation region 220 is collected by light collection element 120. Light collection element 120 is capable of directing at least a portion of the collected light 210 onto two-dimensional detector 130. The two-dimensional detector 130 detects patterns of scattered and/or transmitted light 210 from the observation region, thereby measuring two-dimensional distributions of scattered and/or transmitted light intensities. In an exemplary embodiment, two-dimensional distributions of scattered and/or transmitted light intensities comprise images corresponding to patterns of light originating from the observation region 220. In one embodiment, images of the present invention are monochrome images, which provide a measurement of the brightness of separated blood components along the separation axis. Alternatively, images of the present invention are color images, which provide a measurement of the colors of separated blood components along the separation axis.

Observation region 220 is positioned on a portion of the density centrifuge 140, preferably on the separation chamber 150. In the exemplary embodiment illustrated in FIG. 1, separated blood components and phase boundaries between optically differentiable blood components are viewable in observation region 220. In one embodiment, the observation region is positioned on an optical cell of the separation chamber having windows for transmitting the incident beam through the blood sample undergoing processing. In an alternative preferred embodiment, one or more extraction ports (not shown in FIG. 1) are viewable in observation region 220. In another embodiment, observation region 220 is positioned on the top of the separation chamber 150 such that leaks of the blood sample and/or improper alignment of the separation chamber or filler are viewable. In another alternative embodiment, the observation region 220 is positioned on a portion of the separation chamber such that the composition of a separated blood component can be directly monitored. For example, a monitoring system of the present invention provides a method of characterizing the type of cellular component collected and counting the amount of cells extracted from the separation chamber as a function of time. Alternatively, the monitoring system is arranged such that the concentration of non-cellular blood components, such as blood plasma proteins, is directly measured. In one embodiment, the observation region 220 is arranged such that a plurality of measurements are obtained from every measured two-dimensional distribution of scattered and/or transmitted light intensities.

Optionally, the observation region 220 can also be illuminated by epi-illumination light source 230, which is positioned on the same side of the separation chamber as the light collection element and two-dimensional detector. Epi-illumination light source 230 is positioned such that it generates an incident beam 240 which is scattered by the blood sample and/or centrifuge. A portion of the light from Epi-illumination light source 230 scattered by the separation chamber and is collected by light collection element 120 and detected by two-dimensional detector 130, thereby measuring a two-dimensional distribution of scattered and/or transmitted light intensities.

In one embodiment, two-dimensional detector 130 is also capable of generating output signals corresponding to the measured two-dimensional distributions of scattered and/or transmitted light intensities and/or images. In the exemplary embodiment shown in FIG. 1, two-dimensional detector 130 is operationally connected to a centrifugation device controller 225 capable of receiving the output signals. In one embodiment, centrifugation device controller 225 displays the measured intensity distributions, stores the measured intensity distributions, processes measured intensity distributions in real time, transmits control signals to various optical and mechanical components of the monitoring system and centrifuge or any combination of these. In a preferred embodiment, centrifugation device controller 225 is operationally connected to centrifuge 140 and is capable of adjusting selected operating conditions of the density centrifuge, such as the flow rates of cellular and non-cellular components out of the separation chamber, the position of one or more phase boundaries along the separation axes, rotational velocity of the separation chamber about central rotation axis 160, the infusion of anticoagulation agents or other blood processing agents to the blood sample, or any combination of these.

As shown in FIG. 1, centrifugation device controller 225 can also be operationally connected to light source 110 and/or epi-illumination light source 230. In this embodiment, centrifugation device controller 225 and/or two-dimensional detector 130 are capable of generating output signals for controlling illumination conditions. For example, output signals from two-dimensional detector can be used to control the timing of illumination pulses, illumination intensities, the distribution of illumination wavelengths and/or position of light source 110 and/or epi-illumination light source 230. As also shown in the embodiment illustrated in FIG. 1, centrifugation device controller and two-dimensional detector are two way communication. In this embodiment, centrifuge device controller sends control signals to two-dimensional detector 130 to selectively adjust detector exposure time, detector gain and to switch between monochrome and color imaging.

Figure 2:
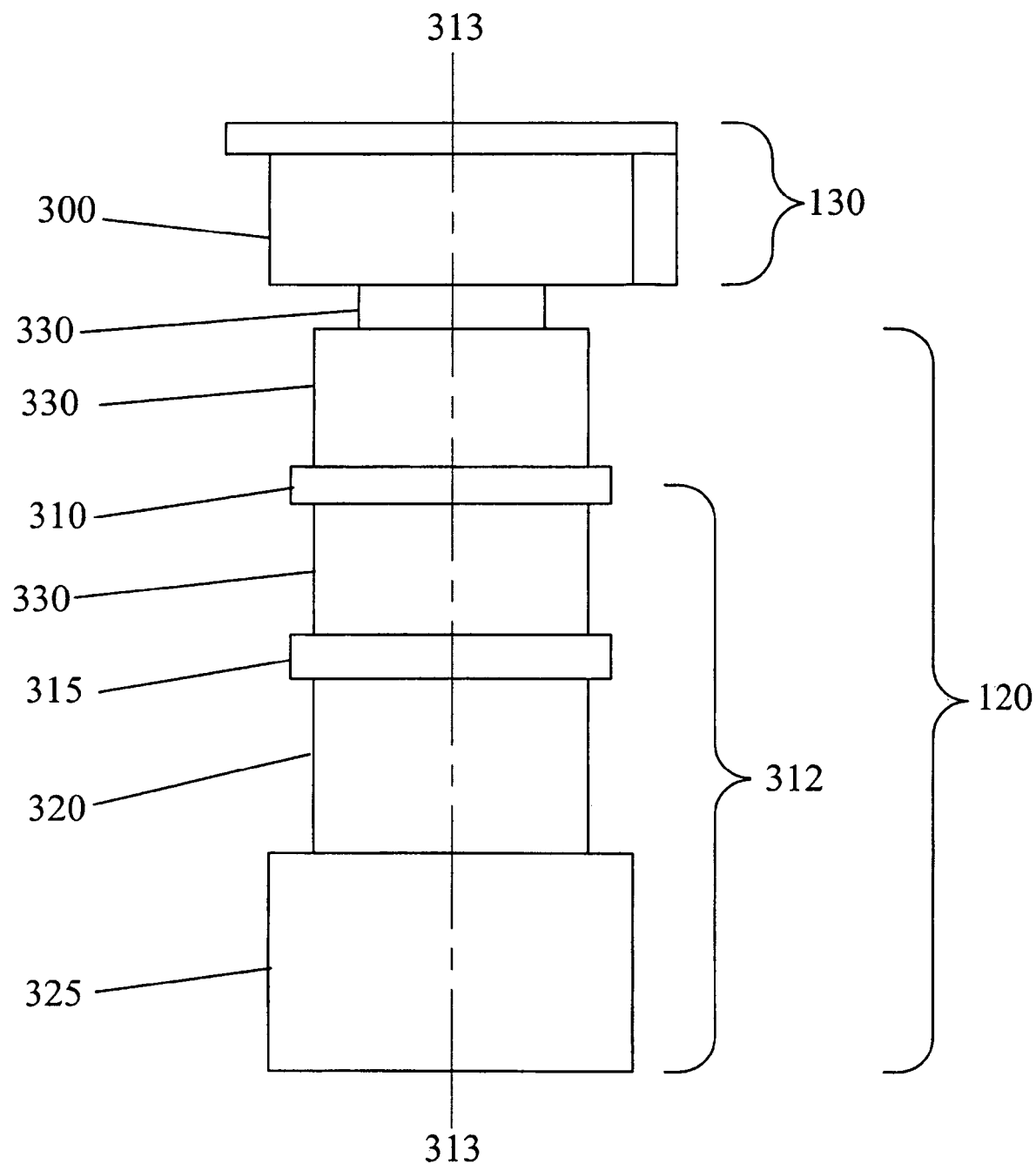
FIG. 2 is a schematic drawing showing a side view of a light collection element and two-dimensional detector useable in the present invention.

FIG. 2 shows a schematic drawing of a side view of a light collection element 120 and two-dimensional detector 130 of the present invention. Two-dimensional detector comprises a digital camera 300, aperture 310, and a close focus lens system 312, which are disposed along optical axis 313. Light originating from the observation region, for example light propagating substantially parallel to optical imaging axis 313, is collected by close focus lens system 312 and directed onto digital camera 300. In the exemplary embodiment shown in FIG. 2, the close focus lens system 312 comprises zoom lens element 315, close focus lens element 320, and focus lens element 325. Use of a close focus lens system 312 is beneficial due to the large range of fields of view provided. Optionally, light collection element 120 and two-dimensional detector 130 further comprises one or more spacers 330.

Use of an aperture 310 in this embodiment is beneficial because it allows the exposure of the camera to transmitted or scattered light to be selectively gated on and off as the separation chamber is rotated. Further, use of an aperture is beneficial because it is useful for controlling the light exposure time of the detector. Aperture size can be varied in the present invention. Because the separation chamber is rotating at a known, rotational velocity, proper selection of the aperture timing allows the position of the observation area on the separation chamber to be selectively adjusted with great accuracy, preferably to within 0.1 mm or better. Use of an aperture is also beneficial because it provides precise control over the detector exposure times needed to measure two dimensional distributions of transmitted and/or scattered light intensities comprising high quality images of an observation region.

Referring again to the embodiment illustrated in FIG. 1, light collection element 120, two-dimensional detector 130, or both, can be arranged such that they are moveable, for example moveable along a first detection axis 250, which is oriented orthogonal to the central rotation axis of the centrifuge. Movement of light collection element 120 in a direction along detection axis 250 adjusts the position of observation region 220 on the density centrifuge. In another embodiment, light collection element 120 is also capable of movement in a direction along a second detection axis (not shown) which is orthogonal to the first detection axis 250. The present invention also includes an embodiment wherein light source 110, epi-illumination light source 230, or both, are also capable of movement in a manner to optimize illumination and subsequent detection of transmitted and/or scattered light from the selectively adjustable observation region.

Figure 3:
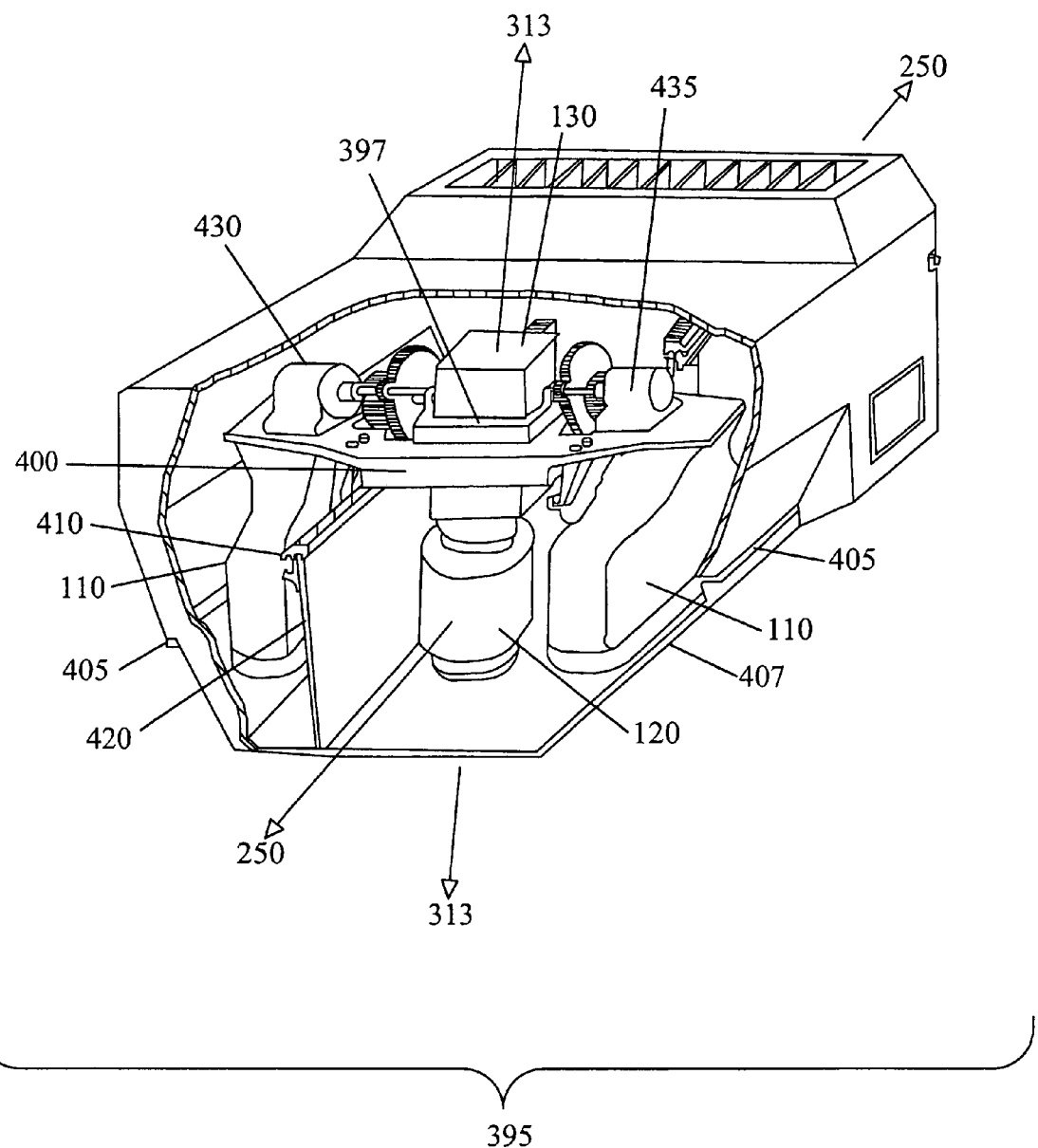
FIG. 3 is a schematic drawing showing a front cut-away view of a light collection element and two-dimensional detector useable in the present invention.

FIG. 3 (not drawn to scale), shows a cut away view of an exemplary embodiment having a light collection element 120 and two-dimensional detector 130 which are capable of translation along detection axis 250. In the embodiment illustrated in FIG. 3, two-dimensional detector 130 and light collection element 120 are supported by motorized flying crane assembly 400. The monitoring system 395 has slide rails 405 for mounting to a density centrifuge and is equipped with a transmissive glass bottom plate 407 separating components of the monitoring system from the density centrifuge. Optical glass bottom plate 407 is substantially transparent to light originating from the observation region and protects light collection element 120 and two-dimensionally detector 130 from dust, debris and leaked blood components. Optionally, mounting collar 397 can be provided to dampen vibrations originating from rotation of the centrifuge, which can lead to misalignment of two-dimensional detector 130 and light collection element 120.

Incorporation of motorized flying crane assembly 400 allows translation of two-dimensional detector 130 and light collection element 120 along detection axis 250. As shown in FIG. 3, crane assembly 400 rides on wheel guide support rails 410, which are mounted on top of divider walls 420. Divider walls 420 provide a support for crane assembly 400 and also serve to minimize the unwanted detection of background light. The crane assembly 400 is driven by a selectively adjustable stepping motor 430 and digital rotational encoder 435 capable of providing high resolution positional increments, for example increments of about 10 micrometers or less.

The monitoring system is also equipped with illumination light source 110 for illuminating the density centrifuge. In the embodiment shown in FIG. 3, light source 110 is supported by flying crane assembly 400. An incident light beam is generated by the light source 110 and directed through glass bottom pane 407 toward the density centrifuge. Alternatively, light source 110 further include one or more reflectors (not shown) to provide illumination from below the density centrifuge. The incident light beam is transmitted and/or scattered by the density centrifuge and a portion of light translating substantially parallel to optical imaging axis 313 is collected by the light collection element 120 and detected. In a preferred embodiment, light source 110 comprises a plurality of light emitting diode sources.

Figure 4:
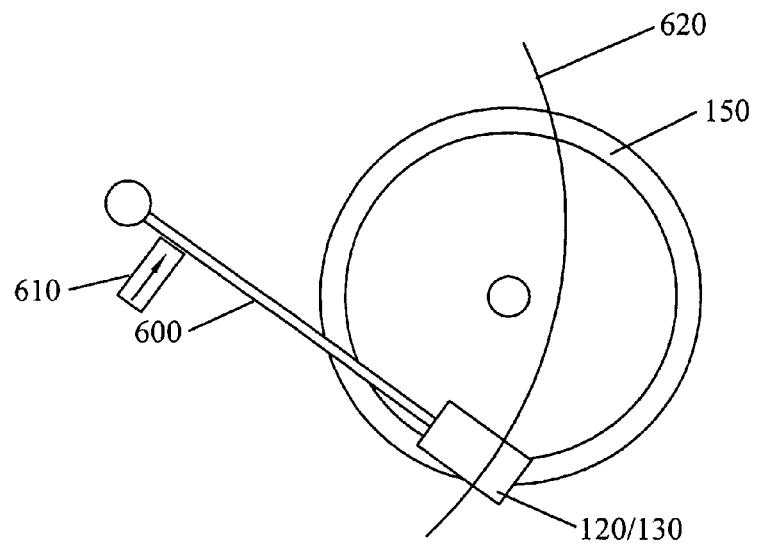
FIG. 4 is a schematic drawing showing a top plan view of a mounting configuration providing for selective adjustment of the position of the light collection element and two-dimensional detector.

FIG. 4 illustrates another mounting configuration providing movement of the light collection element 120 and two-dimensional detector 130. As illustrated in FIG. 4, light collection element 120 and two-dimensional detector 130 are mounted on arm 600, which is operationally connected to actuator 610. Arm 600 is capable of rotation along arc path 620 upon action of actuator 610. As shown in FIG. 4, movement along arc path 620 translates light collection element 120 and two-dimensional detector 130 past a range of regions of separation chamber 150. Optionally, light collection element 120 and two-dimensional detector 130 can be supported by a low friction support surface operationally connected to the filler (not shown) which holds the separation chamber in place. Mounting on the filler or bucket or container is particularly advantageous for batch processing or for separation in bags or other containers. The light collection element 120 and two-dimensional detector 130 can also be mounted on a cover of the centrifuge. An advantage of the mounting configuration shown in FIG. 4 is that it is less susceptible to vibrations and spatial distortions introduced upon translation than other monitoring systems providing for translation of the light collection element and detector.

Figure 5:
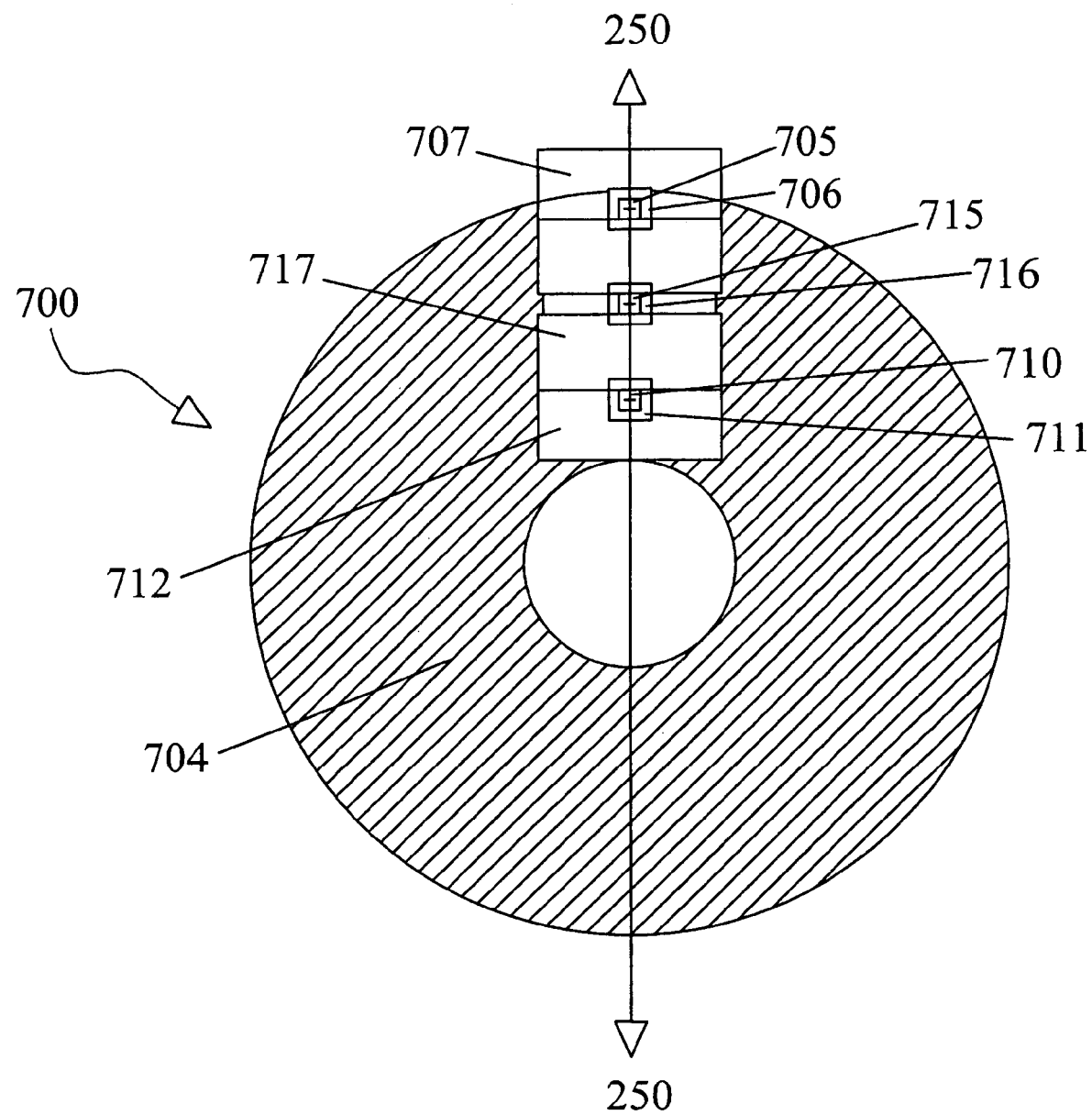
FIG. 5 is a schematic drawing showing observation regions of monitoring systems of the present invention.

FIG. 5 shows a plurality of observation regions provided by an optical monitoring system of the present invention having a light collection element and two-dimensional detector capable of translation along a detection axis 313 oriented perpendicular to the central rotation axis of a density centrifuge 700. The squares shown in FIG. 5 represent various fields of view provided by the present invention corresponding to a variety of light collection element and two-dimensional detector positions along detection axis 313. Squares having the same areas but different center points correspond to different positions of the light collection element and detector along the detection axis. Squares having different areas but same center points corresponding to different fields of view for a selected light collection element and detector position along the detection axis. A smaller field of view is preferred for some applications because it provides higher resolution images of an observation region. Alternatively, a larger field of view is preferred for some applications because of the more expansive observation region it provides. Hatched region 704 represents additional regions of density centrifuge 700 which can be optically characterized by selectively adjusting the illumination timing and detector exposure time upon rotation of the separation chamber about the central rotation axis.

Squares 705, 706 and 707 represent different fields of view achievable for first detection configuration wherein light collection element and two-dimensional detector are positioned distal to the center 710 of density centrifuge 700. While field of view 705 provides images capturing a small area of density centrifuge 700, field of view 705 provides images having higher resolution than wider fields of view 706 and 707. Squares 710, 711 and 712 are fields of view corresponding to a second detection configuration wherein light collection element and two-dimensional detector are positioned proximate to the center 710 of density centrifuge 700. Squares 715, 716 and 717 are fields of view corresponding to a third detection configuration wherein light collection element and two-dimensional detector are positioned along detection axis 313 and located at an intermediate distance from center 710 of density centrifuge 700.

Selection of the appropriate detector light exposure timing, field of view position and field of view area provides selective control over the position of the observation region on the blood processing device. Reference to detector exposure timing refers to the time over which the detector is exposed to transmitted and/or scattered light. The detector light exposure timing determines the angular orientation of the rotating separation chamber at the time in which a two dimensional distribution of transmitted and/or scattered light intensities is measured. In one embodiment, the exposure timing of the detector is controlled by triggering the opening and closing of an aperture, by triggering pulsed illumination and/or by detector gate settings in the digital camera itself. As shown in FIG. 5, use of a two-dimensional detector provides monitoring systems capable of monitoring large regions of a density centrifuge.

Light sources of the present invention comprise any device capable of generating one or more incident beams for illuminating an observation region on the density centrifuge. Exemplary light sources of the present invention comprise a single lamp or a plurality of lamps positioned to illuminate a single side or multiple sides of a density centrifuge. Light sources useable in the present invention include, but are not limited to, light emitting diodes and arrays of light emitting diode light sources, xenon flash lamps, filament lamps, pulsed lasers, continuous wave lasers and fluorescent lamps. Use of light emitting diode light sources is preferred for some applications because they are capable of generating precisely timed illumination pulses. Use of a xenon flash lamp is preferred for some applications because it provides very high light intensities. Preferred light sources generate an incident light beam having a substantially uniform intensity. In one embodiment, light sources of the present invention generate an incident beam having a selected wavelength range and selected intensity. In one embodiment, light sources of the present invention further comprise fiber optical light pipes or waveguides capable of controlling the illumination area on the blood processing device.

In a preferred embodiment, the optical monitoring system of the present invention comprises a plurality of light sources, each capable of generating an incident light beam having a different wavelength range. In one embodiment, for example, the optical monitoring system of the present invention comprises a combination of any of the following: white light source, red light source, green light source and blue light source. Use of a combination of light sources having different wavelength ranges is beneficial for discriminating and characterizing separated blood fractions because absorption constants and scattering coefficients of cellular and non-cellular components of blood vary with wavelength. For example, a red blood cell containing component is easily distinguished from platelet enriched plasma containing component by illumination with light having wavelengths selected over the range of about 500 nm to about 600 nm because the red blood cell component absorbs light over this wavelength significantly more strongly that the platelet enriched plasma containing component. In addition, use of multiple colored light sources for illumination provides a means of characterizing the white blood cell type in an extracted blood component. As different white blood cell types have different absorption and scattering cross sections at different wavelengths, monitoring transmitted and/or scattered light from a white cell-containing blood component provides a means of distinguishing the various white blood cell types in a blood component and quantifying the abundance of each cell-type.

Light sources of the present invention provide a continuous incident light beam or a pulsed incident light beam. Pulsed light sources are capable of being switched on and off in a manner synchronous with the rotation of the separation chamber to provide two dimensional distributions of transmitted and/or scattered light intensities corresponding to an observation region having a substantially fixed position using sensors, switches or other types of known cooperation. Alternatively, pulsed light sources of the present invention can be configured such that they can be switched on and off in a manner asynchronous with the rotation of the separation chamber providing two dimensional distributions of transmitted and/or scattered light intensities corresponding to different observation regions for each full rotation. This alternative embodiment provides a method of selectively adjusting the location of the observation region and, thereby, probing different regions of the separation chamber. In one embodiment, triggering of illumination pulses is based on the rotational speed of the centrifuge or can be based on the angular position of the separation chamber as detected by optical or electronic methods well known in the art. In a preferred embodiment, triggering is provided by trigger pulses generated by the centrifuge device controller and/or two-dimensional detector.

An illumination system of the present invention also includes one or more aperture plates capable of providing a selected illumination area on a blood processing device or component thereof. In a preferred embodiment, an aperture plate is positioned between the light source and the blood sample undergoing separation. In this embodiment, the aperture plate masks areas of the separation chamber where exposure to light causes unwanted scattered light. In some instances, the reduction of unwanted scattered light detected by the two-dimensional detector reduces noise and, therefore, improves signal to noise ratio and image quality. Aperture plates are typically integrated into a filler which holds the separation chamber in place during rotation. In this embodiment, the aperture plate rotates with the separation chamber. Optical filters and polarizers can also be incorporated into the illumination system of the present invention to provide illumination beams having selected optical properties, such as intensity, power, wavelength range and polarization state. Diffusers can also be incorporated into the illumination system of the present invention to provide spatially uniform illumination beams as is well known in the art.

Light collection elements of the present invention include any device capable of collecting and transmitting light in a manner generating a two dimensional distribution of transmitted and/or scattered light intensities of light from an observation region. Preferred light collection elements collecting and transmitting light in a manner generating a two dimensional distribution of transmitted and/or scattered light intensities comprising an image of the observation region. In an embodiment, the light collection element includes at least one fixed focus lens system. Alternatively, the light collection element includes at least one variable focal length lens system providing a selectively adjustable focal length, thereby, providing a selectively adjustable field of view. Light collection with a lens system providing an adjustable focal length provides monitoring systems wherein the size and shape of observation region can be selectively adjusted. In an exemplary embodiment, light collection elements of the present invention are capable of providing a field of view selectable over the range of about 1 cm$^2$ to about 10 cm$^2$. The ability to adjust the field of view provides optical monitoring systems wherein the resolution of the image generated can be changed and optimized for a given application or measurement.

Two-dimensional detectors of the present invention comprise any device or device component capable of detecting one or more patterns of light originating from a two-dimensional area or three-dimensional region. At the most fundamental level, two-dimensional detectors of the present invention comprise a plurality of discrete light detectors distributed over a two-dimensional area. In a preferred embodiment, a two-dimensional detector of the present invention is capable of measuring two-dimensional distributions of transmitted and/or scattered light intensities comprising high quality images. Reference to a high quality images in the present invention relates to the ability to generate with good reproducibility high resolution, preferably for some applications greater than 20 pixels per millimeter and more preferably for some applications greater than 50 pixels per millimeter, images of an observation region, which exhibit high signal to noise ratio, preferably for some applications greater than 10 and more preferably for some applications greater than 100. In one embodiment, image quality is optimized in the present invention by selective adjustment of the illumination intensities, detector exposure time, detector gain and the position of the light source, light collection element and detector.

In one embodiment, a two-dimensional detector of the present invention is capable of generating a monochrome image corresponding to the brightness of an observation region on a density centrifuge, or other blood processing device or device component. In an exemplary embodiment, the two-dimensional detector is capable of detecting light over the entire wavelength range used for illumination. Alternatively, detectors of the present invention further comprise one or more optical filters capable of transmitting light of a selected wavelength distribution and capable of preventing transmission of light having other wavelengths. Use of optical filtering is beneficial for decreasing the effect of unwanted background scattered light and differentiating and/or characterizing separated blood components. The present invention includes methods wherein imaging is provided using photo-sensitive films.

In one embodiment, two-dimensional detectors of the present invention are capable of generating a color image corresponding to an observation on a density centrifuge or other blood processing device. For example, color imaging is be useful for characterizing the extent of hemolysis during blood processing because hemoglobin has a strong, characteristic absorption over the wavelength range of 500 nm-600 nm. In addition, color imaging is be useful in determining the concentration of red blood cells or white blood cells in a separated and/or extracted blood component. In one embodiment, the two-dimensional detector of the present invention is capable of switching between color and monochrome imaging, preferably for some applications on a frame-to-frame basis.

Exemplary centrifuge separation chambers of the present invention are continuous flow through chambers or static, disposable chambers of a constant volume. Exemplary flow through separation chambers have an optical cell with one or more optical surfaces for transmitting light and can have one or more extraction ports for extracting a selected blood component. Optimally, extraction ports of the present invention reside close to or in the focal plane of the light collection element. Positioning of extraction ports in the focal plane is preferred because it improves measurement of the fluxes of cellular and noncellular material out of the separation chamber. Separation chambers of the present invention can include one or more dams positioned proximate to the extraction ports to facilitate selective extraction of separated blood components having reduced impurities arising from adjacent components. The use of dams in blood processing via density centrifugation is well known in the art and described in U.S. Pat. Nos. 6,053,856; 6,334,842 and 6,514,189.

Separation chambers of the present invention can further include one or more calibration markers for quantifying the absolute position of phase boundaries along the separation axis. Calibration markers are preferably located in the focal plane of the light collection element and can be any object or surface capable of easy recognition and characterization when imaged onto the two-dimensional detector. Use of a calibration marker can correct changes in optical alignment caused by rotation induced vibration and instrument jitter.

Calibration markers of the present invention facilitate image processing by enabling a computer algorithm to determine the precise location and physical dimensions of an observation region corresponding to a generated image or elements of an observation region. For example, calibration markers indicate the absolute position of phase boundaries between separated blood components in an observation region. Calibration markers also provide a means of establishing and maintaining correct focusing of the light collection element to ensure high quality images are obtained. Additionally, calibration markers also provide a means of calibrating the absolute brightness or color of pixels in a two dimensional image. In an exemplary embodiment, the calibration marker is the edge of the separation chamber or the edge of a filler device component which secures the separation chamber in place. Alternatively, the calibration marker is a series of bars having a known thickness, brightness and/or color.

Separation chambers usable in the present invention can be made from any material sufficiently transparent to allow efficient illumination of a sample undergoing centrifugation. Separation chambers useful for some applications comprise an optical cell having one or more optical surfaces for transmitting light. In a preferred embodiment, the separation chamber is made of a polymeric material such as polyvinylchloride. Preferred separation chambers have highly polished optical surfaces, such as windows capable of transmitting an illumination beam with great spatial uniformity. Separation chambers can also be flexible containers or annular disposable separation vessels.

In another embodiment of the present invention, the optical monitoring system includes a plurality of light collection elements and two-dimensional detectors. For example, in an exemplary embodiment, pairs of light collection elements and detectors are positioned to monitor different observation regions. Alternatively, pairs of light collection elements and detectors can be configured to detect light having different wavelength ranges originating from the same observation region.

In one embodiment, centrifugation device controllers of the present invention comprise a device or device component such as a computer or processor capable of receiving an output signal from the two-dimensional detector and affecting the separation conditions of the density centrifuge. In a preferred embodiment, centrifugation device controllers are capable of selective adjustment of the position of one or more phase boundaries along the separation axes. In one embodiment, for example, centrifugation device controllers of the present invention adjust the position of phase boundaries by varying the flow rates of one or more selected blood components out of the separation chamber. This can be achieved through the use of pumps, such as peristaltic pumps, to effectuate movement through tubing. Inlet pumps can be provided which are capable of forcing material out of the separation chamber. In another embodiment, the centrifugation device controller is capable of shutting down the centrifuge upon receiving a two-dimensional distribution of light intensities comprising a image indicating a leak of blood components out of the separation chamber, a misalignment of the separation chamber, a clot in the extraction ports or similar condition. In another embodiment, the centrifuge controller is capable of regulating the infusion of a blood agent, such as an anti-coagulating agent, to the blood sample undergoing processing. Alternatively, the centrifugation device controller comprises a means for controlling the pumping rate of material out of the separation chamber in a manner capable of blowing out clots in the extraction ports. For example, upon receiving an output signal corresponding to a two-dimensional distribution of light intensities comprising a image indicating a platelet clot in a plasma extraction port, a centrifuge device controller of the present invention is capable of automatically clearing the clot by lowering the red blood cell level by reducing the pumping rate of the plasma pump and then rapidly accelerating the pumping rate of the plasma pump to force the clot out of the extraction port. Alternatively, the centrifuge controller is be capable of selectively adjusting the rotational velocity of the centrifuge.

The optical monitoring system of the present invention can be integrated into a blood processing system, such as the systems described in U.S. Patent Ser. No. 5,653,887. In an embodiment, the monitoring system acts to provide the system controller with the information relevant to the blood processing or a therapeutic procedure in real time. A monitoring system of the present invention is capable of adjusting illumination and detection conditions necessary to achieve two-dimensional distributions of light intensities corresponding to the highest optical quality images. In one embodiment, the monitoring system is in two-way communication with the device controller and is capable of receiving input data defining a selected blood processing procedure or a patient undergoing treatment. Such data can included the purity of blood components to be separated and extracted, the identity of blood components to be collected, the identity of blood components to be returned to the patient, the amount of a particular blood component to be collected or any combination of these. Inlet fluid composition data can also be used to calculate other desired information such as predicted yields and anticipated time for a desired collection or process.

The present invention provides optical monitoring and control systems for blood processing devices, especially useful for processing blood via density centrifugation. As will be recognizable to those having skill in the art, all devices, device elements and device equivalents are within the scope of the present invention. The invention provides exemplary methods, devices and device components for monitoring and controlling the position of phase boundaries in a rotating separation chamber with improved sensitivity over conventional one-dimensional optical monitoring methods. In addition, the present invention provides multi-functional optical monitoring and control systems capable of monitoring and controlling diverse operating conditions of a density centrifuge. These and other variations of the present optical monitoring and control systems are within the spirit and scope of the claimed invention. Accordingly, it must be understood that the detailed description, embodiments, drawings and examples set forth here are intended as illustrative only and in no way represent any limitations on the scope of the invention.

All references cited in this application are hereby incorporated by reference in their entireties to the extent that they are not inconsistent with the disclosure in this application. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques specifically described herein are intended to be encompassed by this invention.

EXAMPLE 1

Monitoring the Position of Phase Boundaries Between Optically Differentiable Blood Components Undergoing Density Centrifugation The ability of the methods and devices of the present invention to monitor and control the position of phase boundaries between optically differentiable blood components was verified by experimental studies. Specifically, it is a goal of the present invention to provide optical monitoring and control systems capable of accurately measuring the position of one or more phase boundaries along the separation axes of a separation chamber of a density centrifuge blood processing apparatus. Further, it is a goal of the present invention to provide optical monitoring and control systems capable of selectively adjusting the position of one or more phase boundaries along the separation axis of a separation chamber to achieve optimal separation and extraction of blood components.

To achieve the aforementioned goals, two-dimensional distributions of transmitted and/or scattered light intensities comprising images of an optical cell containing human blood undergoing density centrifugation were measured for a variety of extraction flow conditions. The optical monitoring and control system evaluated comprises a light source, a close focus lens system, and a digital camera, arranged as illustrated in FIGS. 1 and 2. The light source is a combination of a xenon lamps and light emitting diodes which provides incident beams comprising white light which is directed through a windowed optical cell of the separation chamber. This configuration provided illumination of both the top and bottom of the windowed optical cell. The digital camera is an industry standard ⅓ inch DVT camera manufactured by DVT. The digital camera and lens set are positioned above the separation chamber such that phase boundaries between optically differentiable blood components are viewable as the optical cell is rotated into the observation region. Two dimensional distributions of transmitted and scattered light comprising two-dimensional color images were acquired upon every other rotation of the separation chamber. The illumination and detector configuration employed provided a horizontal field of view of approximately 32 mm, a vertical field of view of approximately 24 mm, a horizontal resolution of approximately 19.4 pixels mm$^{-1}$ and a vertical resolution of approximately 19.4 pixels mm$^{-1}$. As will be evident to a person of ordinary skill in the art, the exemplary optical components and configurations described above are but one means of generating, collecting and detecting patterns of light corresponding to a observation region and functionally equivalent lens and detector arrangements are intended to be within the scope of the present invention.

The centrifuge is equipped with a single stage separation chamber with an optical cell having a plurality of transmissive extraction ports. It is understood that the separation chamber could also be dual stage with extraction ports in different positions on separation chamber. Also the separation chamber could be formed of multiple chambers connected by tubing. As will be clear to one skilled in the art, other known centrifuge apparatus could be used. The separation chamber is also equipped with calibration markers for quantifying absolute phase boundary positions along the separation axes and for quantifying transmitted light intensities corresponding to separated blood components. The separation chamber is held in place by a circular filler which rotates about the central axis of the density centrifuge. The filler is also provided with calibration markers. The optical cell is equipped with three extraction ports, which terminate in the separation chamber at selected distances along the separation axis. The three extraction ports correspond to a plasma component, a buffy coat layer and a red blood cell component. First and second extraction ports corresponding to the plasma component and the buffy coat layer, respectively, are operationally connected to peristaltic pumps which are capable of establishing an extraction flow rate out of the separation chamber selected over the range of about 0.1 cm$^3$ m$^1$ to about 250 cm$^3$ m$^{-1}$. Peristaltic pumps connected to the density centrifuge are controlled by a computer, which is in two-way communication with the digital camera. Red blood cells exit the extraction port via a flow established by the centrifugal force and inlet pump.

Figure 6:
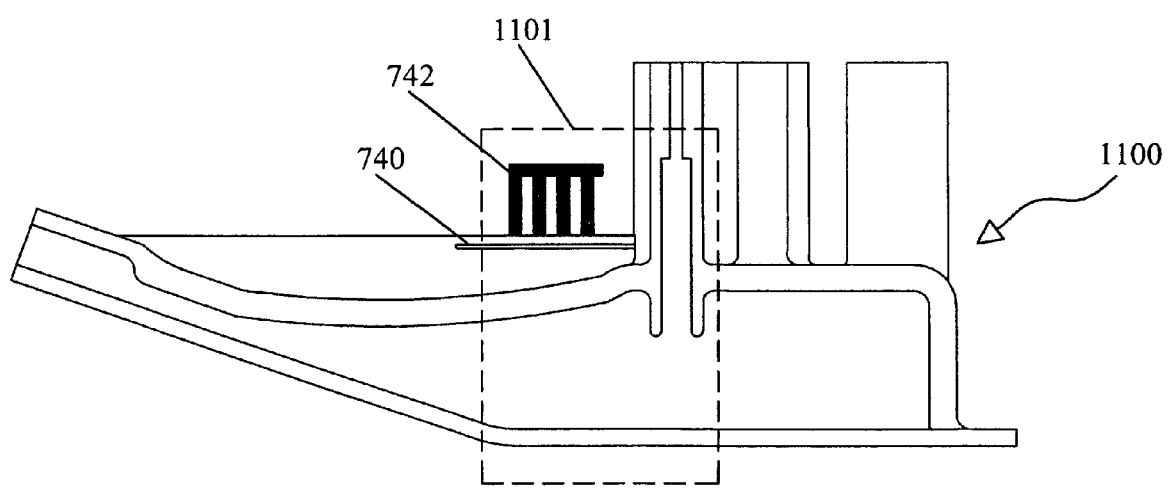
FIG. 6 is a top plan view of an optical cell of a separation chamber showing an expanded region illustrated in FIGS. 6A and 6B.
Figure 6A:
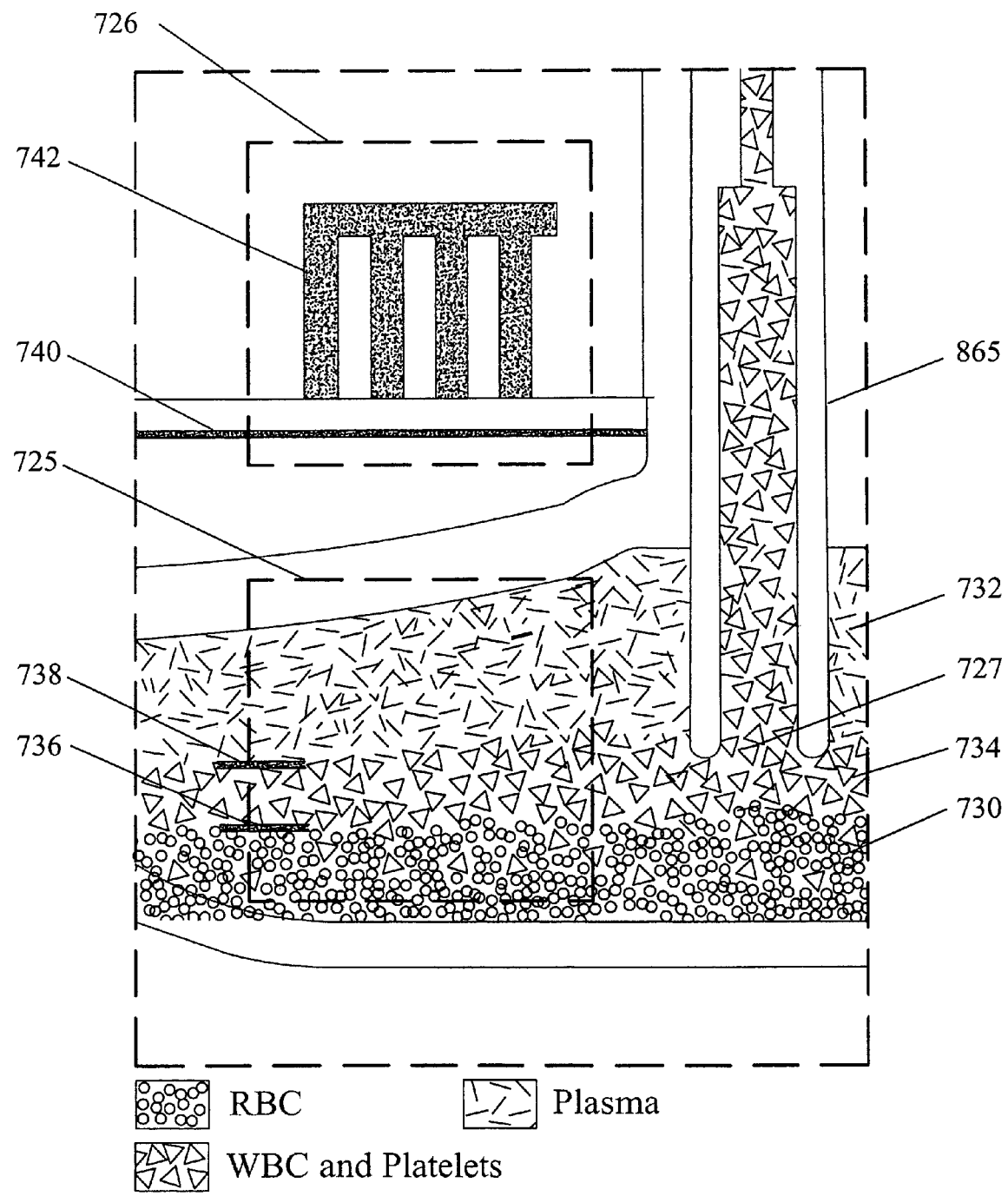
FIGS. 6A and 6B show schematics of images generated by the methods of the present invention of the expanded region shown in FIG. 6 having a human blood sample therein separated into blood components. The images in FIGS. 6A and 6B illustrate the ability of the methods and devices of the present invention to monitor and control the position of phase boundaries between separated blood components.
Figure 6B:
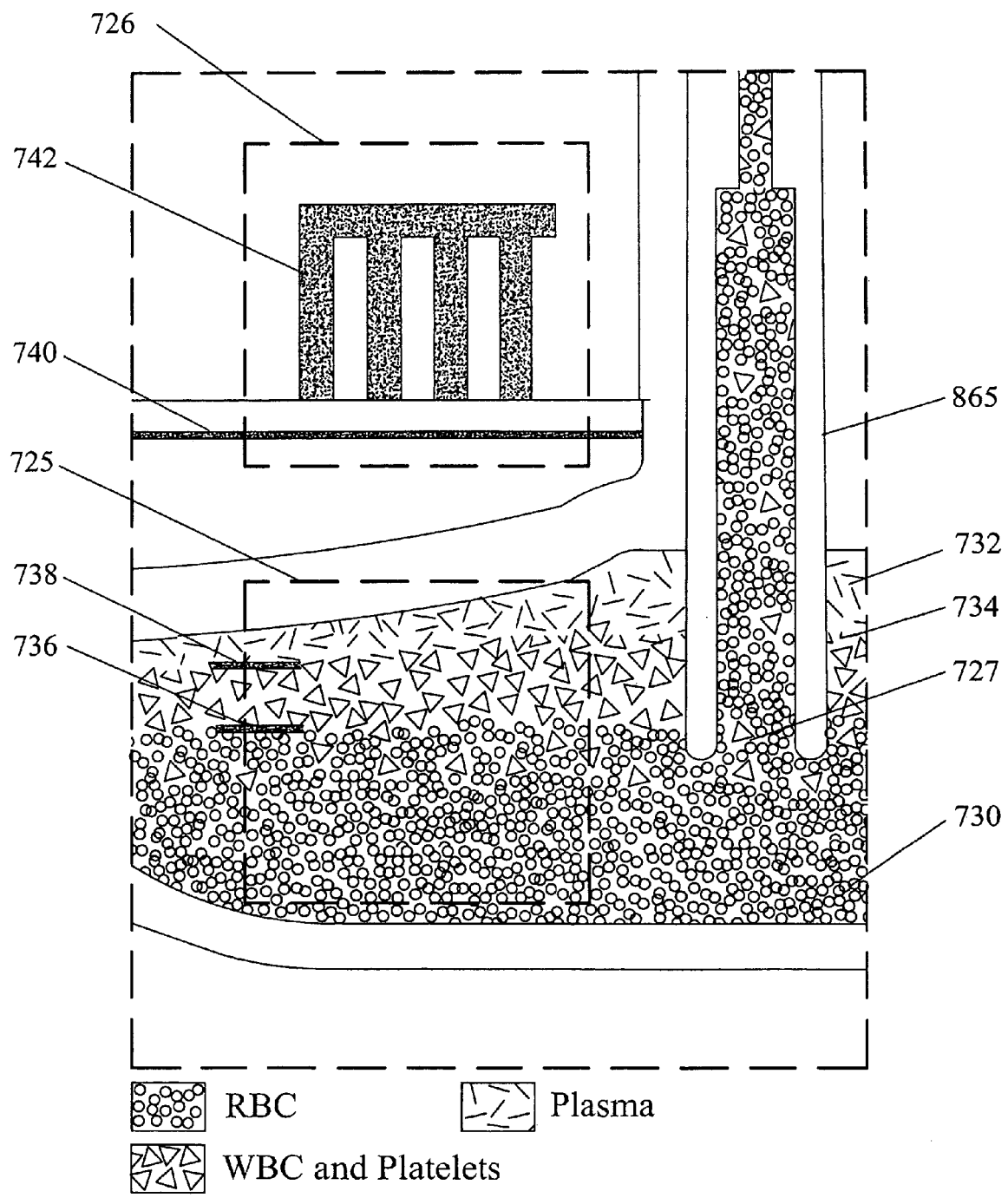

FIG. 6 is a top plan view of an optical cell 1100 of a separation chamber showing an expanded region 1101 illustrated in FIGS. 6A and 6B. FIG. 6A shows a schematic of an image generated by the methods of the present invention of expanded region 1101 having a human blood sample therein separated into blood components. The inlet flow rate of blood sample to the separation chamber was 75 ml min.$^{-1}$ and the flow rates of red blood cells and plasma components out of the separation chamber were 53 cm$^3$ min.$^{-1}$ and 20 cm$^3$ min.$^{-1}$, respectively. The image in FIG. 6A includes a phase boundary monitoring region 725, a calibration region 726 and extraction port 865 having orifice 727. Visible in the phase boundary monitoring region 725 are a red blood cell containing component 730, a plasma component 732 and a mixed phase buffy coat layer 734 having both white blood cells and platelets. A first stable phase boundary 736 between red blood containing component 730 and an buffy coat layer 734 and a second stable phase boundary 738 between the buffy coat layer 734 and a low density plasma component 732 are both viewable in phase boundary monitoring region 725. Visible in calibration region 726 is the first calibration marker comprising the edge 740 of the optical cell and a second calibration marker 742 comprising a series of bars 1 mm in thickness and having a known absorption and scattering characteristics. First and second calibration markers provide references for optimizing focusing of the light collection element, indicating the positions and physical dimensions of portions of the phase boundary monitoring region 725 and measuring the positions of phase boundaries between the red blood cell containing component, the buffy layer and the plasma component.

Analysis of the image in FIG. 6A was performed in real time and provided measurements of the position of first and second boundary layers. The average intensities of transmitted light corresponding to each blood component were also determined and analyzed with respect to the intensities of transmitted red light, green light and blue light. The position of first stable phase boundary 736 between red blood cell containing component 730 and an intermediate buffy coat layer 734 was determined to be 9.8±0.1 mm, relative to first calibration marker 740. The position of second stable phase boundary 738 between the buffy coat layer 734 and a low density plasma component 732 was determined to be 7.7±0.1 mm, relative to first calibration marker 740. Average transmitted light intensities corresponding to each blood component were determined using a 0-100 relative intensity scale for red light, green light and blue light components of the transmitted light wherein a value of 0 indicates no detected light and a value of 100 corresponds to transmitted light intensities which saturate the detector. The average transmitted light intensity levels of the red blood cell containing component 730 were determined to be 9, 7, and 8 for red light, green light and blue light components, respectively. The average transmitted light intensity levels of the buffy coat layer 734 were 26, 23 and 19 for red light, green light and blue light components, respectively. The average transmitted light intensity levels of the plasma component 732 were 63, 48 and 27 for red light, green light and blue light components, respectively.

FIG. 6B shows a schematic of an image of the separation chamber upon increasing the flow rate of the plasma component out of the separation chamber to equal 22 ml min.$^{-1}$ and decreasing the flow rate of the red blood cell containing component out of the separation chamber to equal 51 ml min.$^{-1}$. The inlet flow rate of blood sample to the separation chamber was held constant at 75 ml min.$^{-1}$. Analysis of the image in FIG. 6B was performed in real time and provided measurements of the position of first and second boundary layers and the average intensities of transmitted red light, green light and blue light for the modified flow conditions. The position of first stable phase boundary 736 between red blood containing component 730 and an intermediate buffy coat layer 734 was determined to be 9.2±0.1 mm, relative to first calibration marker 740. The position of second stable phase boundary 738 between the intermediate buffy coat layer 734 and a low density plasma component 732 was determined to be 7.4±0.1 mm, relative to the to first calibration marker 740. The average transmitted light intensity levels of the red blood cell containing component 730 were determined to be 11, 8, and 6 for red light, green light and blue light components, respectively. The average transmitted light intensity levels of the buffy coat layer 734 were 24, 20 and 17 for red light, green light and blue light components, respectively. The average transmitted light intensity levels of the plasma component 732 were 63, 46 and 27 for red light, green light and blue light components, respectively.

FIGS. 6A and 6B show that the present invention is capable of monitoring the position of phase boundaries between separated blood components in real time. In addition, a comparison of FIGS. 6A and 6B demonstrates that adjustment of the flow rate of one or more selected blood components out of the separation chamber results in a change in the positions of phase boundaries between separated blood components along the separation axes. Specifically, increasing the flow rate of the plasma component out of the separation chamber and decreasing the flow rate of the red blood cell containing component out of the separation chamber resulted in a shift of the position of the first phase boundary between the red blood cell containing component and the buffy coat layer toward the first calibration marker.

The images shown in FIGS. 6A and 6B illustrate the ability of the optical monitoring and control system to resolve the position of a plurality of phase boundaries between separated blood components. In addition, the images shown in FIGS. 6A and 6B also illustrate the ability of the optical monitoring and control system to adjust the flow rates of extracted blood components in a manner providing control over the position of phase boundaries between separated blood components. The ability of the monitoring and control system of the present invention to selectively adjust the position of phase boundaries between separated blood components allows phase boundary positions to be optimized to provide extracted components having a desired composition and purity. Specifically, the present invention provides a means of controlling the position of phase boundaries between optically differentiable components such that only a single blood component is proximate to the terminus of a selected extraction port.

EXAMPLE 2

Measurement of the Composition and Flux of Cellular Material Out of a Density Centrifuge.

It is a goal of the present invention to provide multifunctional optical monitoring systems capable of monitoring a plurality of operating conditions of a blood processing device. Specifically, it is a goal of the present invention to provide monitoring and control systems providing simultaneous measurements of phase boundary positions and the fluxes of cellular materials, such as white blood cells, platelets and red blood cells, out of a separation chamber of a density centrifuge. Further, it is a goal of the present invention to provide optical monitoring systems capable of characterizing the cell-type of material separated, extracted and collected. The ability of optical monitoring systems of the present invention to simultaneously monitor the position of phase boundaries in the separation chamber and the composition and flux of cellular blood components through an extraction port was verified by experimental studies.

Figure 7:
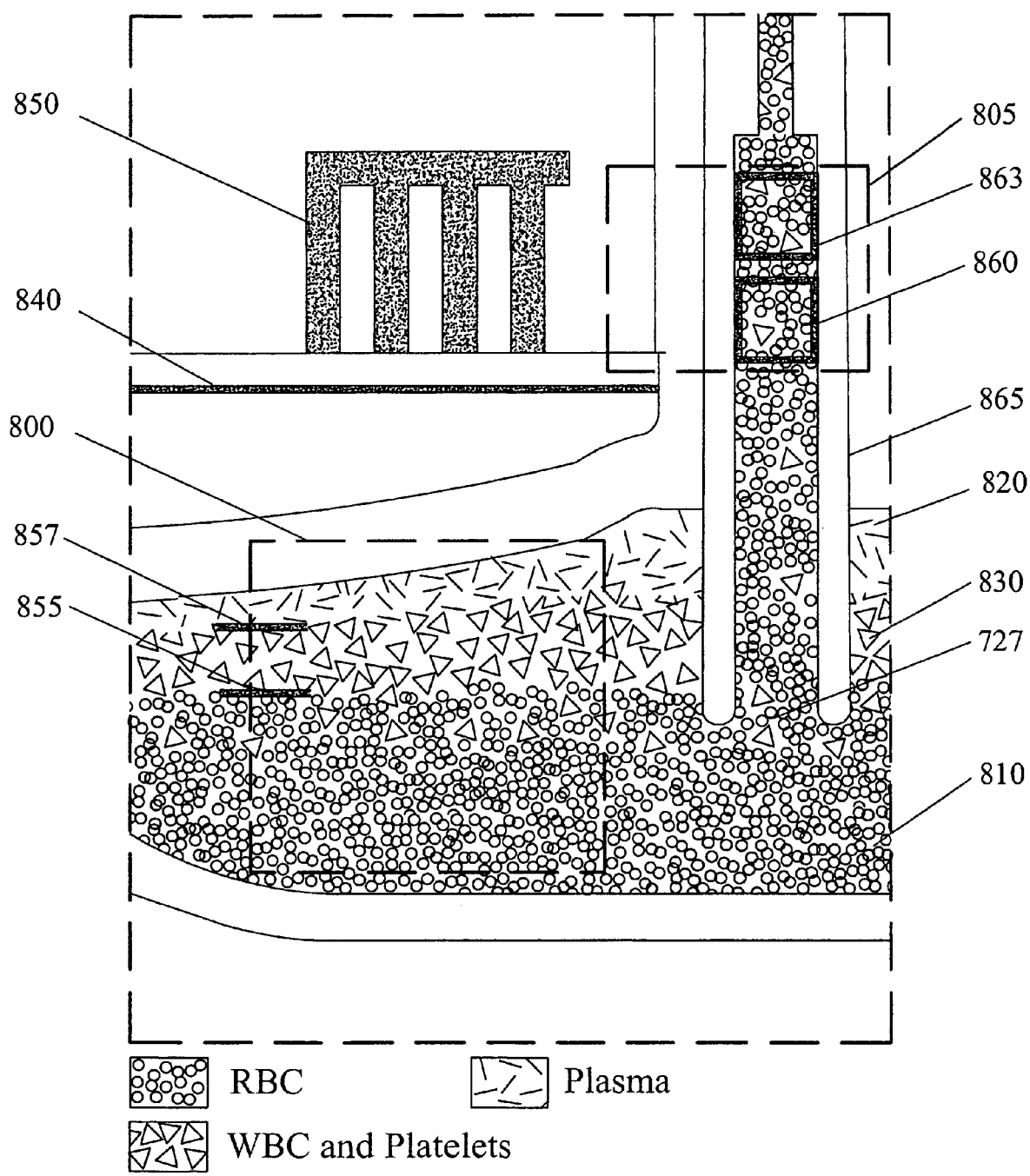
FIG. 7 shows images of the rotating separation chamber of a density centrifuge generated by the methods of the present invention. The image in FIG. 7 includes a phase boundary monitoring region and a white blood cell extraction port monitoring region. Analysis of the image in FIG. 7 provides a measurement of the composition and flux of cellular material out of the separation chamber.

To achieve the aforementioned goals, two-dimensional distributions of transmitted and scattered light intensities comprising two-dimensional images of separation and extraction regions of an optical cell of a rotating separation chamber in a density centrifuge were measured and analyzed in real time to provide simultaneous measurements of the positions of boundary layers between optically differentiable blood components and the compositions and fluxes of cellular materials out of the separation chamber. The optical monitoring and control system evaluated comprises a light source, a close focus lens system, and a digital camera, arranged as illustrated in FIGS. 1 and 2 and as described in Example 1. Illumination is provided by a light source positioned beneath the separation chamber which is capable of directing light through a white blood cell extraction port of the optical cell. Illumination is also provided to the top of the optical cell. Light transmitted through and scattered by the optical cell was collected by the close focus lens system and detected by the digital camera. Two dimensional distributions of transmitted and scattered light were acquired for every other rotation of the separation chamber at a rotational velocity of 1490 revolution min.$^{-1}$ FIG. 7 shows an image generated by the methods of the present invention corresponding to the separation of a human blood sample and extraction of a separated white blood cell-containing blood component. The image in FIG. 7 includes a phase boundary monitoring region 800 and a white blood cell extraction port monitoring region 805 of the optical cell. Visible in phase boundary monitoring region 800 are a red blood cell containing component 810, a plasma component 820 and a mixed phase buffy coat layer 830 having both white blood cells and platelets. Several calibration markers are also apparent in the image in FIG. 7. The edge 840 of the optical cell comprises a first calibration marker for determining the absolute position of phase boundaries between optically differentiable blood components. A series of bars 850 having a thickness of 1 mm and known scattering and absorption characteristics comprises a second calibration marker useful for optimizing the focusing of the light collection element and indicating the positions and physical dimensions of the phase boundary monitoring region 800 and the white blood cell extraction port monitoring region 805. Light intensities transmitted through the phase boundary monitoring region 800 were acquired as a function of time and analyzed in real time to provide measurements of the position of the phase boundary 855 between red blood cell component 810 and buffy coat layer 830 and the phase boundary 857 between the buffy coat layer 830 and plasma components 820. All boundary layer positions were measured relative to the edge of the optical cell 840.

White blood cell extraction port monitoring region 805 includes a first flux monitoring region 860 and a second flux monitoring region 863 positioned on white blood cell extraction port 865 of the optical cell. In this example, extraction port 865 having orifice 727 is configured to collect white blood cells in the human blood sample and extends a distance along the separation axis of such that it terminates proximate to the buffy coat layer in the rotating separation chamber. The two-dimensional distribution of light intensities of light transmitted through the first and second flux monitoring regions 860 and 863 depends on the concentration, and spatial distribution and cell-type of cellular material exiting the separation chamber. Light intensities transmitted through first and second flux monitoring regions 860 and 863 were acquired as a function of time and analyzed to characterize the composition and flux of cellular material out of the separation chamber. As cellular material, such as white blood cells and red blood cells, absorbs and scatters light from the light sources, passage of cellular material through the extraction port was observed to decrease the observed transmitted light intensities.

Figure 8:
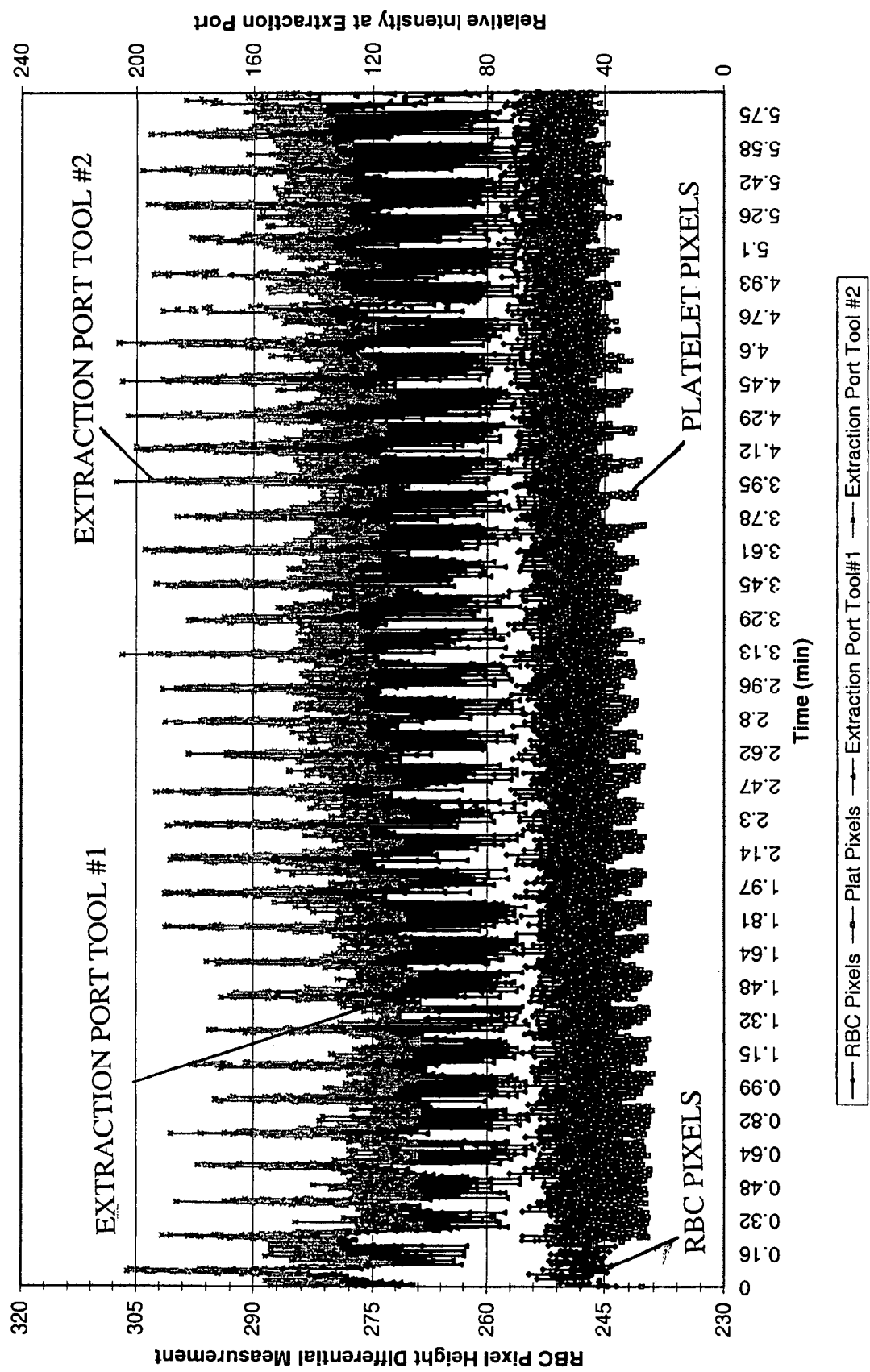
FIG. 8 shows the temporal behavior of the measured phase boundary positions (bottom two curves) and transmitted light intensities through the extraction port monitoring region (top two curves) during white blood cell collection.
Figure 8A:
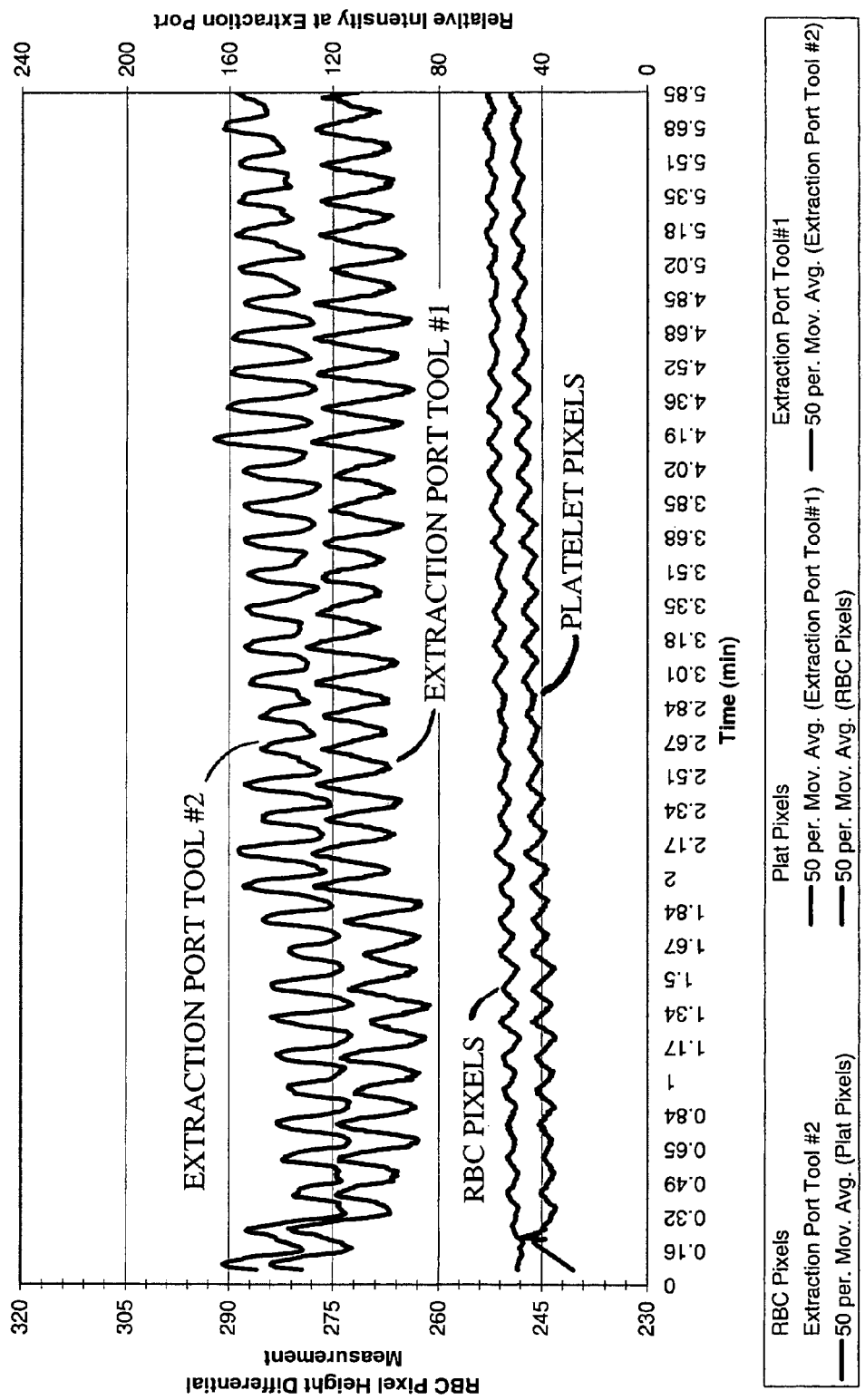
FIG. 8A show corresponding 50 point moving averages. Solid diamonds (designated as RBC Pixels) correspond to the position of the phase boundary between the red blood cell containing component and the buffy coat layer, open squares (designated as Platelet Pixels) correspond to the position of the phase boundary between the platelet containing component and the buffy coat layer, solid triangles (designated as Extraction Port Tool #1) correspond to median transmitted intensities through a first flux monitoring region and X markers (designated as Extraction Port Tool #2) correspond to median transmitted intensities through a second flux monitoring region.

FIG. 8 shows the temporal behavior of the phase boundary layer positions in the optical cell and transmitted light intensities through the extraction port monitoring region during white blood cell collection. The position of the phase boundary separating the red blood cell containing component 810 and the buffy coat layer 830 as a function of time is indicated by solid diamond markers (and designated as RBC Pixels in FIG. 8) and the position of the phase boundary separating buffy coat layer from the plasma layer as a function of time is indicated by open square markers (and designated as Platelet Pixels in FIG. 8). FIG. 8A shows 50-point moving averages corresponding to the position of the phase boundary separating the red blood cell containing component and the buffy coat layer (designated as RBC Pixels in FIG. 8A) and the position of the phase boundary separating buffy coat layer from the plasma layer (designated as Platelet Pixels in FIG. 8A) to better illustrate the temporal behavior of these parameters. As shown in FIGS. 8 and 8A, plots corresponding to the different phase boundaries do not intersect. This observation indicates that separation of the blood sample was maintained throughout extraction and collection. As shown in FIGS. 8 and 8A, plots corresponding to different boundary layers exhibit similar periodic behavior with maxima occurring at approximately the same times. The periodic nature of the plots shown in FIGS. 8 and 8A arises from the pumping characteristics of the peristaltic pumps and the surface tension of cellular material exiting the separation chamber.

A plot of the median transmitted intensities through the first flux monitoring region as a function of time is also shown in FIG. 8 as solid triangle markers (and designated as Extraction Port Tool #1 in FIGS. 8 and 8A) and a plot of the median transmitted intensities through the second flux monitoring region as a function of time is also shown in FIG. 8 as X markers (and designated as Extraction Port Tool #2 in FIGS. 8 and 8A). FIG. 8A shows the corresponding 50-point moving averages for first and second flux monitoring regions. Both plots of the median transmitted intensities exhibit periodic behavior similar to that shown in the phase boundary measurements. The correlation between the maxima and minima in each of the plots in FIGS. 8 and 8A suggests that the separation was effective and maintained throughout extraction and collection.

Figure 9:
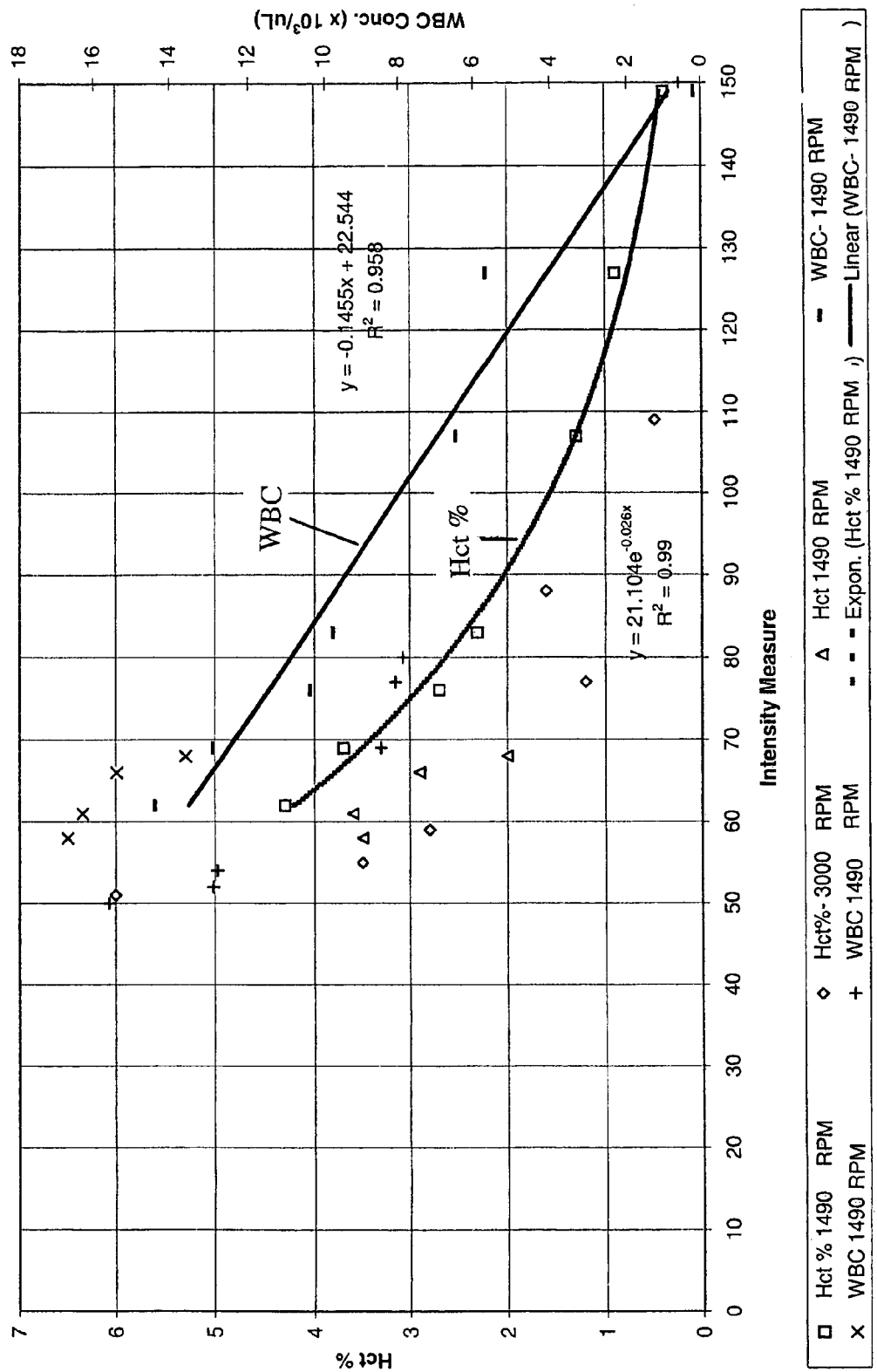
FIG. 9 shows a series of plots of the observed white blood cell concentrations as a function of the median intensity of light transmitted through the second flux monitoring region (X markers, + markers and − markers) corresponding to the rotational velocities (RPM) indicated in the legend. Also shown in FIG. 9, are plots of the hematocrit of the extracted material as a function of the median intensity of light transmitted through the second flux monitoring region (diamond markers, square markers and triangle markers) corresponding to the rotational velocities (RPM) indicated in the legend.

Integration of the plots in FIG. 8 of the median transmitted intensities through the first and second flux monitoring regions as a function of time provides a measurement of the net amount of cellular material collected during the extraction period. To verify this aspect of the present invention, aliquots of blood components passing through the white blood cell extraction port were analyzed to provide complementary measurements of the composition of the extracted material. Aliquots of extracted material were collected over 3 minute sampling intervals and were subsequently analyzed using flow cytometry methods well known in the art. FIG. 9 shows a series of plots (X markers, + markers and − markers) of the observed white blood cell concentrations as a function of the median intensity of light transmitted through the second flux monitoring region. As shown in FIG. 9, the concentration of white blood cells collected for a given aliquot is inversely correlated to the observed median transmitted light intensity. The inverse correlation in FIG. 9 provides an experimental verification that methods of the present invention provides real time measurements of the cellular composition of material extracted from the separation chamber. Also shown in FIG. 9, are plots (diamond markers, square markers and triangle markers) of the hematocrit of the extracted material as a function of the median intensity of light transmitted through the second flux monitoring region.

Figure 10:
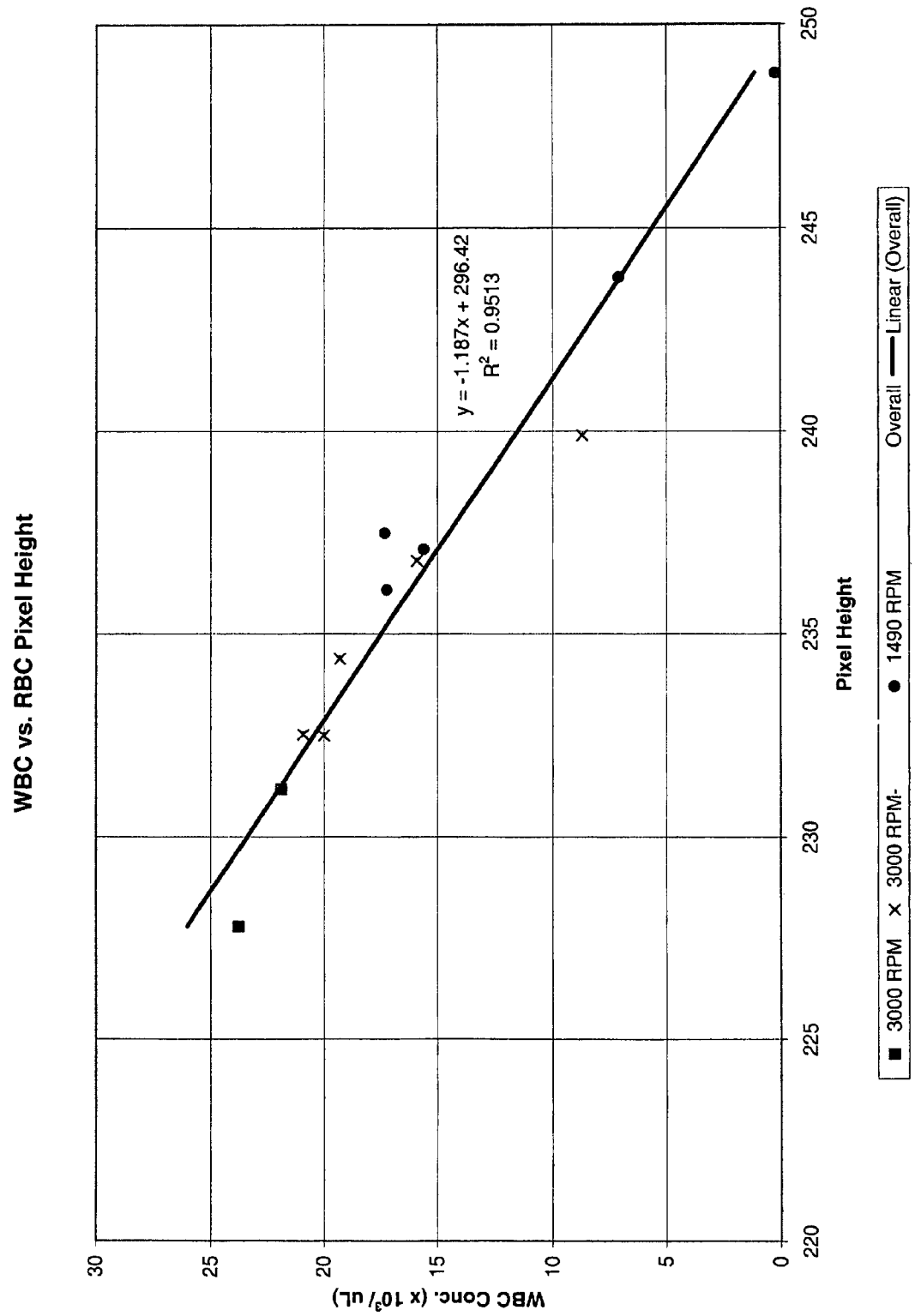
FIG. 10 shows a plot of the concentration of white blood cells in the extracted material as a function of the position of the phase boundary (in terms of pixel height of the collected image) between the red blood cell containing component and the buffy coat layer corresponding to the rotational velocities (RPM) indicated in the legend.

FIG. 10 shows a plot of the concentration of white blood cells in the extracted material as a function of the position of the phase boundary between the red blood cell containing component and the buffy coat layer for the rotational velocities (RPM) indicated in the legend. The linear relationship shown in FIG. 10, provides a useful index to allow the operator of the monitoring and control system to set the phase boundary between the red blood cell containing component and the buffy coat layer in a manner providing a desired concentration of extracted white blood cells.

EXAMPLE 3

Methods of Real-Time Image Processing and Device Control

The present invention also includes a variety of methods for processing data from an optical monitoring system corresponding to two dimensional distributions of transmitted and/or scattered light intensities to provide real time measurements of important operating parameters. Methods of organizing, processing and analyzing optical data are used in the present invention to generate input signals useful for monitoring and controlling blood processing. The present invention includes several computational approaches to managing and synchronizing data acquisition, data analysis and device control processes.

A. Master-Smart Slave Process Control System for Controlling Blood Processing.

Using computer science terminology for information transfer, a process control system of the present invention can be conceptualized as a data "Client" as it requests specific information from the optical robot/smart sensor. Similarly, the optical robot/smart sensor can be conceptualized as a data "Server" as it provides the specific information that the process control system requests. Therefore, the present invention includes certain aspects of a "Client/Server" design. Using engineering terminology for command and control, the process control system can be conceptualized as a "Master" component since it commands the optical robot/smart sensor, and the optical robot/smart sensor can be conceptualized as a "Slave" component since it responds to process control system commands.

In one aspect, the present invention provides a blood processing controller having a master-smart slave process control system, which is particularly useful for providing automated control of a blood processing device or a blood processing procedure. Use of the term "master-smart slave control system" in the present invention refers to a hardware and software architecture wherein a master Procedure Control system generates control signals requesting specific information from a smart slave data acquisition and analysis system. A smart slave data acquisition and analysis system of the present invention is capable of performing measurements to ascertain information requested from the master Procedure Control system. Furthermore, a smart slave data acquisition and analysis system of the present invention is also capable of optimizing measurement conditions to achieve the best information to return to the master Procedure Control system. At any time during the procedure, however, the master Procedure Control system can switch modes and command the smart slave data acquisition and analysis system to examine a different set of parameters. This ability to dynamically change what area or parameters are being monitored, utilizing different reference points and delivering different examination sets, is beneficial because it provides better error detection and device management.

A primary advantage of the master-smart slave process control system of the present invention is that it provides the ability to extract and analyze optical measurements of important operating parameters of a blood processing device on a very short time scale, preferably on a time scale of less than about 50 milliseconds. Exemplary data analysis methods of the present invention provide control systems capable of correlating a plurality of measurements in real time to provide the best measurement of the composition of blood sample undergoing processing and/or to optimize a selected blood processing procedure. In addition, data analysis methods of the present invention also include predictive data analysis algorithms capable of monitoring trends in important measurements in real time which enables the process control system to respond to changes in blood processing conditions or sample composition quickly. Furthermore, data analysis methods of the present invention are capable of evaluating uncertainties in optical measurements in real time, which provides an important index for product validation and quality control assessments.

Figure 11:
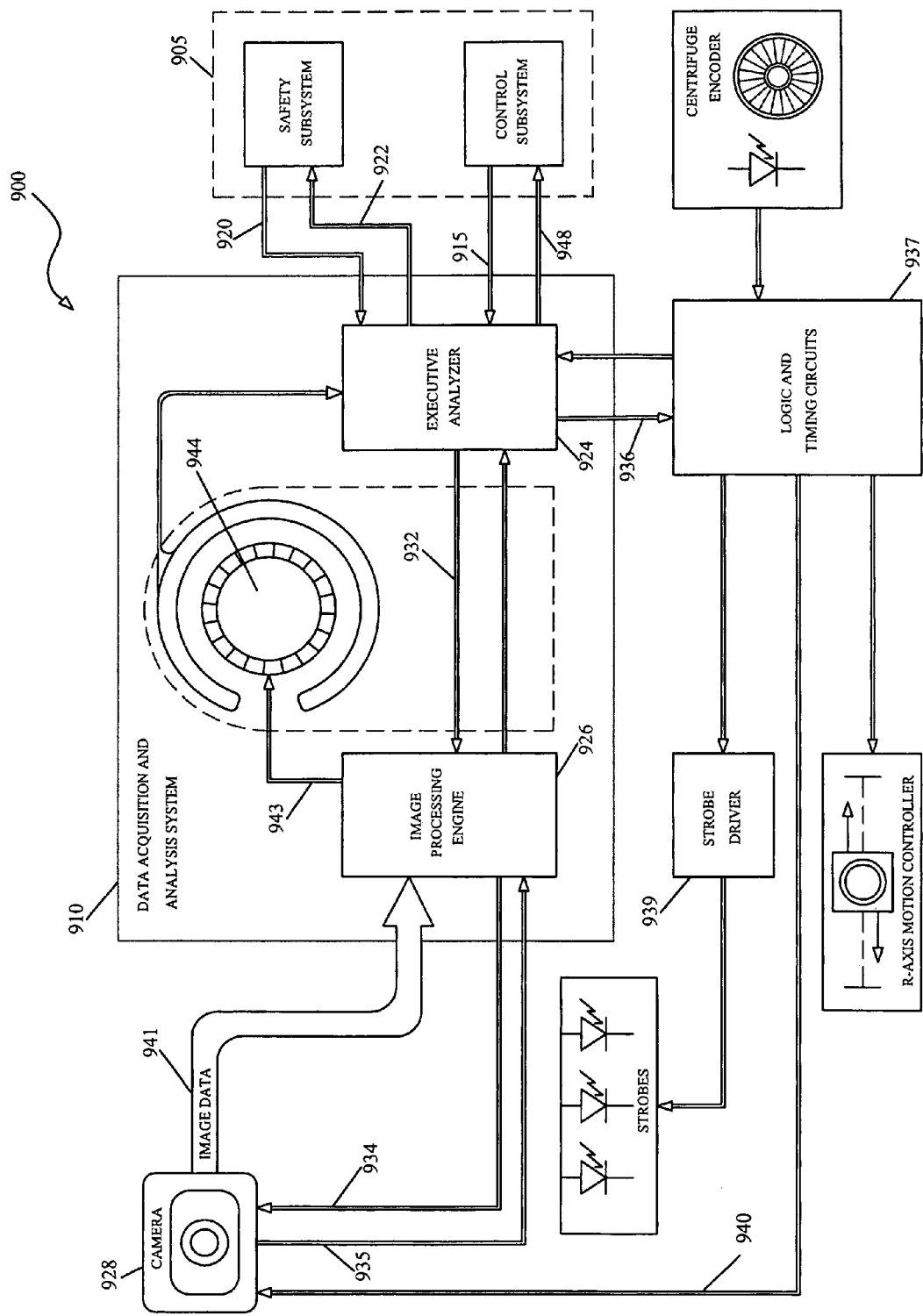
FIG. 11 shows a schematic of an exemplary master-smart slave control system of the present invention capable of controlling blood processing.

FIG. 11 shows a schematic of an exemplary master-smart slave process control system of the present invention capable of controlling blood processing. The exemplary control system 900 illustrated in FIG. 11 comprises master Procedure Control system 905 in two way communication with a smart slave data acquisition and analysis system 910. Master Procedure Control system 905 is capable of receiving input signals corresponding to a selected blood processing procedure, a sample undergoing processing and/or a patient undergoing treatment. Based on these input signals, master Procedure Control system 905 generates and transmits procedure requests and procedure commands 915 to the smart slave data acquisition and analysis system 910. In a preferred embodiment, master Procedure Control system 905 also generates and transmits a series of test commands 920 to smart slave data acquisition and analysis system 910. Smart slave data acquisition and analysis system 910 is capable of receiving test commands 920 and generating test response signals 922 which verify that control system 900 is fully functional and that the patient or blood sample identified by the smart slave data acquisition and analysis system 910 is correctly associated with the selected blood processing procedure or therapy.

Smart slave data acquisition and analysis system 910 has a distributed processing architecture and comprises a first computer processor 924 in two-way communication with a second computer processor 926. First computer processor 924 is configured to receive procedure requests and procedure commands 915 from master Procedure Control system 905 and transmit processing commands 932 to second computer processor 926. Second computer processor 926 analyzes the processing commands 932 and transmits camera setting commands 934 to the CCD camera and light collection element 928 which provide information related to establishing the proper exposure time, camera and light collection element position, field of view, color or monochrome imaging and other parameters necessary for acquiring high quality images of the blood processing device. First computer processor 924 is also configured to transmit illumination control and triggering commands 936 to light source and camera triggering hardware 937. Using centrifuge positional encoder data, triggering hardware 937 transmits electronic trigger signals to the light source driver circuits 936 and camera trigger 940. Camera and light collection element 928 measure two dimensional distributions of transmitted and/or scattered light intensities comprising images of an observation region on a blood processing device or blood sample undergoing processing. The raw image data is transmitted to the second computer processor 926 for image formatting and real time image processing. In an exemplary embodiment wherein the process control system is operationally connected to a density centrifuge, an image is acquired upon every other rotation of the separation chamber. For a rotational velocity of 3000 rotations per minute, this corresponds to acquisition of an image every 40 milliseconds.

The formatted image data is operated on by second computer processor 926 using one or more image-processing algorithms, each of which correspond to a different desired measurement or plurality of measurements. Image-processing algorithms extract measurements from the image data and determine critical and salient information about physical and chemical characteristics of the blood components undergoing processing and the operation of the blood processing device itself. Image-processing algorithms examine and quantify the image data in both the spatial and frequency domains. Image-processing methods include the following industry standard techniques: 2D-convolutions, 2D-transforms, histograms, thresholding, edge/line detection, segmentation, mensuration, morphological filters, spatial filters, frequency domain filters, nonlinear filters, adaptive filters, bayesian filters, graphics and color image processing algorithms. Operation of an image-processing algorithm on the formatted image data generates numerical measurement data 943, which is used to populate data fields of derived image objects. Therefore, at least one image data object is created every time new image data is received by the image data acquisition algorithms. In addition, a corresponding time stamp is be fed in to the image data object upon its instantiation. Time stamp information is used to track the rotational velocities of the centrifuge and to generate sampling rate information utilized in calculating velocity and acceleration values for the parameters of interest. Additional time stamps can be assigned to image data objects corresponding to different states in the data acquisition, analysis and handling process. It is important to note, however, that the image data object does not contain the actual graphical image data. Rather, the image data object contains one or more measurements extracted by operation of the image-processing algorithms.

Immediately after creation of a new image data object, it is placed onto a linked list of image data objects designated as the image data list 944. This list stores and enqueues image data information backwards in time. For an acquisition rate of 25 frames per second, 25 image data objects are inserted onto the image data list every second. Maintaining an image data list limited to a finite set of image data objects is beneficial because it prevents over-consumption of the system memory and avoids system failure due to over-consumption of computational resources. Therefore, the image data list acts as a managed circular buffer by deleting the oldest image data off the tail end of the list while inserting newly acquired image date at the head of the list. In an exemplary embodiment, a cooperative list manager algorithm manages the storage and removal of image data objects in the image data list. Importantly, an input-output bottleneck is avoided by using the dual processor design of the present invention because the image data objects are stored in memory and periodically examined by the first computer processor 924. This aspect of the process control system allows data processing, analysis and evaluation on a very short time scale, preferably for some applications less than 50 milliseconds.

Image data objects in the image data list are periodically examined by the first computer processor 924 and provide key data sets for monitoring and controlling blood processing. First computer processor 924 operates on image date objects in the image data list using multiple-image-data object analysis and evaluation algorithms. For example, applied image-data analysis algorithms can evaluate a single image data object or a short series of image data objects to determine the resolution of the acquired image, the brightness levels of an acquired image, the field of view of the observation area or other aspects of the monitoring and control system. Measurements generated from the operation of the image-data analysis algorithms establish the basis of image information output signals 948 sent to the master Procedure Control system 905. Image information output signals provide information requested by the master Procedure Control system 905. For example, information output signals 948 can be related to the purity of extracted blood components or the amount of collected materials. Image information output signals can also provide alarm signals indicating that the blood processing system or image processing system is not working as expected or indicating a rapid change in the composition of the blood sample undergoing processing.

Measurements generated from the operation of the image-data analysis algorithms and process control algorithms also serve as the basis of output signals sent to the camera and light collection element 928, light source and camera triggering hardware 937 to optimize the quality of the images acquired an analyzed. For example, output signals can adjust in the intensity of the illumination beam, change the color of the illumination beam, or adjust the camera's gain or exposure time. In this manner, smart slave data acquisition and analysis system 910 acts as a smart sensor capable of dynamically optimizing the quality of the measurements requested by the master Procedure Control system 905.

In one embodiment, list manager algorithms communicate with process control and image data analysis algorithms to determine how long the link-list should be. The list manager algorithms can also manage simultaneous access to the list by utilizing either mutexes, semaphores or critical sections. This is an important feature since the algorithms inserting image data objects onto the list and those reading a series of frames of image data objects are generally asynchronous multiple threads.

In an exemplary embodiment, first computer processor 924 operates on the image data list using predictive image data analysis algorithms to examine one or more trends in the image data parameters. The specific predictive algorithms read the object data list periodically, examine a series of image data objects acquired during a given time interval and analyze the series for changes in a plurality of selected parameters of interest. For example, a specific predictive control algorithm can examine changes in the position of a phase boundary along the separation axis and/or the composition of a blood component exiting the separation chamber. In an exemplary embodiment, a predictive image data analysis algorithm analyzes the object data list every time a new image is acquired and the object data list is then analyzed as pair of chronologically ordered frames for the purpose of comparative analysis. These frames are denoted as current frame and previous frame. The current frame contains the most recently acquired image data object, and a specified number chronologically ordered data objects that immediately preceded the most recently acquired data object. The previous frame contains a matching number of chronologically ordered image data objects, starting with the image data object sequenced immediately before the oldest image data object in the current frame. Predictive image data analysis algorithms compare and correlate a plurality of parameters from the two frames to derive positional, directional, characteristic, and associated rates of change information relating to the desired extracted image data information. Discrete magnitudes of changes in a plurality of parameters as a function of corresponding discrete time intervals are used to derive velocity and acceleration information for the specific parameters of interest. This rate information, along with specific associated positional or quantitative characteristic data is used to generate Image Information data packets 948 sent to the master Procedure Control system 905. In an exemplary embodiment, master Procedure Control system 905 uses the Image Information data sent on a periodic basis by first computer processor 924 along with discrete extraction pump flow data as inputs to a discrete data closed loop transfer function. In turn, the output values of the discrete data transfer functions are used to automatically manipulate the operating conditions of the centrifuge, such as plasma flow rate out of the separation chamber, rotational velocity, collect flow rates.

The primary goal of the image processing and control systems of the present invention is to provide automatic tracking and maintenance of optimal separation conditions for a particular blood processing application or therapy. For example, a exemplary data processing system is designed to maximize the efficiency of white blood cell collection by allowing the system to skim off the specific, desired types of cells, while minimizing contamination by collecting unwanted cell types. A significant advantage of the automated data processing methods of the present invention is that they free up time of the nurse or physician operating the blood processing apparatus to concentrate on patient care. In addition, the automated data processing methods of the present invention improves consistency and quality of the collected blood components.

In one embodiment, the data processing methods of the present invention are capable of monitoring and tracking the position of the phase boundary between red blood cells and less dense blood components along the separation axis. In an exemplary embodiment, a predetermined control value can be established, wherein the measured position of the phase boundaries exceeds the predetermined control value, a signal is generated which rapidly de-accelerates the plasma flow rate in a manner capable of restoring the red blood cell level to below the control value.

In another preferred embodiment, the data processing methods of the present invention characterize and track the cells flowing up and out of a given extraction port. In this method images corresponding to one or more extraction port are acquired and processed provide real time measurements of the number and cell-type of cellular material exciting the separation chamber.

A key advantage of the optical monitoring system and data processing method of the present invention is that a plurality of key operating parameters are simultaneously monitored and dynamic adjustments based on the combination of these measurements can be made in real time. Artificial intelligence algorithms can take the data generated and utilize it in a dynamic multi-variable decision making matrix. Importantly, the system perform different correlations on the different data sets to optimize and manage a blood component collection process and quality of the blood components collected. For example, in an exemplary embodiment, the red blood cell level and collected blood component concentration are concurrently examined using the methods of the present invention. The combination of both measurements provides a description of the blood processing process far more complete than conventional systems for controlling blood processing. For example, detection of an acceptable red blood cell level in the separation chamber and a very low concentration of collect red blood cells can be indicative of the presence of a clot in the red blood cell extraction port. Therefore, upon observing this combination of measurements, an output signal can be generated which reduces the plasma pump and then rapidly accelerated the plasma and collect pumps to blow the clot out of the extraction port.

In another embodiment, the thickness of a buffy coat layer comprising white blood cells is monitored in real time. As white blood cells are removed from the blood sample, the buffy coat layer gets thinner and thinner, thereby change the position of phase boundaries relative to the inlet of an extraction port. The ability of the present invention to track these changes in real time allows for better collection and higher purity of the removed white blood cell fraction. For example, statistical models can be applied to adjust the control value associate with the position of the phase boundary between a red blood cell component and a buffy coat layer to optimize collection of white blood cells while minimizing the unwanted collection of red blood cells.

In a preferred embodiment, the smart slave data acquisition and analysis system serves as a slave robot to the master Procedure Control system. The master Procedure Control system selects a specific therapeutic procedure that an operator has requested. Next, the master Procedure Control system loads the corresponding software module for that procedure and starts the procedure. At this time the specific procedure will establish communication with the smart slave data acquisition and analysis system. Then the procedure within the master Procedure Control system will query the smart slave data acquisition and analysis system and determine if it has an imaging procedure algorithm that is a suitable match for the therapeutic procedure loaded into the master Procedure Control system. If a suitable match is found, then the master Procedure Control system will command the smart slave data acquisition and analysis system to load the appropriate software module and start running it. Once the therapeutic procedure in master Procedure Control system links up with the imaging procedure in the smart slave data acquisition and analysis system, it will command the imaging procedure to go into the specific monitoring and data analysis routines associated with the specific procedure. The master Procedure Control system will also command the smart slave data acquisition and analysis system to report back image information and data packets at a pre-configured periodic rate. The image information and data packets contain critical information pertaining to control parameters relevant to the specific procedure. The master Procedure Control system can utilize image data information as long as necessary for certain measurement.

B. Partially Distributed Software Executed Methods for Controlling Blood Processing.

The present invention provides software executed methods for monitoring and controlling blood processing via density centrifugation. Methods of the present invention include fully automated control systems comprising a partially distributed software system running on a single processor or multiprocessor computing system. Exemplary methods of the present invention optimize the amount of information extracted from one or more two dimensional distributions of transmitted and/or scattered light intensities comprising images of a blood processing device or device component. In addition these methods provide real time data analysis, error detection and device control based on a plurality of predictive system control algorithms. The ability of methods of the present invention to effectively analyze large amounts of optical data and selectively adjust operating conditions in real time is particularly beneficial for processing blood samples exhibiting a highly variable compositions, such as those commonly encountered in patients undergoing therapy, and therapeutic applications wherein significant changes in a patient's blood composition commonly occur during processing.

3B(i). Control System Overview

Figure 12:
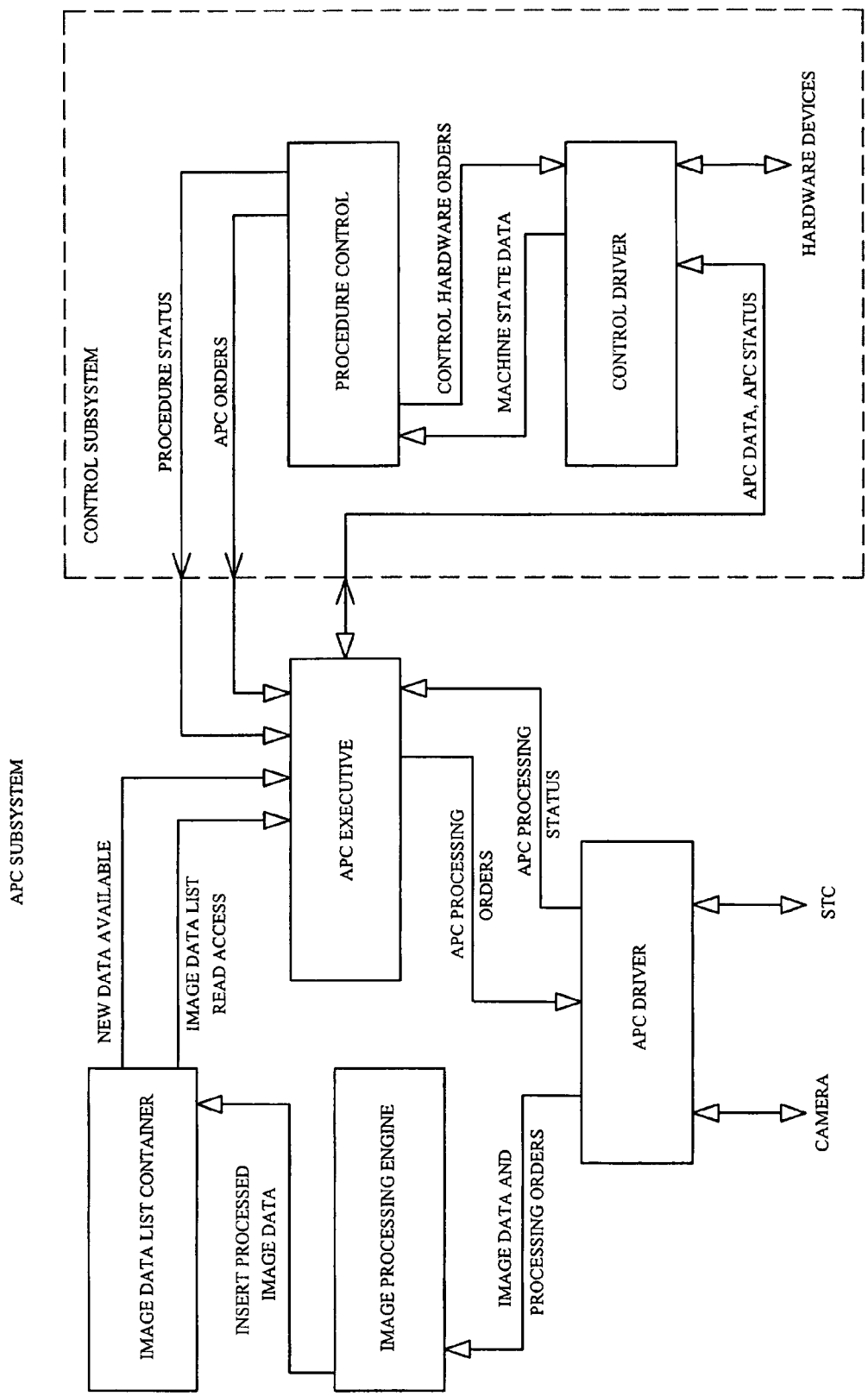
FIG. 12 provides a schematic flow diagram illustrating an automated, computer controlled process control system for a density centrifuge blood processing device.

FIG. 12 provides a schematic flow diagram illustrating an automated, computer controlled process control system for a density centrifuge blood processing device. The illustrated process control system is a digital imaging based smart sensor that monitors blood component processing within a separation chamber of a density centrifuge. The overview provided in FIG. 12 indicates major software components and important data paths of the process control system useful for providing device monitoring and control in real time.

The illustrated process control system comprises a Control Subsystem and an Automated Process Control (APC) Sub-System. As the process control system employs a software architecture having some components that are executed on a Control Sub-System, it can be conceptualized as a partially distributed software model. Use of a partially distributed software model in the present invention is preferred for some applications because it provides an efficient way of acquiring, processing, analyzing and using large amounts of image data.

The physical boundary between the APC Sub-System and the Control Sub-System is indicated by the dashed line in FIG. 12. Additional device components are also indicated in FIG. 12, such as the digital camera and synchronization timing controller (STC), to illustrate how elements of the process control system are interfaced with additional device components useful in the methods and devices of the present invention. These additional device components can be viewed as stand alone elements in communication with the process control system or as integral parts of the APC Sub-System. For example, the digital camera and STC can comprise embedded type (firmware-based) micro-controllers that are controlled and monitored through the APC Driver component of the APC Sub-System.

Referring again to FIG. 12, there are two main data loops within the process control system software architecture. First, an Image Analysis Loop is provided which is contained completely within the APC Sub-System. This data loop is responsible for acquisition, processing and analysis of image data provided by a CCD camera in optical communication with a density centrifuge blood separation device. Second, a Control Loop is provided which is distributed between the APC sub-system and the Control Sub-Systems. This data loop is responsible for using the analyzed image data to control and optimize a procedure running on a blood processing system.

In the Image Analysis Loop, the APC Executive determines the type of image analysis to be performed, and sends APC processing orders to the APC Driver. These processing orders contain selected information including, but not limited to, camera exposure settings, STC trigger settings, and image processing orders for the sequence of one or more images required for a selected analysis. In one embodiment, once a set of orders is sent to the APC Driver, it will normally continuously execute the orders until another set of orders is received. The APC Driver provides key hardware components with initialization and command information which appropriately prepares the hardware for the acquisition of a desired image or plurality of images. The APC Driver then receives the resulting image data and forwards this data along with a copy of the STC and camera settings, and the image processing orders to the Image Processing Engine. Packaging by annotating the image data with complementary command and device setting data allows the APC Driver to handle all of the time-critical operations required to synchronize the image data with settings used to generate the image and the orders necessary to process the image. In addition, packaging in this manner eliminates requirements for tight time-coupling among the other APC software and hardware components. The Image Processing Engine performs the requested operations for each image, and inserts analyzed data for each image frame into a Image Data List Container. The processing provided by the Image Processing Engine effectively reduces the large amount of data contained in the image itself to a small set of measured parameters. The APC Executive obtains the analyzed data from the Image Data List Container and copies this data into local buffers as necessary, allowing it to perform analysis operations requiring multiple frames of data. This aspect of the invention allows trends in several frames of data to be extracted and used as input in important predictive device control algorithms.

In regard to the Image Analysis Loop, it is important to note that listing the operations in this order does not imply that a single image frame is processed to completion, and only then is the next frame started. Rather, each step runs concurrently, allowing higher image throughput rates. This functional capability of the present control system can be conceptualized as operation of a computation pipeline capable of performing a large number of independent computations on different data sets. For example, while the Image Processing Engine is busy analyzing one image, the APC Driver can be reading the data for the next image from the camera and preparing the next data packet for the image processing engine.

In the Control Loop, The APC Executive sends analyzed image data and status to the Control Driver. The Control Driver uses the image data to determine appropriate operating setting of the density centrifuge including but not limited to, inlet and extraction pump flow rates, valve positions, and rotational velocity of the density centrifuge. The Control Driver also makes this status available to Procedure Control through the Machine State Data. Procedure Control uses information on the current procedure as well as APC status information and data to determine one or more APC orders, and to adjust parameters used by the Control Driver. The APC Executive receives orders and procedure status from Procedure Control, and uses this information to determine the appropriate APC processing orders for a selected blood processing procedure or device configuration.

To further illustrate the capabilities of the present control system and not intending to imply any limitations on its design and uses, an example is presented below to further clarify the operations of the process control system of the present invention. For this example, the APC Sub-System is in steady-state measurement mode for a mononuclear cell (MNC) collection. Upon first entering this mode, the APC Executive writes the orders for the frame sequence required and the APC Driver will repeat the sequence until ordered otherwise. Assuming that the APC Executive has ordered a series of eleven image frames corresponding to two dimensional distributions of transmitted or scattered light intensities to be collected. The first ten frames specify measuring the red-cell interface position and optical density of the fluid in an extraction port corresponding to a collection port. The final frame specifies a somewhat more lengthy image analysis, intended to monitor image data relating to the quality of the images being collected, and thus relating to the reliability of the measurements collected in the other frames.

In this example, the APC Driver collects each of the frames in sequence, forwarding image data and image processing orders to the Image Processing Engine. The Image Processing Engine analyzes each of the frames and places the analyzed data for each image frame in the Image Data List Container. The APC Executive receives the analyzed data and splits it into two data streams: a first data stream for the measurement frames and a second data stream for the image quality assessment frames.

Information from the quality assessment frames is used by the APC Executive to determine the reliability of the measurements. The reliability information is sent to the Control Sub-System along with the measurement data. The quality assessment frames can also be used by the APC Executive to fine-tune device parameters to improve image quality. However, the APC Executive is only allowed to autonomously adjust parameters that do not potentially introduce measurement bias. For example, increasing the amount of light used for the images can make the red-blood cell interface more distinct, but can also cause an apparent shift in the interface position. In one embodiment, significant adjustments to improve image quality (such as re-calibrating the lighting and exposure to re-optimize image quality) must be ordered by Procedure Control.

The optical density measurements are then processed to determine the current efficiency of the collection. The measurements are sent to the Control Driver, and then sent to the Machine State Data. Procedure Control uses these measurements to adjust the commanded interface position used by the Control Driver to optimize the collection. In one embodiment, the current interface position measurement is filtered by the APC Executive, and the APC Executive reports the filtered value along with trend information to the Control Driver. This data is used internally by the Control Driver to adjust operating parameters, such as peristaltic pump flow rates and the rotational velocity of the centrifuge, as necessary to maintain the commanded interface position.

The exemplary control system illustrated in FIG. 12 can be executed using a multiprocessor computing system. Selected components of control systems of the present invention can be run in a distributed fashion on separate processors. In one embodiment, the Procedure Control and the Control Driver run on a first processor, the Image Processing Engine runs on a second processor and the APC Executive runs on a third processor. Use of multiple processing computing methods in the present invention allows measurements to be extracted from a large amount of raw image data, and allows the measurements to be used to provide flexible dynamic device control on very short time scales, such as a time scale less than 50 milliseconds.

APC Sub-System and Control Sub-System can be configured in two-way communication via any means known in the art, such as an Ethernet connection. Components of either the APC Sub-System or the Control Sub-System can be configured to be in two-way or one-way communication via use of shared memory. in an exemplary embodiment, however, the APC Sub-System and the Control Sub-System do not communicate using shared memory.

The process control system of the present invention can also be configured to provide for effective data archiving of raw image data, processed image data and device settings. This functionality of the present invention allows a user to review blood processing data after a selected procedure to extract additional information, such as information related to the composition of collected blood components or the effectiveness of a given therapy. In the present invention, data archiving can be achieved by the APC Sub-System, the Control Sub-System or both. At least a portion of data extracted from acquired two-dimensional distributions of transmitted light intensities, such as measured operating parameters, are optionally also be displayed to an operator or service technician.

2B(ii) Control Driver and APC Sub-System Relationship.

Figure 13:
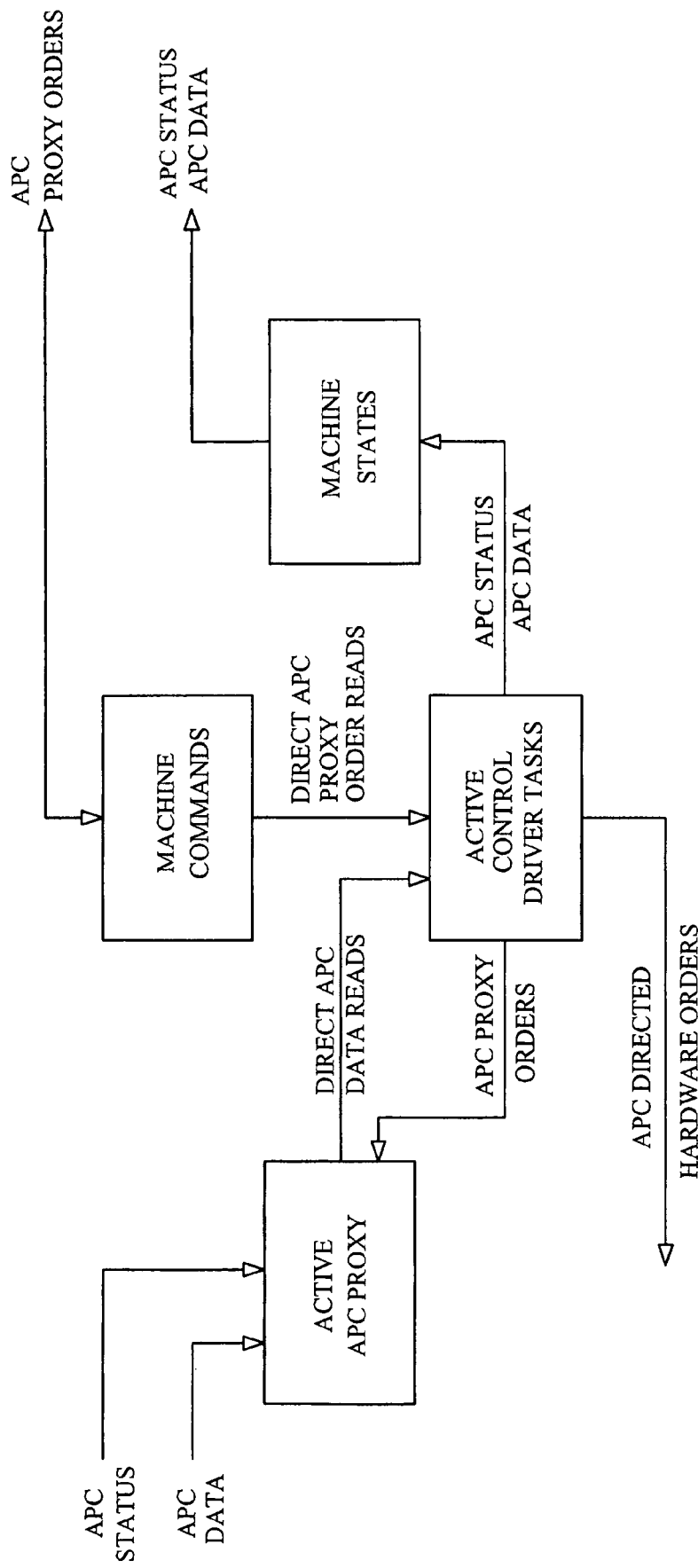
FIG. 13 is a schematic diagram showing exemplary Control Driver and APC Sub-System architectural relationships useful in the methods of the present invention.

FIG. 13 is a schematic diagram showing exemplary Control Driver and APC Sub-System architectural relationships useful in the methods of the present invention. For the sake of clarity, only APC relevant message paths and objects are included in FIG. 13.

In the embodiment illustrated in FIG. 13, APC proxy task within the Control Driver contains closed loop transfer functions that dynamically determine important centrifuge device settings including, but not limited to, pump flow rates, valve positions, and rotational velocity of the centrifuge, to achieve process control targets specified by Procedure Control. The transfer function performs hardware adjustments to minimize the difference between the error signals and the desired reference parameters. Procedure Control uses the APC status information to verify the operation of the APC and uses the APC data to obtain overall processing, predictive or trending information. Procedure Control periodically analyzes the trending data for specific patterns, and use the results of the analysis as the basis of adaptive process control decisions.

3B(iii) Procedure Control and APC Sub-System Relationship.

Figure 14:
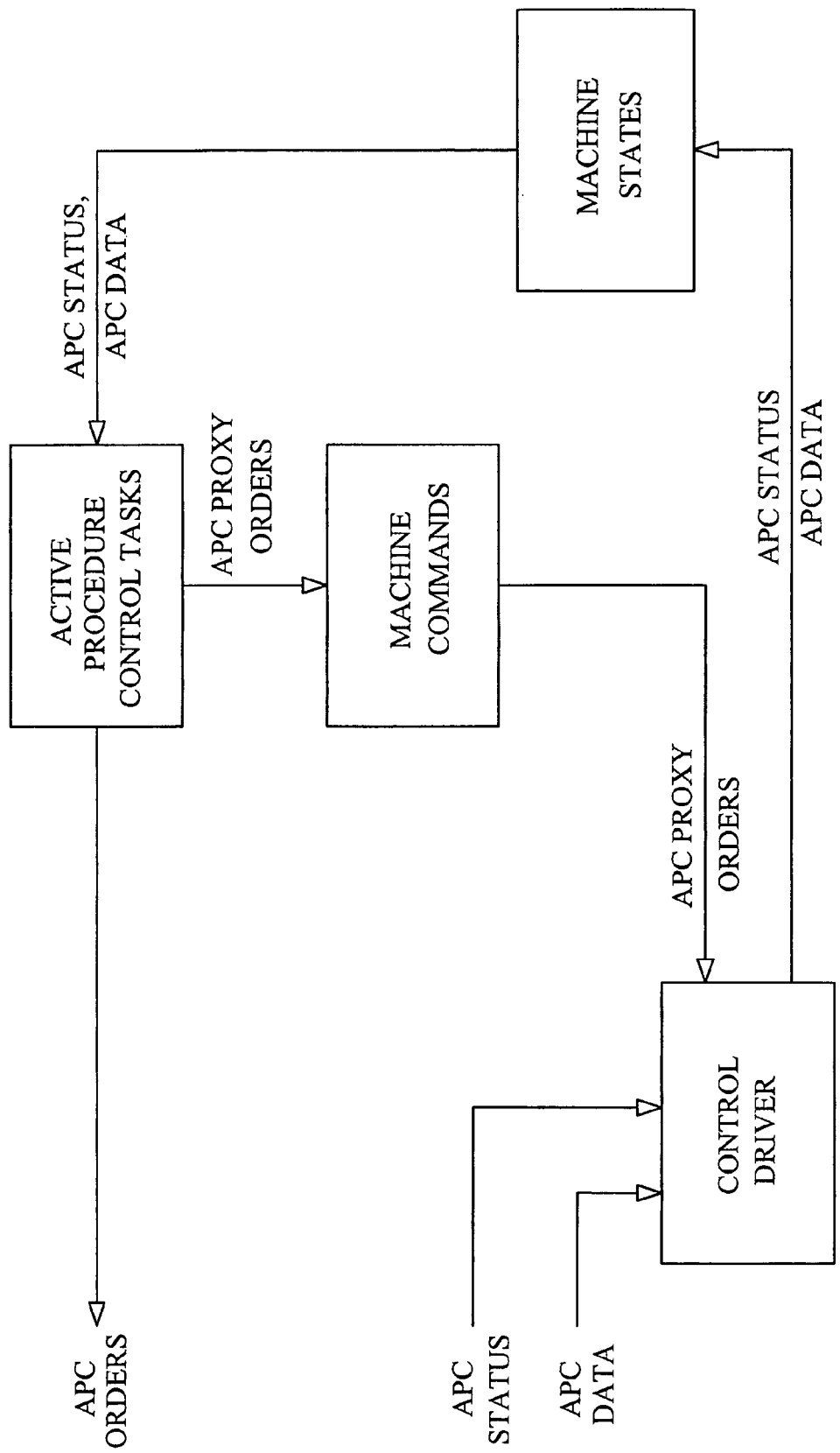
FIG. 14 is a schematic diagram showing exemplary Procedure Control and APC Sub-System architectural relationships useful in methods of the present invention.

FIG. 14 is a schematic diagram showing exemplary Procedure Control and APC Sub-System architectural relationships useful in methods of the present invention. For the sake of clarity, only APC relevant message paths and objects are included in FIG. 14.

Procedure Control utilizes the APC Sub-System as a smart real-time information server and has supervisory control over the APC Sub-System. In the embodiment illustrated in FIG. 14, Procedure Control selects operational modes of the APC Sub-System. According to the mode of operation, the APC transmits back to the Control Driver and Procedure Control, periodic sensor data analysis packets. In conjunction with commanding the APC Sub-System into a specific analysis mode, Procedure Control commands the Control Driver to enter into a specific type of closed-loop transfer function mode. The Control Driver is configured to receive the time-critical APC sensor data as an error-signal input to it's closed looped feedback transfer functions. Procedure Control performs adaptive process control by analyzing the trending or statistical behavior data over longer time periods and adjusting the Control Driver's transfer function set points to achieve a desired procedure performance.

3B(iv) APC Executive

Figure 15:
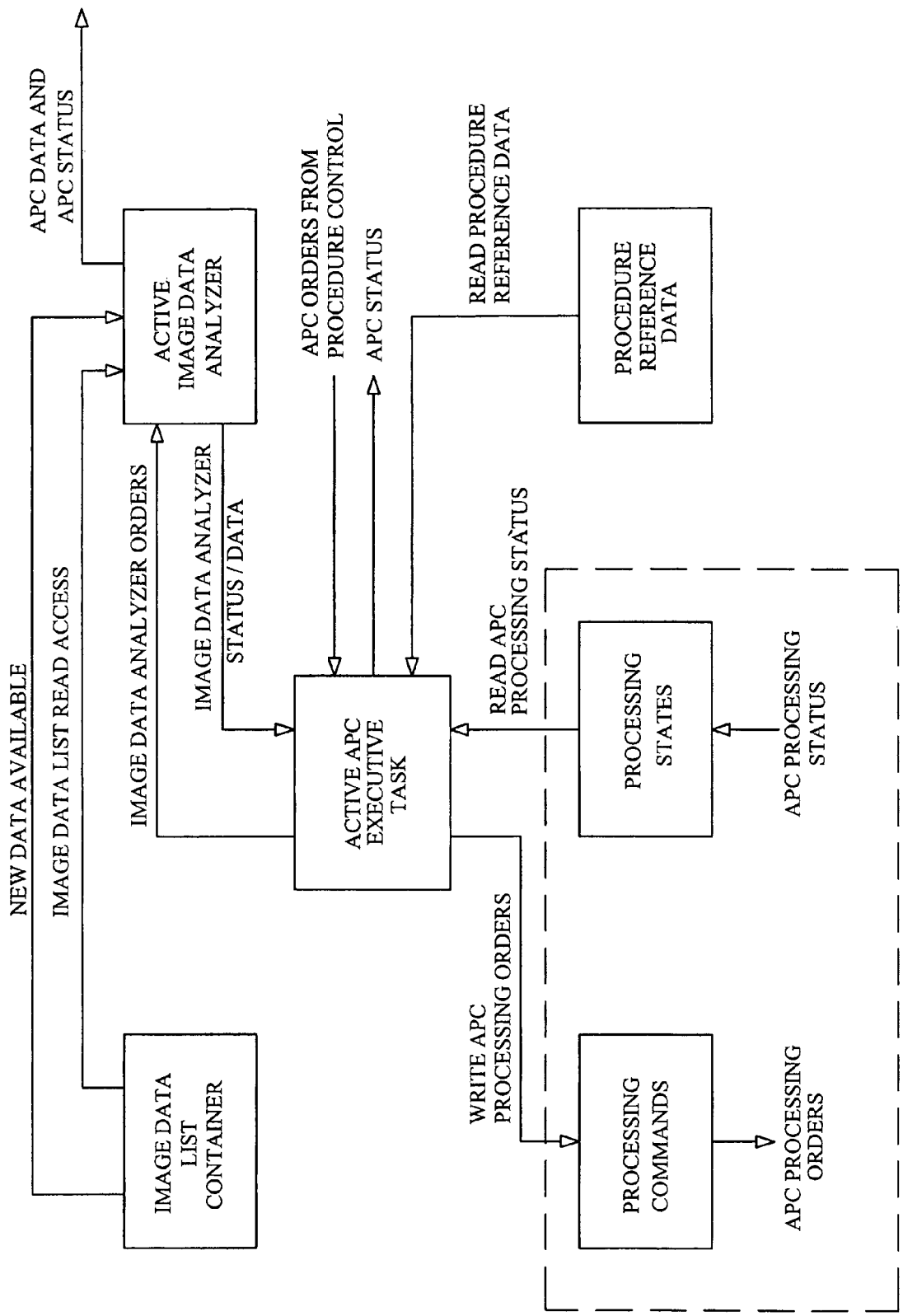
FIG. 15 shows exemplary architectural relationships of the APC Executive with the APC Driver, Image Data List Container, and the APC components within the Control Sub-System useful in the methods of the present invention.

The APC Executive is configured to manage the APC Sub-System while providing real-time process control information to the Control Sub-System. FIG. 15 shows exemplary architectural relationships of the APC Executive with the APC Driver, Image Data List Container, and the APC components within the Control Sub-System useful in the methods of the present invention.

Figure 16:
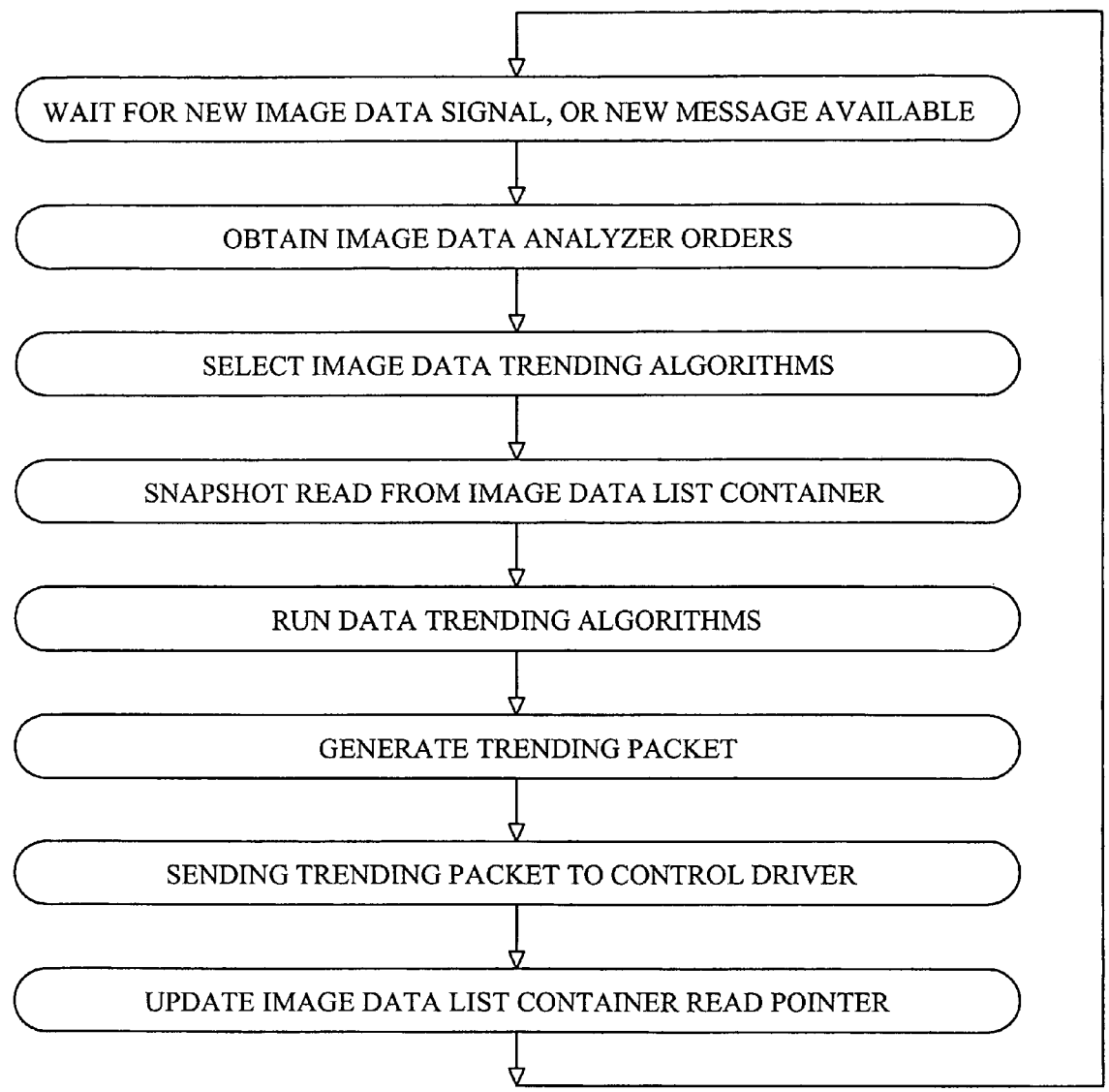
FIG. 16 is a schematic diagram providing a state chart for the image data analyzer task.

The APC Executive task is responsible for controlling the image acquisition, image analysis, and streaming-data output of the APC Sub-System in accordance with a selected Procedure Control's orders. The executive task evaluates the APC orders and determine an appropriate course of action. If Procedure Control is requesting that the APC Sub-System change it's blood component processing monitoring or analysis modes, then the executive task can perform the following operations: (1) send APC processing (image acquisition/processing) orders to APC Driver component via the processing commands object, (2) send image analysis and data-feed orders to the Image Data Analyzer, (3) monitor the Image Data Analyzer's status and data-feed output, and then send APC (change-mode) status back to Procedure Control. After establishing the desired mode of operation, the APC Executive can automatically monitor and control the APC Sub-System to maintain the flow of requested information back to the Control Sub-System. The orders sent to the Image Data Analyzer specify the type of multivariable real-time analysis that the snapshot analyzer should perform and the type of data packets that the Image Data Analyzer should spool back to the Control Driver. The orders can also specify the type and level of error management and data filtering that the Image Data Analyzer should perform. When the Image Processing Engine inserts new data onto the list, the Image Data Container notifies the Image Data Analyzer. Then the Image Data Analyzer snapshot analyze the new image data object along with a number of preceding objects. FIG. 16 is a schematic diagram providing a state chart for the image data analyzer task.

The APC Executive is also be responsible for calibration and error handling within the APC Sub-System. In one embodiment, the APC Executive autonomously manages its calibration and error handling up until predetermined non-recovery limits. Alternatively, the APC Executive is configured to always respond to error recovery and calibration orders from Procedure Control. In either the directed or autonomous error recovery/calibration cases, the Control Sub-System is configured to receive the appropriate status information. Procedure Control receives error status messages from the APC Executive once it has recognized an error condition, while the Control Driver is simultaneously receiving trending packets with both data and error or degraded performance information. The APC Sub-System can manage calibration and error handling using predetermined validation parameters in orders that the APC Executive sends the Image Data Analyzer. In an embodiment of the present invention, the Procedure Control is the final arbitrator for the determining whether the APC Sub-System is working correctly and sending the Control Driver the requested control loop and adaptive process control information.

3B(v) APC Driver

Figure 17:
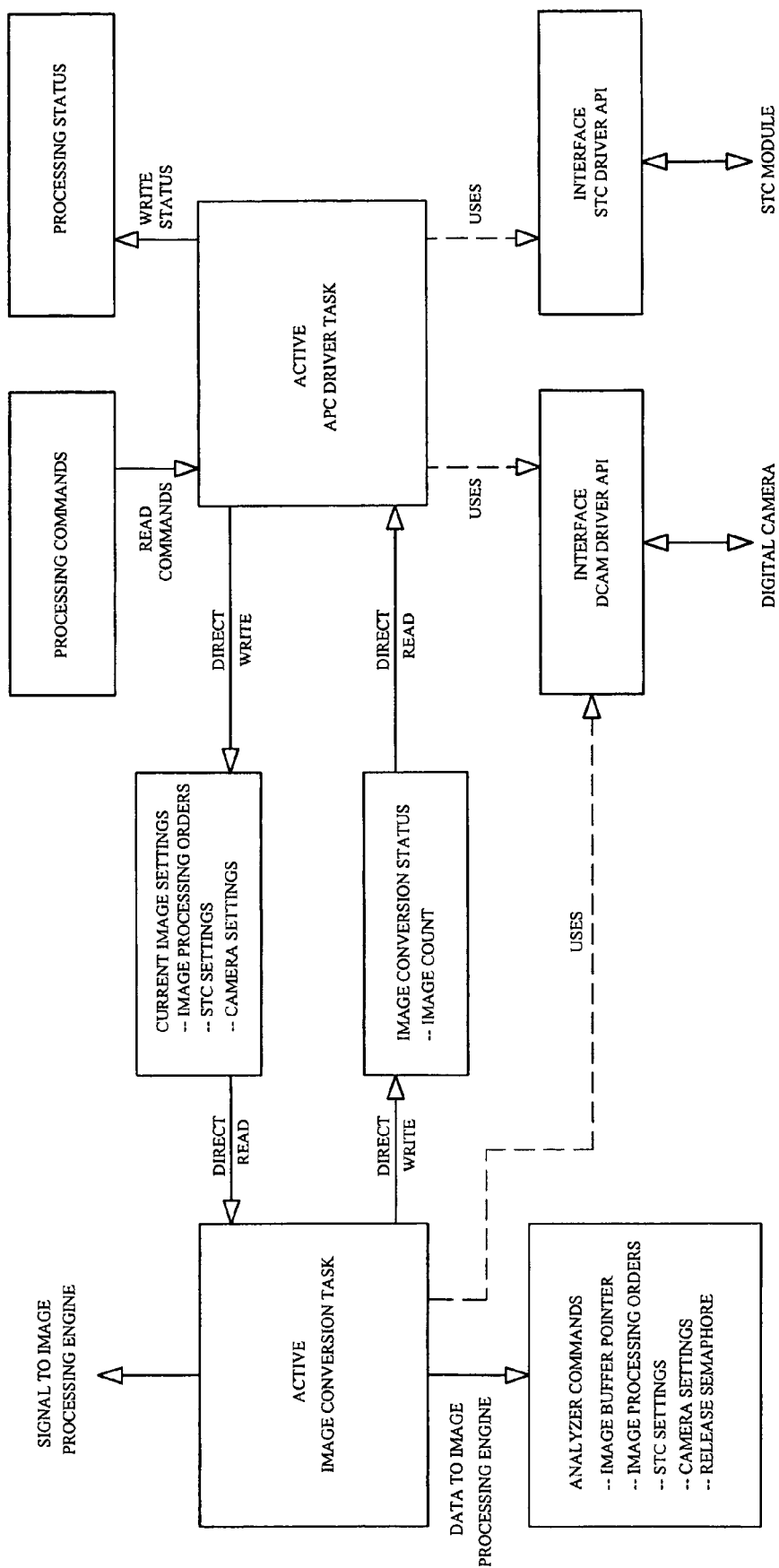
FIG. 17 shows an exemplary architecture of the APC Driver component of the present invention.

FIG. 17 shows an exemplary architecture of the APC Driver component of the present invention. As shown in FIG. 17, the APC Driver consists of two active tasks. The APC Driver task is responsible for the interface to the APC Executive and is configured to read processing commands from the APC Executive, and set the camera and STC properly for executing those commands. It also is configured to write back status associated with the APC Driver operation for use by the APC Executive.

The image conversion task is responsible for receiving the raw image data from the camera and for generating a packet of information to the Image Processing Engine which includes this image data, the STC and camera settings, and the processing orders associated with the particular image. When a new image is available, a signal is sent to the Image Processing Engine to notify it of the availability of the new image data. The image conversion task is also be responsible for managing the buffers used to receive raw image data from the camera and the buffer used to send data to the image processing engine. The Image Processing Engine is be responsible for signaling when it no longer needs a particular object.

Figure 18:
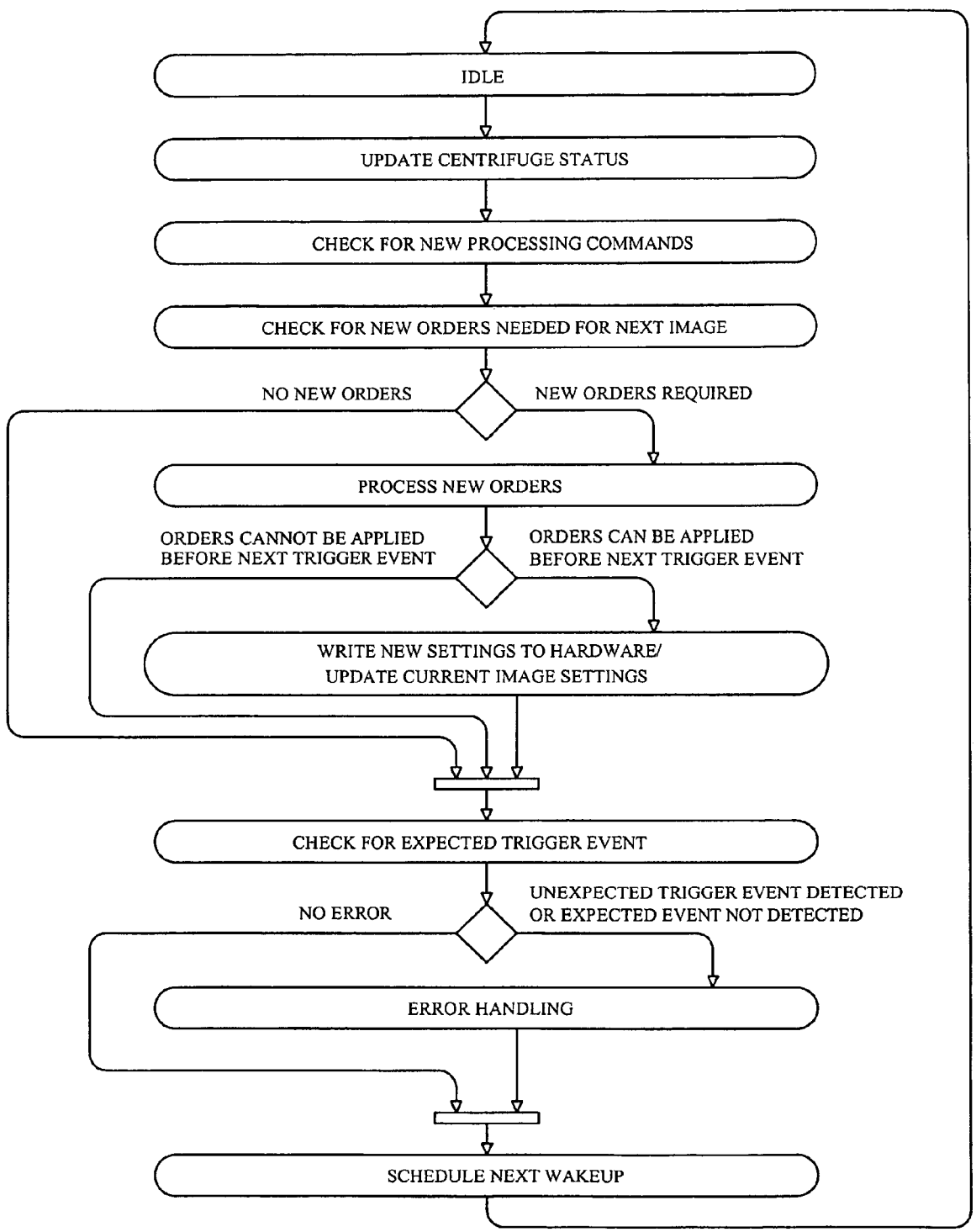
FIG. 18 shows an exemplary high level state diagram for a APC Driver task useful for the methods of the present invention.

FIG. 18 shows an exemplary high level state diagram for a APC Driver task useful for the methods of the present invention. Table 1 describes each of the states provided in FIG. 18.

TABLE 1

APC Driver Task States Description

| State | Description |
|---|---|
| Idle | Waiting for wakeup event. Wakeup events can be generated from new orders sent from the APC Executive, or from a wakeup time scheduled on a previous scan through the APC Driver task state machine. |
| Update Centrifuge Status | The APC Driver task monitors centrifuge position and speed through the STC. This data is used to compute timing for when trigger events are expected and to determine if new hardware settings can be safely written before a pending trigger event. |
| Check for New Processing Commands | This state checks for new processing commands from the APC Executive. If new commands are available, the APC Driver task generates a new set of internal orders to be used for image acquisition. |
| Check for New Orders Needed for Next Image | The APC Executive can command a sequence of one or more images to be processed. For example, it might command 10 images for tracking blood interface position, followed by an image used to periodically assess image quality. During this state, the driver determines if the next image to be acquired requires any change in the current STC and camera settings. |
| Process New Orders | If new hardware settings are required for the next image, the driver must then determine if a sufficient time is available to write these settings before the next trigger event. This determination uses the current centrifuge position and speed, the position or the next trigger event, and the particular hardware settings that must be modified (e.g. changing only strobe duration on the STC can be faster than changing camera exposure settings). |
| Write New Settings to Hardware | New settings are written to the hardware, and the CurrentImageSettings object is updated so that when the image is received by the image conversion task, the correct settings corresponding to that image are available. |
| Check for Expected Trigger Event | In order to ensure correct synchronization between image settings and image data, the APC Driver task must check that image data is received by the image conversion task at the specified time. Either a false camera trigger (image data sent when none was expected) or a missed camera trigger (no image data sent when a new image should have been acquired) can cause the synchronization of the CurrentImageSettings data and the image data received from the camera to be lost. |
| Error Handling | If a synchronization error is detected, the hardware must be reset to a known state, and the driver task resynchronized with the incoming image data. |
| Schedule Next Wakeup | The APC Driver task schedules the next wakeup event for the time to the next expected trigger event (based on current centrifuge position and speed). However, if this time exceeds 10 msec, the next wakeup is scheduled for 10 msec instead, to ensure that centrifuge speed changes are tracked appropriately. |

3B(vi) Image Processing Engine

Figure 19:
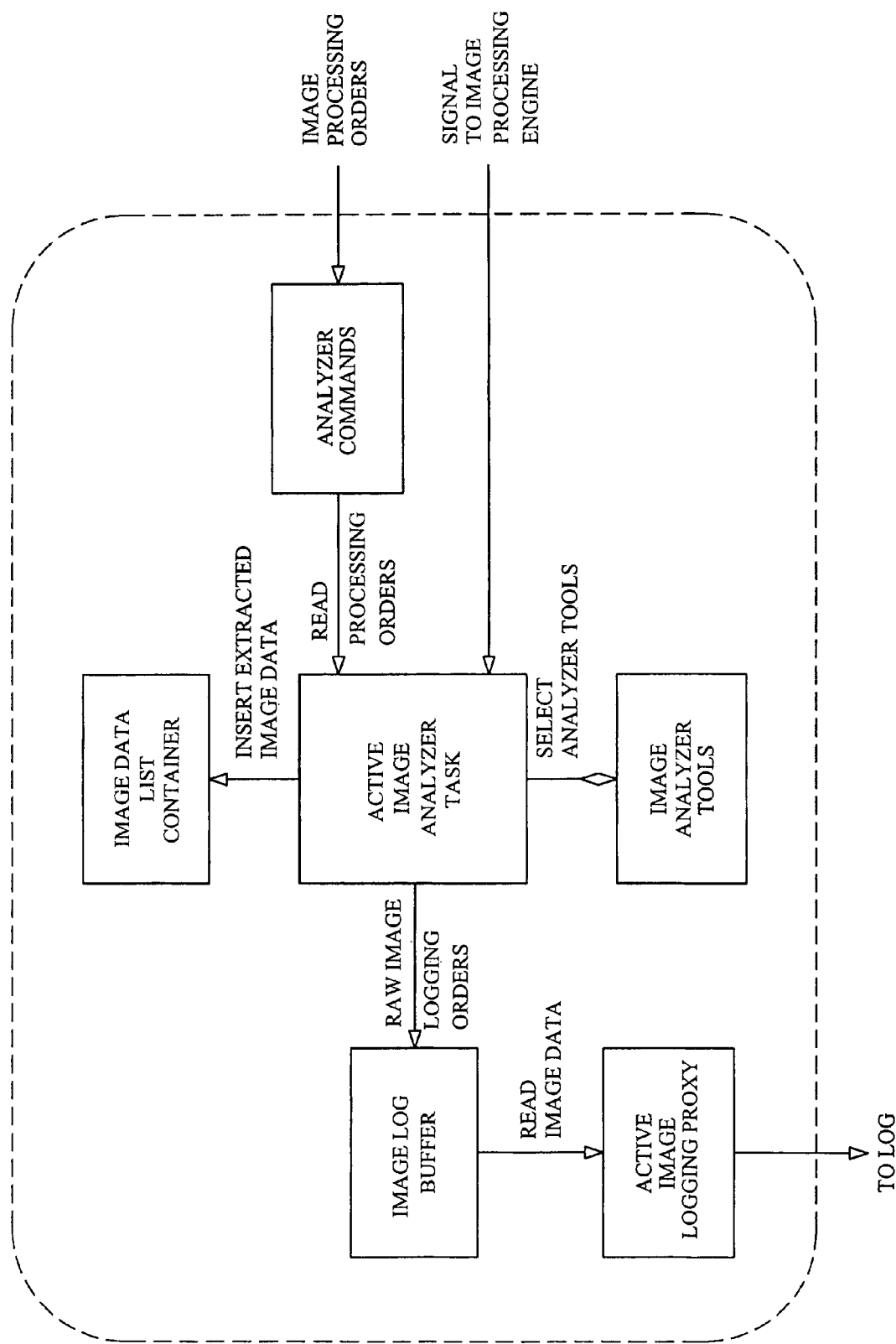
FIG. 19 shows an exemplary architecture of a APC Image Processing Engine component of the present invention.

FIG. 19 shows an exemplary architecture of a APC Image Processing Engine component of the present invention. For the sake of clarity, not all data and message paths are included in this diagram and only those data and message paths relevant to the following are included.

Figure 20:
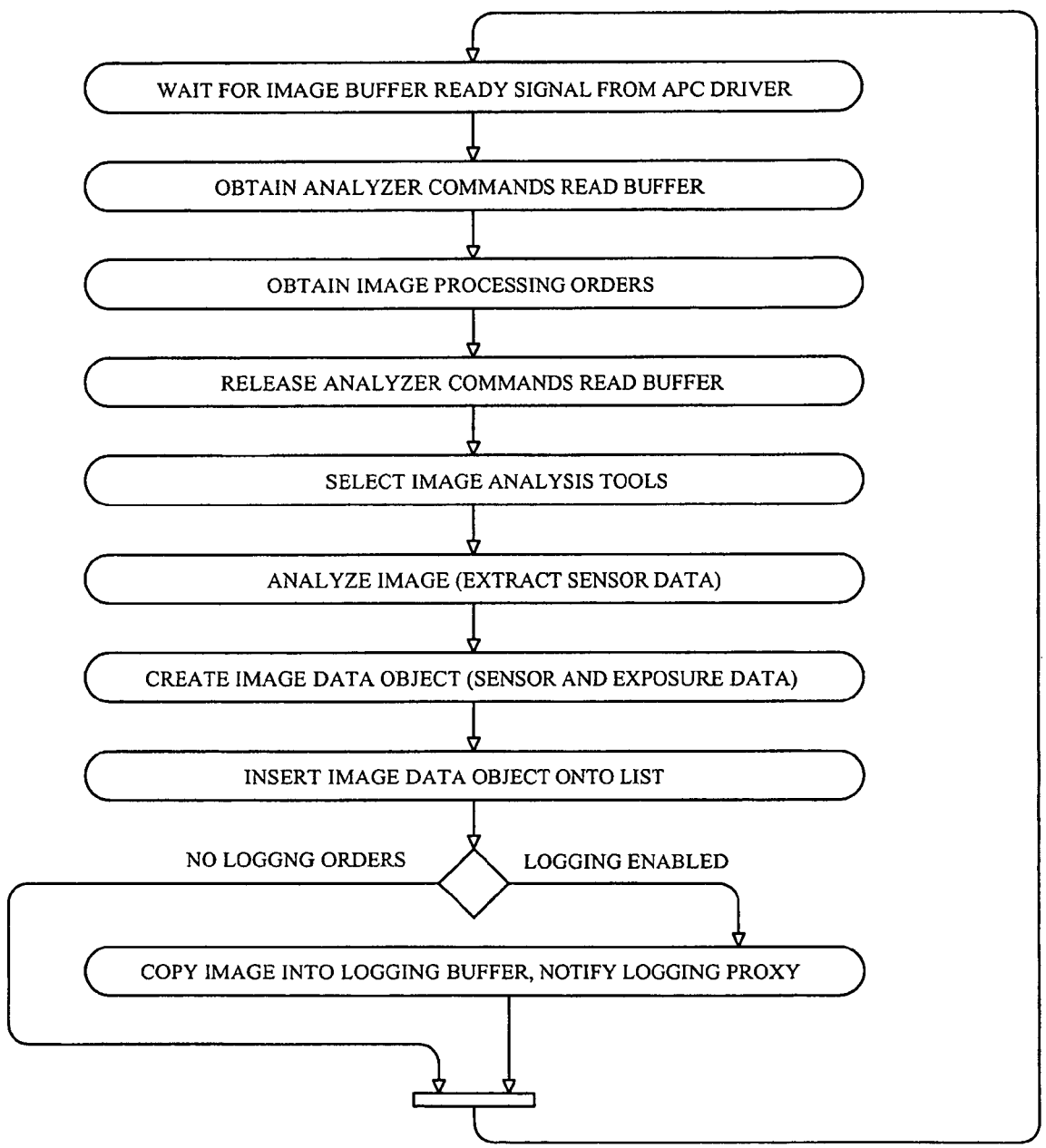
FIG. 20 provides an exemplary state chart for an image analyzer task useful in the methods of the present invention.

In one embodiment, the image analyzer task is responsible for the real-time analysis of continuously streaming still-type digital images (frames). For a new image frame, the image analyzer task applies a suite of sensor algorithms (image analyzer tools) to extract specific blood component processing measurements from the image. After each frame has been analyzed, the extracted sensor measurements, image exposure parameters (camera, STC settings), and time/sequence stamps are used to construct a new image data object. The image analyzer then inserts the new data object onto the Image Data List Container (chronologically ordered circular buffer). The analyzer task is be configured to receive each new image frame from the APC Driver component. For each new frame cycle the APC Driver loads an analyzable image structure into a designated memory buffer, update the analyzer commands object, and then notify the image analyzer task that a new image is ready to be processed with an image buffer ready signal. The architecture of the Image Analyzer partially decouples the asynchronous real-time image exposure and processing intervals defined by the centrifuge rpm from the executive task. The APC Executive indirectly controls and monitor the Image Analyzer through the APC Driver and the Image Data List Container. When the APC Executive task sends processing orders to the APC Driver, the APC Driver redirects the image processing orders contained within the APC Executive's processing orders to the analyzer commands object. Image processing orders are used to determine the analyzer's mode of operation and the type of analysis that it performs. The APC Executive is configured to monitor the analyzer's image processing status by evaluating its output to the Image Data List Container. FIG. 20 provides an exemplary state chart for an image analyzer task useful in the methods of the present invention.

In an embodiment, the analyzer task receives its processing orders from the read buffer of the analyzer commands objects for each frame. When the analyzer task is signaled by the APC Driver that a new image is ready to be processed it obtains the image buffer location, image processing orders, and image exposure setting from the analyzer commands read buffer. It then selects the image analysis tools specified by the analyzer commands object and analyze the image. After the analysis, the analyzer task uses the extracted measurement data, image time stamps, image sequence count, and STC/camera exposure event settings, to create a new image data object. After creating the new image data object, the analyzer task then inserts it onto the Image Data List Container. If analyzer commands object orders enabled image data logging, it copies the image structure into the image log buffer and signal the logging proxy that new logging data is available.

3B(vii) Image Data List Container

The Image Data List Container is configured to provide managed access to chronologically ordered sequences (circular buffer) of extracted image sensor data. The Image Processing Engine inserts image data objects into the Image Data List Container each time it processes a new image frame. The APC Executive is configured to receive notification of new data being inserted onto the list container from the Image Data List Container.

C. Image Processing Algorithms.

In one aspect, the present invention provides image processing algorithms useful for extracting measurements from two-dimensional distributions of transmitted and/or scattered light intensities comprising images of components of a blood processing system and/or a blood sample undergoing processing. Useful image processing algorithms for the methods of the present invention can be classified in several fundamental measurement categories including (1) direct measurements, (2) statistical measurements and (3) frequency based measurements.

Direct measurements refer to evaluation of the distances from known device components in a blood processing system and performing best fit algorithms to determine important features, such as the position of phase boundaries between optically differentiable separated blood components. Exemplary direct measurements and corresponding image processing algorithms useful for the methods of the present invention include, but are not limited to, (1) a measurement vector along the detected edge regions relative to the phase boundaries between separated blood components; (2) adaptive thresholding edge detection and/or gradient-based edge detection techniques to automatically determine accurate measurements of the positions of phase boundaries between separated blood components; (3) pattern matching algorithms for determining the position, orientation and physical dimensions of a known device component or element of a known device component; (4) a distance measurement from a known device component or element of a known device component, such as the distance from the top of a rib on an optical cell to the RBC—Buffy coat layer phase boundary, buffy coat layer—plasma phase boundary or platelet—plasma phase boundary; (5) a distance measurement from a known a known device component or element of a known device component to a region of interest.

Statistical measurements refer to measurements which probe intensity values over a region of interest and use statistical tools to determine average light intensities and/or spatial distribution of light intensities of light transmitted and/or scattered from observation regions corresponding to important device components, such as light transmitted and/or scattered from one or more extraction ports or inlets. In this manner, fluxes and compositions of separated blood components in a region of interest, such as an extraction port, are determined in real time. Exemplary statistical measurements and corresponding image processing algorithms useful for the methods of the present invention include, but are not limited to: (1) a measurement of the mean intensity of transmitted and/or scattered light from a region of interest (e.g. extraction port); (2) a measurement of the median intensity of transmitted and/or scattered light from a region of interest (e.g. extraction port); (3) a measurement of the minimum and/or maximum intensity of transmitted and/or scattered light from a region of interest (e.g. extraction port); (4) a measurement of the percentage contrast in an image of a region of interest (e.g. extraction port); (5) measurements of variance and standard deviation of observed transmitted and/or scattered light intensities of light from a region of interest (e.g. extraction port); (6) entropy distributions of measured transmitted and/or scattered light intensities of light from a region of interest (e.g. extraction port).

Frequency measurements translate measured light intensities of a two dimensional distribution of light intensities to identify the difference between high frequency and low frequency components. In one embodiment, for example, fast Fourier transform (FFT) or a power spectral series $(FFT)^2$ are used to evaluate the homogeneous or inhomogeneous nature of the flux of cellular material through an extraction port useful for evaluating the composition of extracted, separated blood components. Exemplary frequency measurements and corresponding image processing algorithms useful for the methods of the present invention include, but are not limited to: (1) determination of the minimum frequency resolution provide by the equation:

$$\text{minimum frequency resolution} = \frac{1}{(\text{length of the region of interest})} \quad \text{(III)}$$

(2) determination of the frequency resolution provided by the equation:

$$\text{frequency resolution} = \frac{(\text{number of frequency samples})}{(\text{length of the region of interest})} \quad \text{(IV)}$$

(3) determination of the ratio of the maximum frequency to minimum frequency within a selected range; (4) determination of the distribution or other characteristics of the power spectrum as a function of the radius of the power spectrum.

Image processing algorithms operate on a single two-dimensional distribution of transmitted and/or scattered light intensities corresponding to an image of a device component and/or blood sample to determine operating conditions useful for controlling a blood processing device. Measurements that can be extracted from a single frame of image data include, but are not limited to, the positions of phase boundaries between optically differentiable separated blood components, the composition and flux of extracted, separated blood components passing through an extraction port, and the composition of blood passing through an inlet on a separation chamber. Uncertainties in these measurements can also be ascertained in real time from a single frame of image data analyzed by image processing algorithms of the present invention. Evaluating uncertainties in measured parameters is important in the present methods because it provides important data relevant to the data should be used in trending.

Alternatively, image processing algorithms can operate on a plurality of two-dimensional distributions of transmitted and/or scattered light intensities corresponding to multiple images of a device component and/or blood sample. Image processing algorithms that operate on multiple frames of image data are useful for analyzing and predicting the temporal behavior of important operating conditions, such as the positions of phase boundaries between optically differentiable separated blood components and the compositions and fluxes of extracted, separated blood components passing through an extraction port. Exemplary Image processing algorithms that operate on multiple frames of image data comprise predictive data analysis algorithms capable of monitoring trends in important measurements in real time. Such predictive data analysis algorithms provide process control systems capable of very quickly adjusting one or more device settings in response to changes in blood processing conditions or sample composition for optimizing a given procedure or therapy.

Image processing algorithms of the present invention can be determined empirically by correlating measured parameters, such as average intensities of transmitted and/or scattered light or two dimensional distribution of intensities of transmitted and/or scattered light, with observed compositions of extracted separated blood components. in one embodiment, such correlations are determined by operation of fitting algorithms to individual image data sets or multiple image data sets. Appropriate correlations for image processing algorithms of the present invention can depend on the composition of the blood undergoing processing or other characteristics of a donor or a patient undergoing treatment. Alternatively, in another embodiment correlations are determined using nueral networks and machine learning algorithms known in the art. For example, such machine learning algorithms are used to continually refine image processing algorithms by operation on archived image data.

An exemplary method for controlling a blood processing device comprises the steps of: (1) performing a first measurement of an operating condition of said blood processing device corresponding to a first time; (2) performing a second measurement of said operating condition of said blood processing device corresponding to a second time; (3) analyzing said first and second measurements of said operating condition using a predictive data analysis algorithm, wherein operation of said predictive data analysis algorithm generates a predicted operating condition of said blood processing device at a future time; and (4) adjusting at least one setting of said blood processing device based on said predicted operating condition of said blood processing device at said future time, thereby controlling said blood processing device.

EXAMPLE 4

Optical Cell for Monitoring and Controlling Blood Processing

The present invention includes optical cells for use in monitoring and controlling blood processing using a wide variety of blood processing techniques. Optical cells of the present invention are capable of transmitting at least a portion of an incident light beam and/or light scattered by one or more fluid components in the optical cell. Optionally, optical cells of the present invention may comprises selectively absorbing, reflecting, scattering, collimating and/or focusing regions capable of selectively manipulating an incident light beam or light scattered by one or more fluid components in the optical cell. Moreover, optical cells of the present invention maximize regions of a blood separation system which are viewed and optically characterized using a fixed position CCD OR CMOS camera equipped with a fixed focus lens system. This feature of optical cells of the present invention provides for multifunctional blood processing systems which are capable of simultaneously monitoring and controlling a plurality of blood processing operating conditions, including composition of separated blood components, fluxes of extracted, separated blood components and positions of phase boundaries between optically differentiable separated components.

Figure 21A:
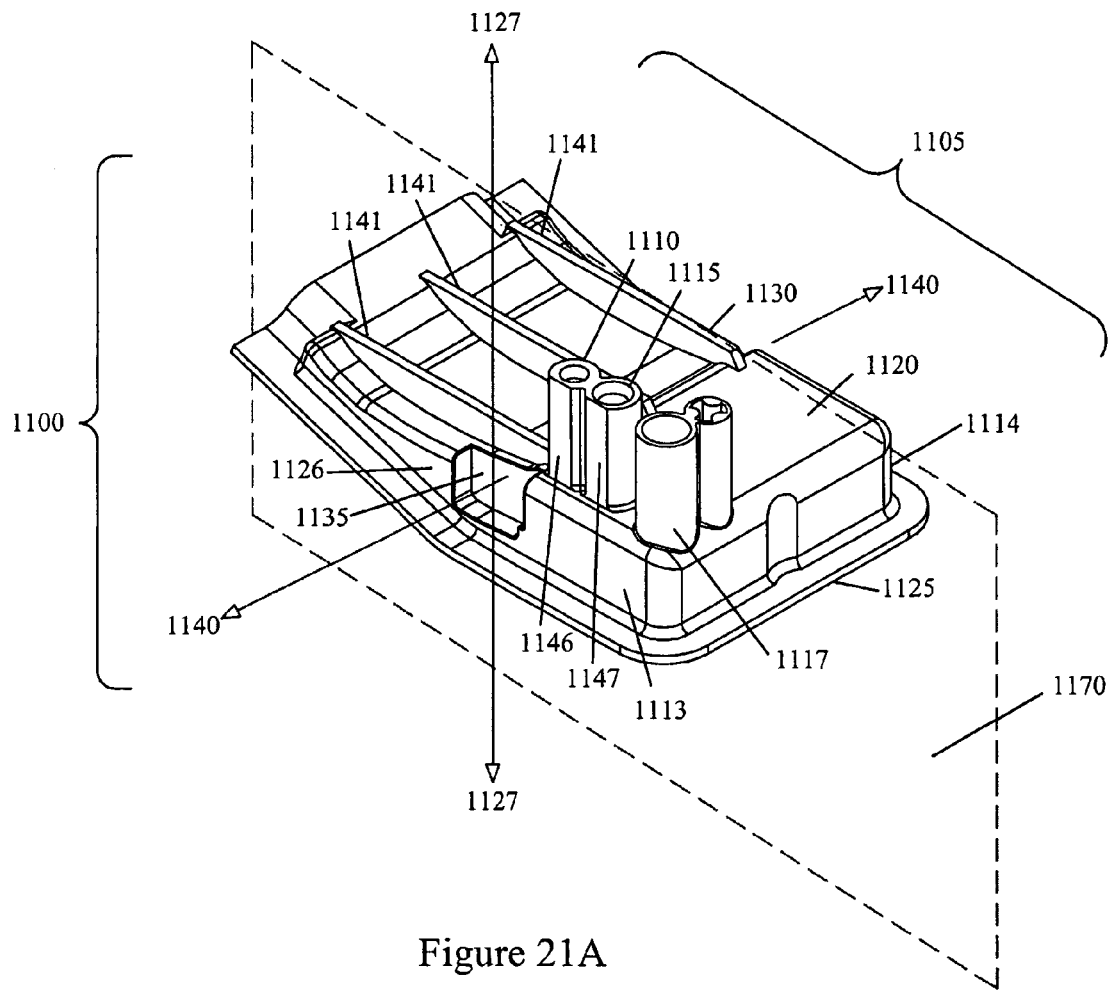
FIG. 21A provides a schematic diagram of a rotated side view of an optical cell of the present invention useful for monitoring blood processing via density centrifugation.

FIG. 21A provides a schematic diagram of a rotated side view of an optical cell of the present invention useful for monitoring blood processing via density centrifugation. The illustrated optical cell 1100 comprises a blood component extraction chamber 1105, a first extraction port 1110, a second extraction port 1115 and a third extraction port 1117. Extraction chamber 1105 comprises a first side wall 1120 and a second side wall 1125 which define a blood separation region 1126, wherein blood components are separated along separation axis 1127 on the basis of density upon formation of a centrifugal field by a density centrifuge. In the embodiment shown in FIG. 21A, extraction chamber 1105, first extraction port 1110 and second extraction port 1115, are each capable of passing at least a portion of incident light, such as light propagating along an optical axis which is substantially parallel to the incident light beam axis 1140 and light scattered by blood or blood components in blood separation region 1126, first extraction port 1110, and/or second extraction port 1115. Optionally, optical cell 1100 can further comprise ribs 1141 to enhance structural integrity and provide good mechanical ruggedness.

As shown in FIG. 21A, first extraction port 1110, second extraction port 1115 and third extraction port 1117 are tubular elements in fluid communication with blood separation region 1126. In an embodiment of the present invention, first extraction port 1110 terminates at an orifice positioned about midway between first side wall 1120 and second side wall 1125, second extraction port 1115 terminates at an orifice positioned proximate to first side wall 1120 and third extraction port 1117 terminates at an orifice positioned proximate to second side wall 1125. This arrangement allows blood components of different densities to be extracted through different extraction ports because first, second and third extraction ports 1110, 1115 and 1117 are in fluid communication with different regions of blood separation region 1126 during blood processing. In one embodiment of the present invention, optical cell 1100 is configured such that white blood cells can be extracted through first extraction port 1110, plasma and/or platelets can be extracted through second extraction port 1115, and red blood cells can be extracted through third extraction port 1117.

Optical cell 1100 is configured such that it can be coupled to a blood separation chamber (not shown in FIG. 21A) such that blood undergoing processing is flowed through optical cell 1100, and discrete fractions corresponding to selected blood components are extracted through first, second and third extraction ports 1110, 1115 and 1117. In one embodiment, optical cell 1100 is an integrated element of a blood processing chamber. In another embodiment, optical cell 1100 is a separate component of a blood processing system in fluid communication with a separation chamber. In one embodiment, optical cell 1100 is configured such that it is periodically rotated into and out of an observation region of an optical monitoring and control system of the present invention as the separation chamber of a density centrifuge rotates. In this manner, two dimensional distributions of intensities of transmitted light, scattered light or both comprising images of optical cell 1100 are measured for each rotation or for selected rotations. Optical cell 1100 can comprise a disposable component of a blood processing system or can be a reusable component.

Extraction chamber 1105, first extraction port 1110, second extraction port 1115 and third extraction port 1117 can further comprise one or more optical surfaces capable of transmitting light, such as an incident optical beam or light scattered from blood or blood components. Optical surfaces of extraction chamber 1105, first extraction port 1110, second extraction port 1115 and third extraction port 1117 can be external optical surfaces that are not in contact with blood undergoing processing and are exposed to the ambient surroundings. Alternatively, optical surfaces of extraction chamber 1105, first extraction port 1110 second extraction port 1115 and third extraction port 1117 can be internal optical surfaces that are in contact with blood undergoing processing and not exposed to the ambient surroundings. In an exemplary embodiment, optical surfaces of extraction chamber 1105 are positioned such that a high quality optical image of at least a portion of the optical cell 1100 is generated upon illumination with a first collimated light beam directed on the top 1113 of optical cell 1100 and a second collimated light beam directed on the bottom 1114 of optical cell 1100. This configuration allows two dimensional distributions of light intensities comprising images of optical cell 1100 to be measured and analyzed in real time.

Use of the term optical surface in the present invention refers to surfaces capable of efficiently transmitting incident light, such as collimated, incident light beams having a selected distribution of wavelengths, such as wavelengths in the visible and/or infrared regions of the electromagnetic spectrum, and/or light scattered from blood or blood components undergoing processing. Optical surfaces of the present invention preferred for some applications of the present invention do not significantly alter the intensities, wavelength distribution and spatial characteristics of incident light, such as propagation direction and extent of collimation. Optical surfaces of the present invention can be substantially optically flat, such as the degree of flatness provided by a diamond polish, for example a degree of flatness exhibiting deviations from absolute flatness less than about 0.001 inch. Use of optically flat optical surfaces in optical cells of the present invention is beneficial because they are capable of efficiently transmitting a collimated light beam without substantially distorting the spatial characteristics of the beam, such as transmitting a collimated beam without significant focusing and without significantly increasing beam divergence. Optical surfaces of the present invention can also be optically smooth surfaces, such as the degree of smoothness provided by a diamond polish, for example a degree of smoothness provided by a diamond polish exhibiting deviations from a absolutely smooth surface of less than about 3 microinches. Use of optically smooth surfaces in optical cells of the present invention is beneficial because they are capable of providing highly transmissive surfaces wherein scattering of incident light from the optical surface is minimized. The present invention also include embodiments wherein optical cell 1100 comprises a plurality of optical surfaces that are positioned in substantially parallel planes. Use of parallel optical surfaces is beneficial for providing good transmission of light through optical cell 1100.

In the embodiment shown in FIG. 21A, extraction chamber 1105 has a first external optical surface 1130 and a second external optical surface 1135, capable of efficiently transmitting one or more collimated light beams propagating along optical axis substantially parallel incident light beam axis 1140 and/or light scattered from blood or blood components in blood separation region 1126. Optionally, extraction chamber 1105 can also comprise a first internal optical surface, second internal optical surface or both (not shown in FIG. 21A) positioned opposite to first optical surface 1130 and/or second optical surface 1135, respectively, and in contact with the blood separation region 1126. Preferable for some applications of the present invention, external and/or internal optical surfaces of extraction chamber 1105 are flat and oriented in substantially parallel planes to increase transmission of an incident light beam. External and/or internal optical surfaces of extraction chamber 1105 are preferably highly transmissive, optically flat and optically smooth, such that they are capable of providing a flat, undistorted image of at least a portion of top 1113 of optical cell 1100 to a CCD or CMOS camera positioned in optical communication with the extraction chamber.

Figure 21B:
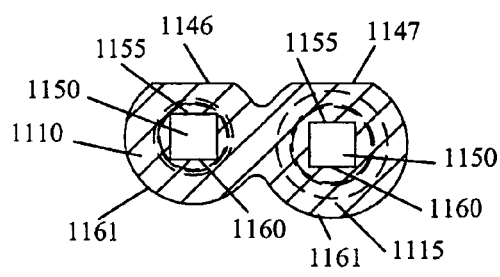
FIG. 21B provides a cross sectional view of an exemplary extraction port design of the present invention.

As shown in FIG. 21A, first extraction port 1110 and second extraction port 1115 have external optical surfaces 1146 and 1147, respectively, capable of efficiently transmitting one or more collimated light beams propagating along optical axis substantially parallel incident light beam axis 1140 and/or light scattered from blood or blood components in the extraction ports. FIG. 21B provides a cross sectional view of an exemplary extraction port design of the present invention. As shown in FIG. 21B, first extraction port 1110 and second extraction port 1115 each have an axial bore 1150 having a square cross sectional profile. In this embodiment, first extraction port 1110 and second extraction port 1115 have internal optical surfaces 1155, which are capable of efficiently transmitting one or more collimated light beams propagating along an optical axis which is substantially parallel to incident light beam axis 1140. Optionally, first extraction port 1110 and second extraction port 1115 can have additional internal optical surfaces 1160 positioned opposite optical surfaces 1155 to further increase transmission and minimize unwanted beam distortion affects, such as focusing and increasing beam divergence. In addition, first extraction port 1110 and second extraction port 1115 can have additional external optical surfaces 1161 to enhance transmission of light through first and second extraction ports 1110 and 1115. Internal and/or external optical surfaces of first extraction port 1110 and second extraction port 1115 are preferably highly transmissive, optically flat and optically smooth, such that they are capable of providing a flat, undistorted image of at least a portion of the extraction ports to a CCD or CMOS camera positioned in optical communication with the extraction chamber. Monitoring the transmission of light through first and second extraction ports 1110 and 1115 while blood components are extracted from blood separation region 1126 provides a means of measuring the composition of extracted blood components.

Figure 21C:
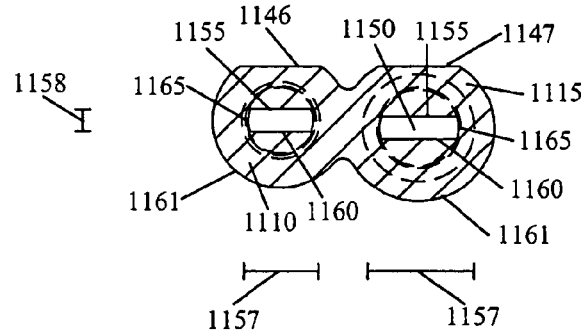
FIG. 21C provides a cross sectional view of an alternative extraction port design of the present invention, wherein first extraction port and second extraction port each have axial bores having a rectangular cross sectional profile.

The present invention also includes optical cell configurations having extraction ports with axial bores having cross sectional profiles other than square profiles, such as rectangular profiles, trapezoidal profiles and curved profiles. FIG. 21C provides a cross sectional view of an alternative extraction port design of the present invention, wherein first extraction port 1110 and second extraction port 1115 each have an axial bores 1150 having a rectangular cross sectional profile. Use of extraction ports having a rectangular cross sectional profiles with lengths 1157 of internal optical surfaces 1155 larger than the width 1158 of side walls 1165 is preferred for some applications because it provides for better measurements of the composition and/or flux of cellular and/or noncellular materials in the extraction port. For example, use of rectangular cross sectional profiles providing a very thin axial bore 1150 (i.e. having length 1157 significantly larger than width 1158) is beneficial because it distributes absorbing material, such as cellular blood components, in a layer having a larger cross sectional area positioned orthogonal to the propagation axes of the incident beam, which allows the spatial distribution of such absorbing material to be more accurately characterized. Further, use of a thin axial bore 1150 is beneficial because it decreases the optical path length of the beam through the extracted component, which is useful for avoiding substantially complete absorption of an incident beam directed onto the extraction ports. In one embodiment, extraction ports 1110 and 1115 have rectangular cross sectional profile characterized by an aspect ratio (aspect ratio= (width)/(length)) selected over the range of about 0.1 to about 0.4. For example, an extraction port of the present invention has a length 1157 equal to about 0.080 inches and a width 1158 equal to about 0.030 inches. Selection of the cross sectional profile and physical dimensions of axial bores 1150 of extraction ports of the present invention can be made on the basis of the flow rates through the extraction ports desired, optical transmission considerations and light imaging considerations.

Referring again to FIG. 21A, in one embodiment of the present invention second external optical surface 1135 of extraction chamber 1105 and external optical surfaces of first extraction port 1110 and second extraction port 1115 are positioned such that that are in the depth of field provided by a light collection element and two-dimensional detector (no shown in FIG. 21A). Exemplary second external optical surface 1135 of extraction chamber 1105 and external optical surfaces of first extraction port 1110 and second extraction port 1115 occupy substantially the same plane 1170. In this context the expression "substantially the same plane" includes deviations from an absolutely coplanar orientation less than or equal to about 0.1 inches Preferably for some applications, second external optical surface 1135 of extraction chamber 1105 and external optical surfaces 1146 and 1147 of extraction port 1110 and second extraction port 1115 can be positioned in a common plane corresponding to the focal plane of a fixed position CCD or CMOS camera equipped with a fixed focus lens system in optical communication with optical cell 1100. This optical configuration allows for simultaneous imaging and sensitive optical characterization of the blood separation region 1126, first extraction port 1110 and second extraction port 1115. An advantage of this optical configuration is that is allows simultaneous measurements of the position of phase boundaries in the blood separation region 1126 and the composition of blood components extracted through first and second extraction ports 1110 and 1115.

Optical cell 1100 can also comprise additional elements to facilitate a number of optical measurements. First, optical cell 1100 can be provided with a variety of calibration markers. Calibration markers and optical surfaces 1135, 1146 and 1147 can be positioned in common plane 1170, such as a plane corresponding to the focal plane of a fixed position CCD or CMOS camera equipped with a fixed focus lens in optical communication with optical cell 1100. Calibration makers can be positioned on optical cell 1100 itself, for example on the closest of ribs 1141 to plane 1170, or on a device or device component for holding optical cell 1100 in a density centrifuge, such as a filler device component. In one embodiment, calibration markers comprise markers for calibrating the physical dimensions and spatial orientation of a collected image, for example one or more two dimensional shapes such as bars having selected physical dimensions and spacing. In one embodiment, calibration markers comprise markers for calibrating intensities of collected images, for example one or more two dimensional forms having selected absorption, scattering and reflection characteristics. In one embodiment, calibration markers comprise markers for calibrating the colors of collected images, for example one or more colored forms such as a color wheel.

Optical cells of the present invention may further comprise one or more selectively absorbing, reflecting, scattering, focusing and/or collimating regions. In one embodiment, optical cells of the present invention have one or more masked regions that are capable of substantially preventing transmission of light by absorbing, scattering and/or reflecting an incident beam. In one embodiment, optical cells of the present invention have one or more curved surfaces for selectively adjusting the spatial characteristics of an incident beam, for example by focusing or collimating an incident beam.

Optical cells of the present invention can be fabricated from a wide range of at least partially transmissive materials including but not limited to polymers, plastics, thermosets and thermoplastics. Optical cells comprising one or more amorphous polymers are preferred in some embodiments because they provide for better transmission of incident light than corresponding crystalline materials. Exemplary materials useful for fabricating optical cells of the present invention include, but are not limited to, amorphous polyvinyl chloride, polycarbonate, and polyethylene terephthalate glycol (PETG) and polyethylene terephthalate (PET thermoplastic).

EXAMPLE 5

System for Monitoring and Controlling Blood Processing via Density Centrifugation The present invention includes systems for monitoring and controlling blood processing via density centrifugation that are capable of providing simultaneous real time measurements of the positions of phase boundaries between optically differentiable blood components relative to calibration markers and the compositions and/or fluxes of separated and extracted blood components. A system of the present invention exhibiting excellent sensitivity, mechanical ruggedness and reliability comprises a fixed position CCD camera equipped with a fixed focus lens, a top pulsed LED (light emitting diode) light source and a bottom pulsed LED light source. Use of a fixed position CCD camera equipped with a fixed focus lens system provides a system exhibiting high mechanical stability with respect to maintaining optical alignment, which avoids the need for periodic adjustments of the optical path lengths illumination and detection beams. In addition, use of top and bottom pulsed LED light sources provides considerable flexibility in the wavelength distributions and intensities of illumination light beams directed onto the blood processing system and subsequently detected. Further, use of top and bottom pulsed LED light sources also provides accurate and reproducible temporal characteristics of illumination pulses useful for generating high optical quality images of a rotating optical cell of a separation chamber.

Figure 22:
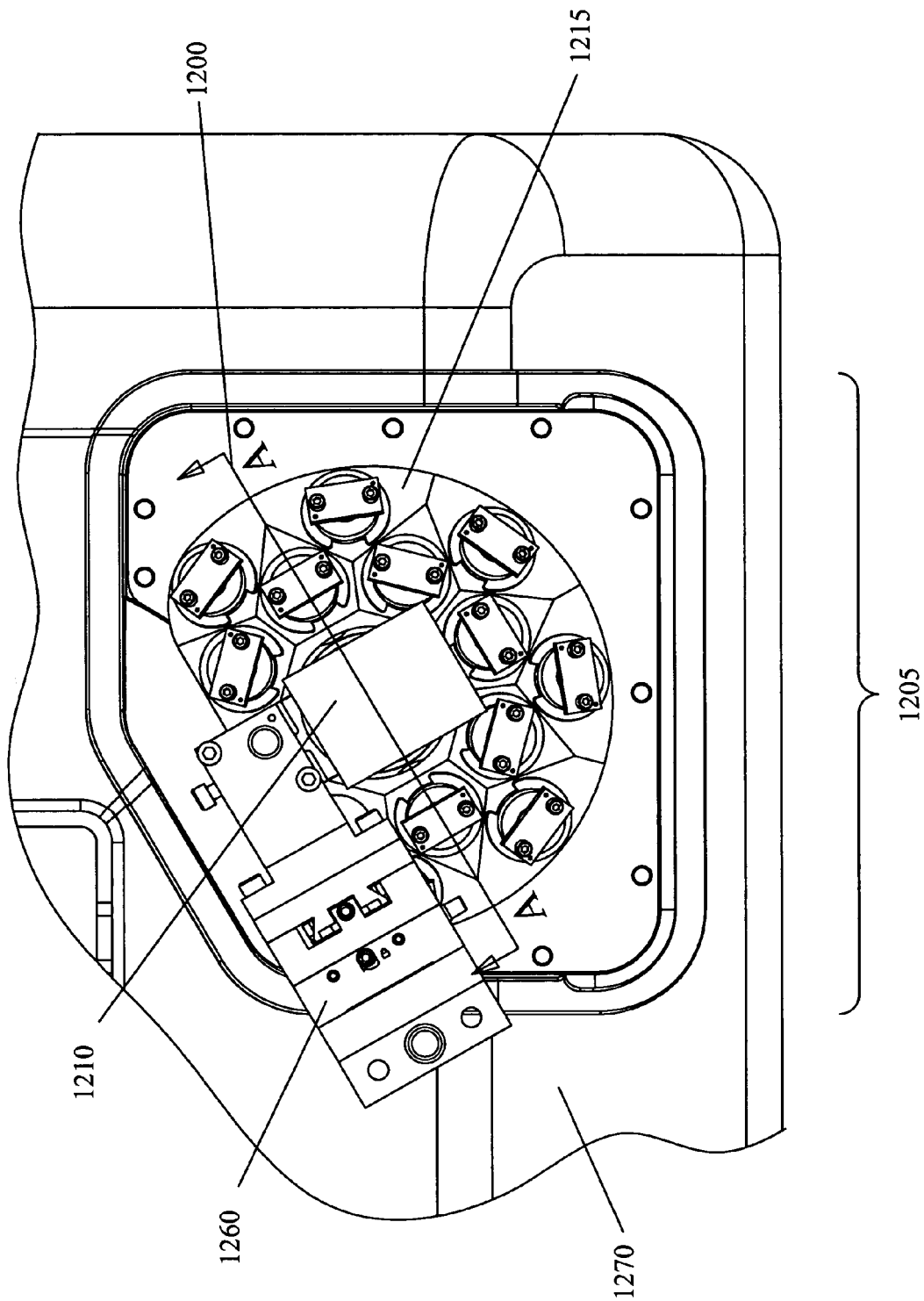
FIG. 22 is a top view of an optical monitoring and control system of the present invention well suited for blood processing via density centrifugation.
Figure 23:
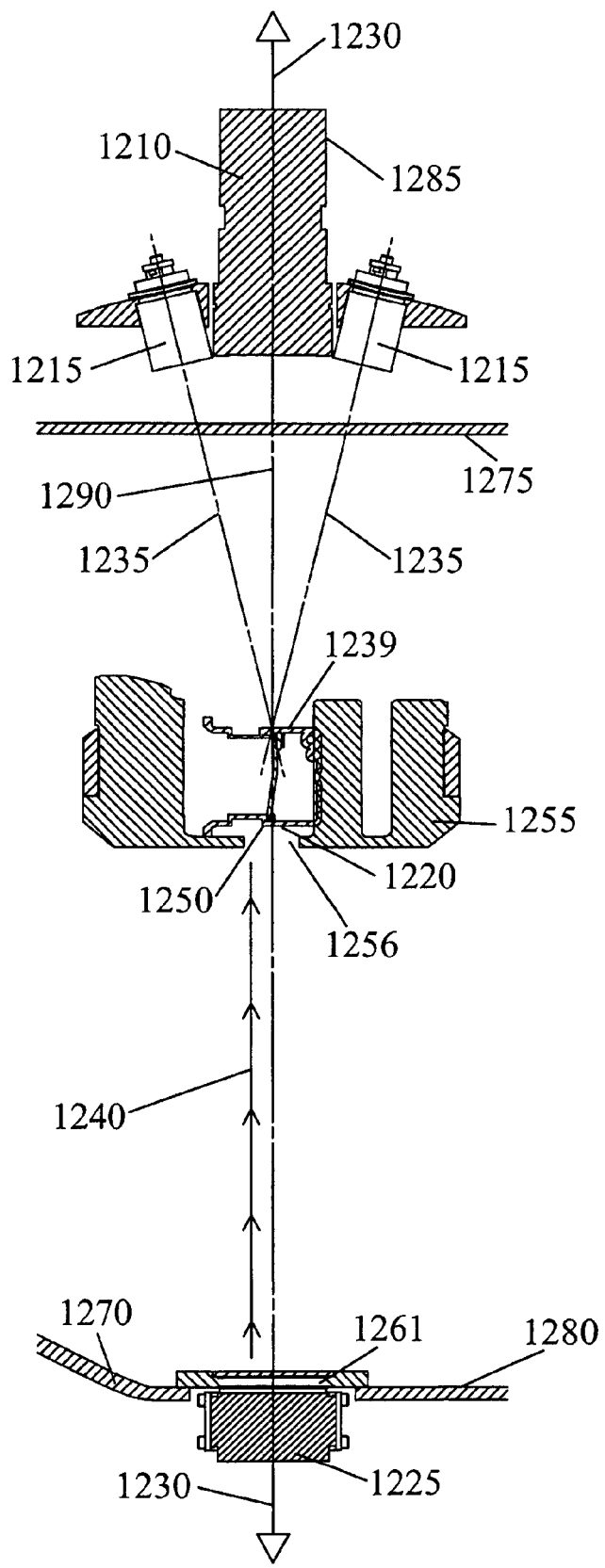
FIG. 23 is a cut away view corresponding to cut away axis 1200 indicated in FIG. 22.
Figure 24:
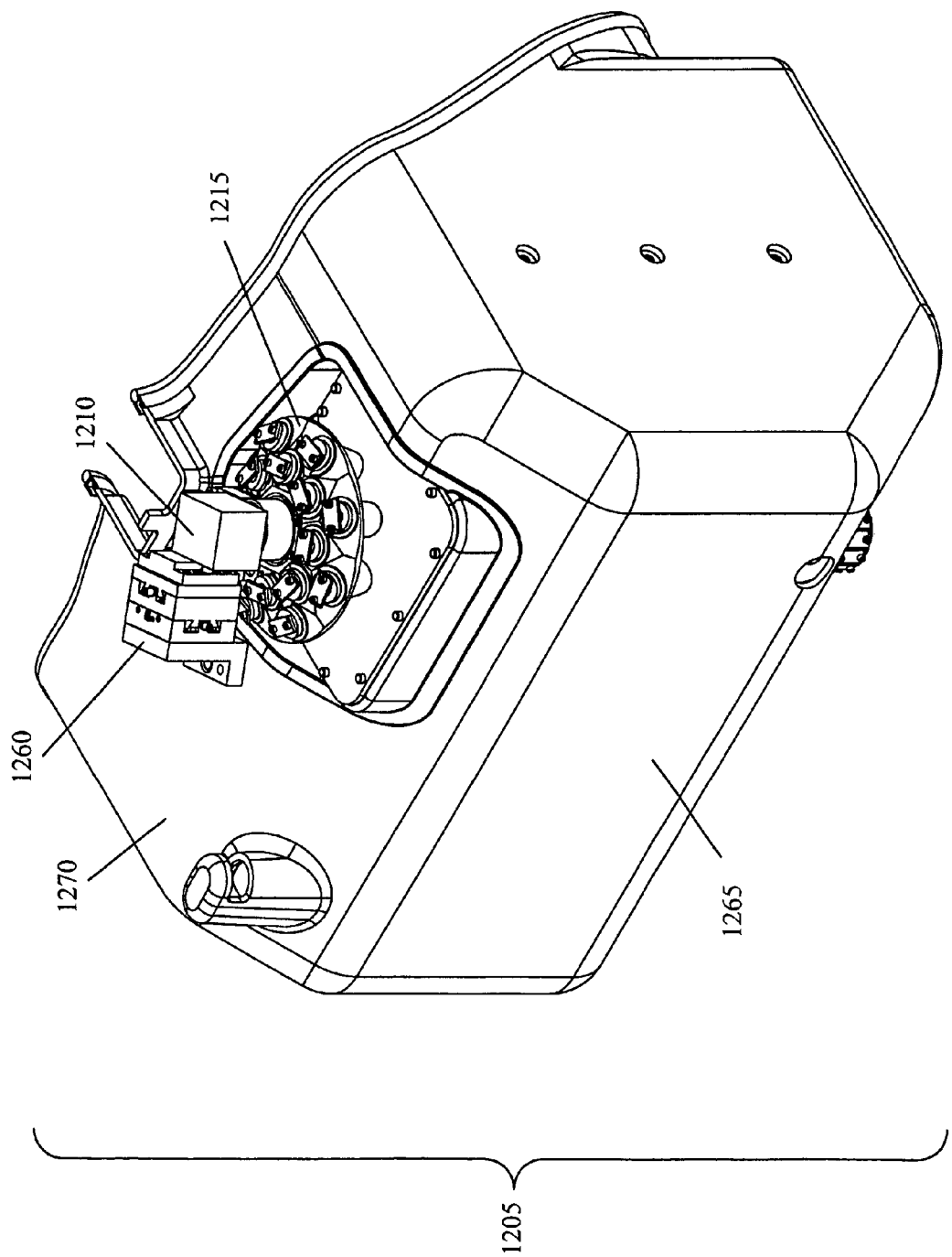
FIG. 24 is a side view of the optical monitoring and control system illustrated in FIGS. 22 and 23.

FIG. 22 is a top view of an optical monitoring and control system of the present invention well suited for blood processing via density centrifugation. FIG. 23 is a cut away view corresponding to cut away axis 1200 indicated in FIG. 22. FIG. 24 is a side view of the optical monitoring and control system illustrated in FIGS. 22 and 23. The illustrated optical monitoring and control system 1205 comprises CCD camera equipped with a fixed focus lens system 1210, an optical cell 1220, a top pulsed LED light source 1215, and a bottom pulsed LED light source 1225. As illustrated in FIG. 23, CCD camera with a fixed focus lens system 1210 is in optical communication with optical cell 1220 and positioned to intersect optical axis 1230. Top pulsed LED light source 1215 is in optical communication with optical cell 1220 and is positioned such that it is capable of directing a plurality of collimated upper illumination light beams 1235, propagating along propagation axes that intersect optical axis 1230, onto the top side 1239 of optical cell 1220. Bottom pulsed LED light source 1225 is also in optical communication with optical cell 1220 and is positioned such that it is capable of directing a plurality of collimated bottom illumination light beams 1240, propagating along a propagation axis parallel to optical axis 1230, onto the bottom side 1250 of optical cell 1220. Optionally, the top pulsed LED light source, bottom pulsed LED light source or both can be replaced with one or more pulsed xenon lamps for generating upper illumination light beams 1235, bottom illumination light beams 1240 or both. Use of pulsed xenon lamps is desirable for application requiring very intense upper and lower illumination light beams.

Optical cell 1220 is an integral component of a separation chamber of a density centrifuge and is held in position a selected distance from the density centrifuge's central rotational axis by filler 1255. Filler 1255 and optical cell 1220 are configured in a manner such that both are capable of free rotation about the central rotational axis of the density centrifuge. In the embodiment shown in FIGS. 22, 23, 24, filler 1255 has an aperture 1256 of selected dimensions for passing at least a portion of bottom illumination light beams 1240. Alternatively, aperture 1256 can comprise a stand alone optical element positioned along optical axis 1230 between bottom pulsed LED light source 1225 and optical cell 1220 or can be a integral component of optical cell 1220 itself. Aperture 1256 can be any shape including, but not limited to, circular, square, rectangular, polygonal, romboidal, ellipsoidal or any combination of these shapes. Use of aperture 1256 in the present invention is useful for preventing detector saturation cause by too much light impinging on the sensing surface of the CCD camera and is useful for enhancing contrast with respect to areas of interest. Optionally, filler 1255 can also be equipped with other optical elements (not shown) for adjusting the spatial characteristics or wavelength distribution of bottom illumination light beams 1240, such as optical filters, band pass filters, cut off filters and/or diffusers.

In an exemplary embodiment, top pulsed LED light source 1215 is positioned about 4.26 inches from the top 1239 of optical cell 1220, and bottom pulsed LED light source 1225 is positioned about 7.47 inches from the top 1239 of optical cell 1220. In the exemplary embodiment shown in FIG. 23, CCD camera with fixed focus lens system 1210 is positioned such that the focal plane of fixed focus lens system is substantially co-planar with selected optical surfaces of optical cell 1220, such as optical surfaces corresponding to an interface monitoring region, calibration markers, one or more extraction ports and one or more inlets. In this embodiment, the CCD camera is also separated from the center of the fixed focus lens system by a distance along optical axis 1230 such that an image corresponding to selected optical surfaces of optical cell 1220 is provided on the sensing surface of the CCD camera. An advantage of this optical configuration is that it allows two dimensional distributions of light intensities comprising images of top 1239 of rotating optical cell 1100 to be measured and analyzed in real time.

CCD camera with fixed focus lens system 1210 is held in a fixed position a selected distance along optical axis 1230 from top 1239 of optical cell 1220 by mounting assembly 1260. The mounting assembly 1260, shown in FIGS. 22-24, comprises a bracket capable of maintaining a fixed position and orientation of CCD camera with fixed focus lens system 1210. Mounting assembly 1260 can also comprise a 2-axis locking translation stage, optionally with a 2 axis titling mechanism, capable of selectively adjusting the relative orientation and position of the camera and fixed focus lens system with respect to optical cell 1220.

As shown in FIGS. 22-24, optical monitoring and control system 1205 is integrated directly into a density centrifuge blood processing device 1265. To provide good mechanical stability of optical monitoring and control system 1205, mounting assembly 1260 is directly affixed to a frame member (not shown in FIGS. 22-24) supporting housing 1270 of density centrifuge blood processing device 1265. In one embodiment, bottom pulsed LED light source 1225 is also be affixed to a frame member (not shown in FIGS. 22-24) supporting housing 1270 of density centrifuge blood processing device 1265 by means of an additional mounting assembly 1261. Top pulsed LED light source 1215 is secured to CCD camera with fixed focus lens system 1210, as shown in FIGS. 22-24. Alternatively, top pulsed LED light source 1215 can be directly affixed to a frame member (not shown in FIGS. 22-24) supporting housing 1270 of density centrifuge blood processing device 1265 by means of an additional mounting assembly. Mounting assemblies useful in the present invention comprise any fastening means know in the art, such as clamps, brackets, connectors, couplers, additional housing elements and all known equivalents, and can be affixed to frame members supporting housing 1270 by any means known in the art including the use of bolts, fasteners, clamps, screws, rivets, seals, joints, couplers or any equivalents of these known in the art.

Referring to the cross section shown in FIG. 23, first transparent plate 1275 is provided between CCD camera with a fixed focus lens system 1210 and optical cell 1220, and second transparent plate 1280 is provided between bottom pulsed LED light source 1225 and optical cell 1220. First and second transparent plates 1275 and 1280 physically isolate CCD camera with a fixed focus lens system 1210, top pulsed LED light source 1215 and bottom pulsed LED light source 1225 from optical cell 1220 so that these components will not contact a sample undergoing processing in the event of sample leakage from the separation chamber. In addition, first and second transparent plates 1275 and 1280 minimize degradation of CCD camera with a fixed focus lens system 1210, top pulsed LED light source 1215 and bottom pulsed LED light source 1225 due to unwanted deposition of dust and other contaminants that can be introduced to the system upon rotation of the separation chamber and filler. Further, first and second transparent plates 1275 and 1280 also allow a user to optimize the alignment of the camera with fixed focus lens system, top pulsed LED light source and bottom pulsed LED light source without exposure to a blood sample in the separation chamber. First and second transparent plates 1275 and 1280 can comprise any material capable of transmitting at least a portion of upper and bottom illumination light beams 1235 and 1240. Exemplary materials for first and second transparent plates 1275 and 1280 include, but are not limited to, glasses such as optical quality scratch resistant glass, transparent polymeric materials such as transparent plastics, quartz and inorganic salts.

Figure 25:
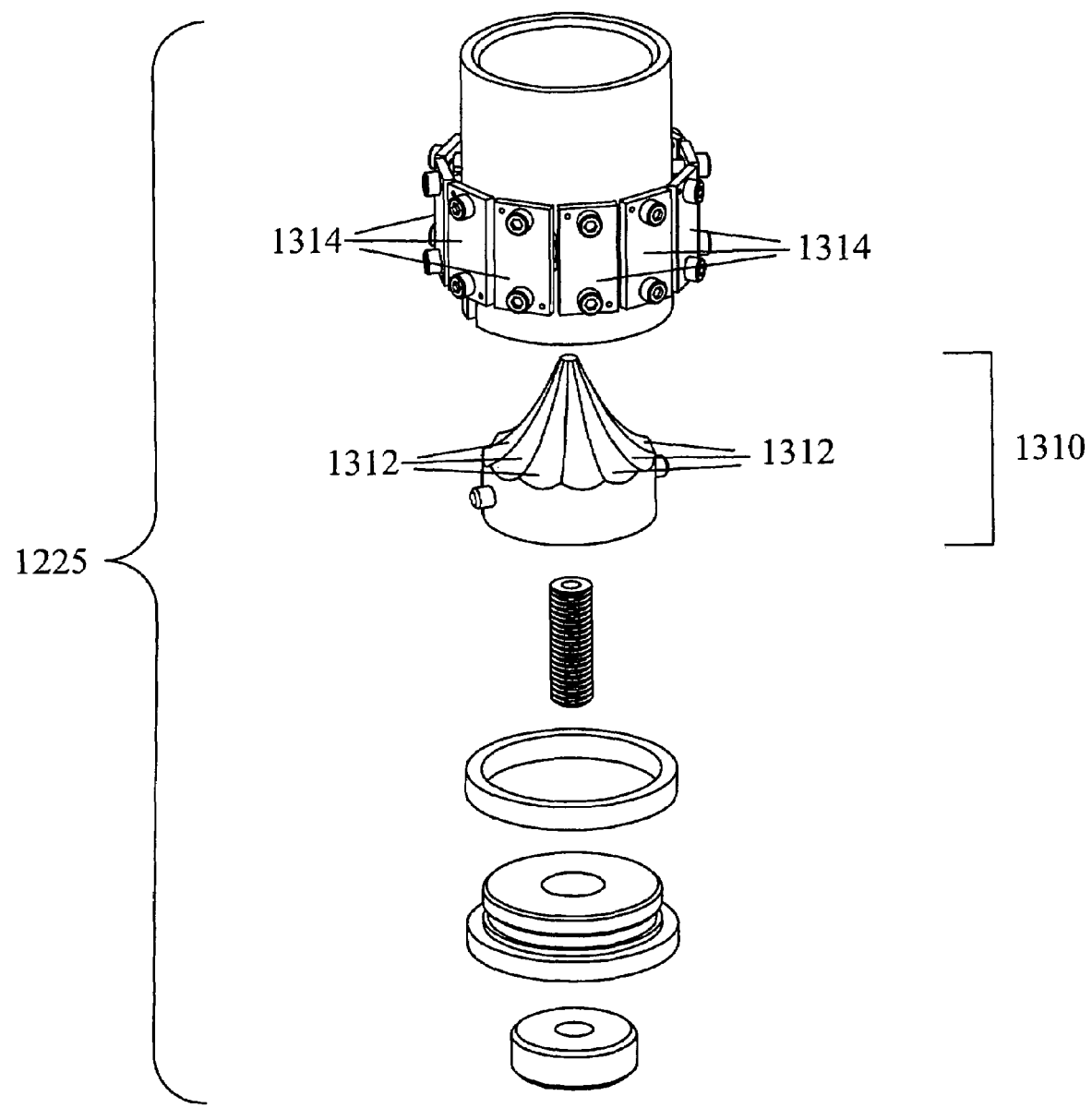
FIG. 25 provides a schematic diagram of an exploded, side view of a bottom pulsed LED source useful in the methods and devices of the present invention.

Top pulsed LED light source 1215 and bottom pulsed LED light source 1225 in the optical monitoring and control system illustrated in FIGS. 22-24 each comprise a plurality of LEDs, such as a LED array light source. Top pulsed LED light source 1215 comprises 12 LEDs each equipped with parabolic reflectors to provide beam collimation. Bottom pulsed LED light source 1225 also comprises 12 LEDs and a collimating optical element, such as one or more lenses, parabolic reflectors or a combination of these elements. FIG. 25 provides a schematic diagram of an exploded, side view of a bottom pulsed LED source 1225 useful in the methods and devices of the present invention. The illustrated pulsed LED light source comprises a collimating optical element 1310 in optical communication with elements 1314 of a LED array. As shown in FIG. 25, collimating optical element 1310 is a multifaceted parabolic reflecting and collimating element comprising a plurality of contoured reflective surfaces 1312, each of which is positioned in optical communication with a LED light element 1314. Contoured reflective surfaces 1312 have a modified parabolic contour profile in one embodiment of the present invention useful for monitoring an controlling blood processing. Depending on the contour profile selected for contoured reflective surfaces 1312, collimating optical element 1310 may be configured to provide a plurality of incident beam propagating along propagation axes that are approximately parallel or a plurality of incident beam propagating along propagation axes which are not parallel. The embodiment illustrated in FIG. 25 is useful for generating a plurality of incident beams that may be directed onto the bottom side 1250 surface of the optical cell 1220.

LEDs useful for the top and bottom pulsed LED sources 1215 and 1225 can be red LEDs, green LEDs, white LEDs or any combination of these. In an exemplary embodiment, top and bottom pulsed LED source 1215 and 1225 each comprise 4 red LEDs, 4 green LEDs and 4 white LEDs. LEDs useful in the present invention provide collimated beams having intensities large enough allow measurement of two dimensional intensity distributions comprising to images of optical cell 1220. In an embodiment of the present invention, LED drive circuitry is optionally positioned proximate to top and/or bottom LED sources to optimize device performance.

Top pulsed LED light source 1215 and bottom pulsed LED light source 1225 are capable of providing synchronized light pulses having accurately selectable temporal characteristics. Pulse widths of light pulses useable in the present invention depend on the rotational velocity of the density centrifuge. Typically, the smaller the pulse width of the light pulse the less blurring of the optical image corresponding to the acquired two dimensional distribution of light intensities. However, larger pulse widths allow more photons to be detected by the camera and, thus, provide enhanced signal to noise ratios. For a rotational velocity equal to about 3000 RPM, pulse widths less than about 8 microseconds are useful for minimizing blurring of the image of the optical cell generated. Exemplary light pulses useful for some applications of the present invention have pulse widths selected over the range of about 1 microsecond to about 50 microseconds.

In one embodiment, CCD camera with a fixed focus lens system 1210 comprise a monochrome or color CCD camera positioned a fixed, selected distance from a fixed focus lens system. CCD camera and fixed focus lens system can be contained in a housing 1285 capable of maintaining the selected separation distance between these elements and also capable of minimizing detection of unwanted scattered light. Housing 1285 can be equipped with one or more fixed spacers or selectively adjustable spacers for establishing and maintaining a selected distance between the CCD camera and the fixed focus lens system. An exemplary fixed focus lens system comprises a plurality of spherical lenses, cylindrical lenses, spacers or any combination of these elements. An exemplary CCD camera is the "Flea" manufactured by Point Grey Research, Inc. and has a pixel area equal to about 1024 pixels by 768 pixels. An exemplary lens comprises a F 2.8 fixed focal length lens system having a focal length of 28 millimeters manufactured by Schneider Optics, Inc. This combination of exemplary optical components provides a field of view equal to about ⅜ inch by ½ inch and a depth of field selected over the range of about 1/16 inch to about ½ inch. This field of view and depth of field allows for measurement of two dimensional distributions of light intensities comprising images of optical cell 1220 useful for monitoring and controlling the positions of phase boundary positions in an interface region and the compositions of cellular material exiting one or more extraction port. Use of a CCD camera equipped with a fixed focus lens system enhances the mechanical stability of the system and is useful for maintaining selected relative orientations and positions of the CCD camera, fixed focus lens system and the optical cell. This aspect of the present invention provides the system with the ability to make highly reproducible measurements of the positions of phase boundary layers between optically differentiable, separated blood components in an interface region and the compositions of separated blood components exiting the optical cell through one or more extraction ports.

FIG. 23 also shows the optical path lengths provided by the present optical geometry. Top pulsed LED light source 1215 generates a plurality of pulsed collimated upper illumination light beams 1235 which propagate along propagation axes that intersect optical axis 1230. At least a portion of upper illumination light beams 1235 passes through transparent plate 1275 and are directed onto the top side 1239 of optical cell 1220. A portion of upper illumination light beams 1235 is scattered by optical cell 1220, one or more separated blood components therein and/or filler 1255. Bottom pulsed LED source 1215 generates a collimated bottom illumination light beams 1240 which propagates along a propagation axis substantially parallel to optical axis 1230. At least a portion of bottom illumination light beams 1240 passes through transparent plate 1280 and is directed onto the bottom side 1250 of optical cell 1220. A portion of bottom illumination light beams 1240 is transmitted through optical cell 1220 and one or more separated blood components therein. Light transmitted through optical cell 1220 can correspond to an interface monitoring region, one or more inlets, one or more extraction ports, one or more calibration markers or any combination of these.

Light 1290 transmitted and/or scattered by optical cell 1220 is collected by fixed focal length lens system and imaged onto the sensing surface of the CCD camera. In this manner, a two dimensional distribution of light intensities is measured by CCD camera that corresponds to an image of at least a portion of optical cell 1220, such as the top 1239 of optical cell 1220. Detection of scattered light corresponding to the upper illumination light beams 1235 is primarily used for system calibration, proximity identification and translational sensor tracking. Detection of transmitted light corresponding to the bottom illumination light beams 1240 is primarily used for measurement of the position of one or more phase boundary layers of optically differentiable separated blood components in optical cell 1220 and for measurement of the composition and flux of separated blood components exiting one or more extraction ports of optical cell 1220. Detecting transmitted and scattered light arising from both top and bottom illumination maximizes the amount of information that can be extracted from an acquired two dimensional distribution of light intensities and enhances the multifunctional capabilities of optical monitoring and control systems of the present invention.

Optionally, optical monitoring and control system 1205 may further comprise one or more additional light detectors useful for optimizing the light levels of top and bottom pulsed LED light sources 1215 and 1225. In one embodiment, an additional light detector comprising a photodiode is provided which is capable of measuring scattered light from bottom pulsed LED light source 1225. Use of an additional light detector capable of scattered light from bottom pulsed LED light source 1225 is useful for trouble shooting and error handling aspects of the present invention.

The CCD camera is capable of generating one or more output signals corresponding to the measured two dimensional distribution of light intensities. Output signals are sent to one or more centrifuge device controllers (not shown in FIGS. 22-24), such as a computer or processor, capable of analyzing the acquired two dimensional distributions of transmitted and/or scattered light intensities and adjusting important operating conditions which affect separation conditions and the composition of extracted blood components. Selectively adjustable operating conditions include, but are not limited to, the rotational velocity of the centrifuge, the flow rates of one or more inlet pumps, and the flow rates of one or more extraction pumps, or any combination of these.

The optical monitoring and control system 1205 depicted in FIGS. 22-24 is a pulsed optical system, whereby two dimensional intensity distributions corresponding to optical cell 1220 are acquired as it is rotated about the central rotational axis of the density centrifuge 1265. Two dimensional intensity distributions can be acquired for every full rotation of optical cell 1220 or can be acquired for selected rotations of optical cell 1220, such as every other full rotation. Acquiring two dimensional intensity distributions for every other rotation of optical cell 1220 is beneficial for some applications because it avoids the need for costly CCD cameras capable of collecting more than about 30 frames per second and also minimizes spatial indication, calibration and optical imaging problems associated with reproducible instrument jitter observed upon rotation of the separation chamber.

To generate two dimensional intensity distributions corresponding to good images of optical cell 1220, top and bottom illumination pulse, camera shutter and gating settings and the rotation of optical cell 1220 of a separation chamber of a density centrifuge must be accurate synchronized. Accurate synchronization of these elements allows two dimensional images of transmitted and/or scattered light intensities comprising high optical quality images of the optical cell may be measured for each full rotation or for selected rotations. In the present invention, the rotational position of components of the density centrifuge and/or monitoring and control system, such as the optical cell or separation chamber, is accurately measured using an encoded motor system, as well known in the art. In an exemplary embodiment, density centrifuge 1265 is provided with any optical sensor capable of reading a plurality of markers on a rotating element of the density centrifuge. This configuration allows for real time measurements of the rotational position of the optical cell, preferably measurements of rotational position accurate to about 0.09 degrees. This configuration also provides real time measurements of the rotational position of the optical cell when the rotational velocity changes, such as during spin up or spin down of the density centrifuge.

The encoded motor system is also capable of generating output signals in real time corresponding to the rotational position of components of the density centrifuge and/or monitoring and control system, such as the optical cell or separation chamber. In an exemplary embodiment, these output signals are provided as input to a synchronization and timing controller capable of sending one or more trigger signals to the top pulsed LED light source, bottom pulsed LED light source and the CCD camera. Trigger signals provided by the synchronization and timing controller to these device components include the trigger location (i.e. the time or rotational position for initiating to a light pulse), the trigger frequency (i.e. for which rotations should light pulses be generated), the pulse width setting (duration of light pulse) and the delay setting (i.e. time between when the trigger signal is received and when the light pulse is to be initiated). LED elements in top and bottom pulsed LED light sources and camera shutter and gate setting can be accurately triggered at times corresponding to a desired rotational position of the density centrifuge using trigger signals generated by the synchronization and timing controller. Selection of the rotational position corresponding to the trigger signal allows the observation region to be selectively adjusted in the present invention. In this manner, a plurality of selected regions of the optical cell, separation chamber and other components of the density centrifuge are optically probed.

In an exemplary embodiment, the exposure time of the CCD camera is determined by the pulse width of the light pulses generated by the top and bottom pulsed LED light sources, rather than by the gating setting or shutter of the CCD camera. In one embodiment, the shutter of the CCD camera is open a few orders of magnitude longer than the light pulse duration without having significant background noise affects. As the pulse widths of light pulses generated by LED light sources can be controlled very accurately, this aspect of the present invention eliminates the need of costly CCD cameras providing very accurate gating corresponding to short exposure times.

Figure 26:
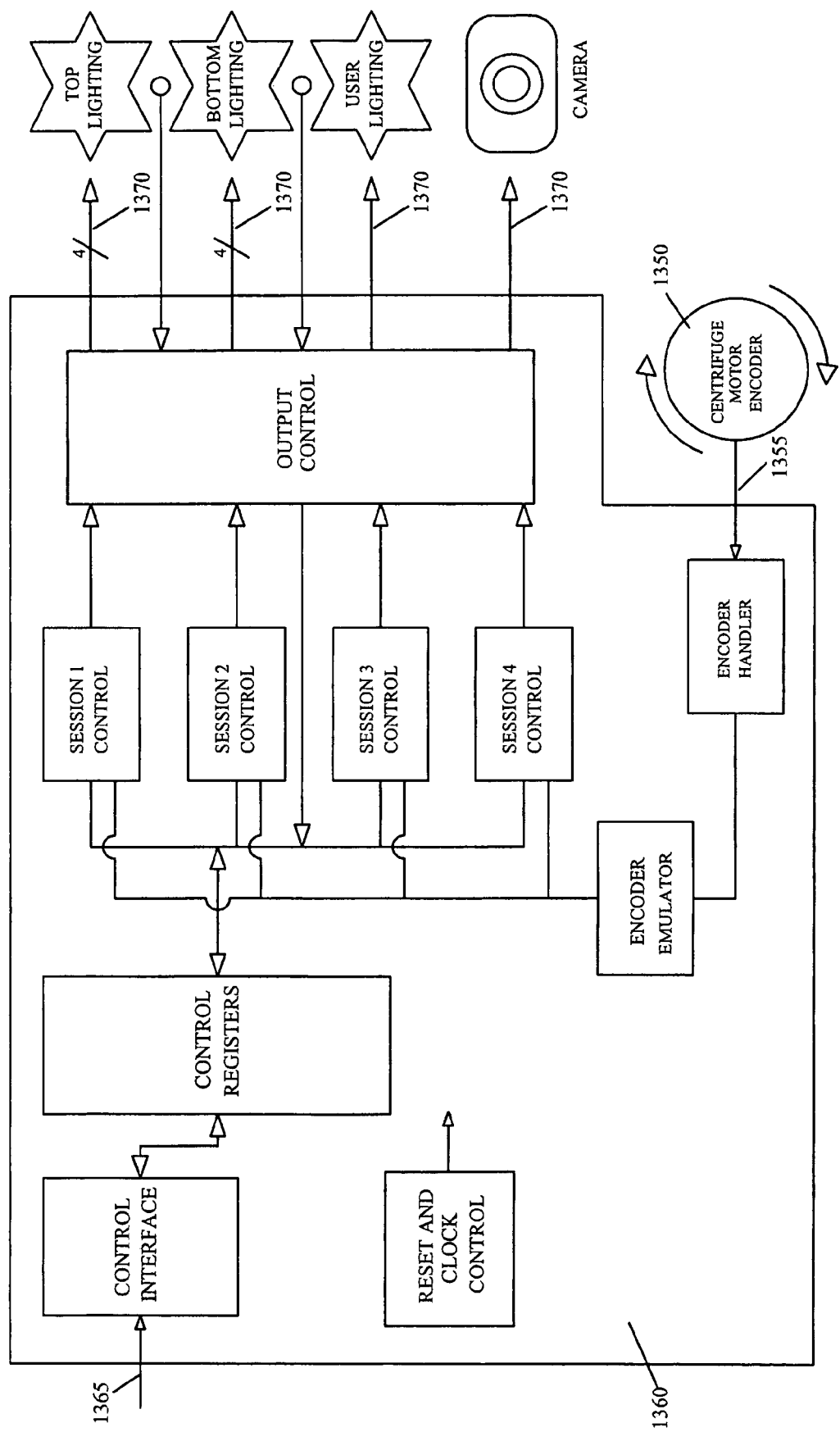
FIG. 26 shows a functional flow diagram representing a method of synchronizing light pulses generated by top and bottom pulsed LED light sources trigger and trigger delay settings.

FIG. 26 shows a functional flow diagram representing a method of synchronizing light pulses generated by top and bottom pulsed LED light sources and camera shutter and gate settings. As illustrated in FIG. 26, encoded motor system 1350 generates one or more output signals 1355 corresponding to the rotational position of the optical cell. Output signals 1355 are received as input to the synchronization and timing controller 1360. Synchronization and timing controller 1360 is also configured to receive control signals 1365 from a device controller. Control signals 1365 and output signals 1355 are processed by synchronization and timing controller 1360, and serve as the basis of a plurality of trigger signals 1370 which are sent to the top pulsed LED light source, the bottom pulsed LED light source and the CCD camera. Optionally, one or more trigger signals are also be used to adjust the lighting in the density centrifuge chamber to allow a user to visually assess the state of the density centrifuge during processing. An advantage of this aspect of the present invention is that timing and synchronization of light pulses and camera settings are handled by the synchronization and timing controller 1360 without expenditure of other system resources, such as processing time of the device controller.

Use of LED light sources in the present invention is beneficial because these light sources are small, light weight and have relatively low power consumptions compared to many conventional non-LED light sources. LED light sources also exhibit long operating lifetimes and uniform radiant outputs. In addition, LED light sources are capable of pulse operation generating discrete pulse having accurately selectable temporal characteristics such as pulse width and initiation time. Pulse LED sources also are capable of generating pulses having substantially uniform intensities and wavelength distributions. Use of LED is also preferred for some applications of the present invention because it provides good control of the wavelength distribution of the upper and/or lower illumination beams. The present invention includes embodiments, wherein the wavelength distribution of top and bottom illumination beams is selectively adjustable by blending the output of LEDs having different colors, such as red, green and white LEDs. In these embodiments, the wavelength distributions of top and bottom illumination beams are be independently selected on a shot per shot basis to optimize a desired optical measurement, such as the measurement of the position of phase boundaries between optically differentiable blood components and/or the compositions of extracted blood components passing through an extraction port.

Optical monitoring and control systems of the present invention having a fixed position camera and fixed focus lens system are capable of providing very sensitive measurements of the positions of phase boundaries between optically differentiable separated blood components. For example, systems of the present invention having a fixed position camera and fixed focus lens system are capable of measuring the position of the phase boundary between red blood cell containing components and a buffy coat layer and the position of the phase boundary between a plasma containing components and a buffy coat layer to within 0.0005+0.0002 inches.

Figure 27:
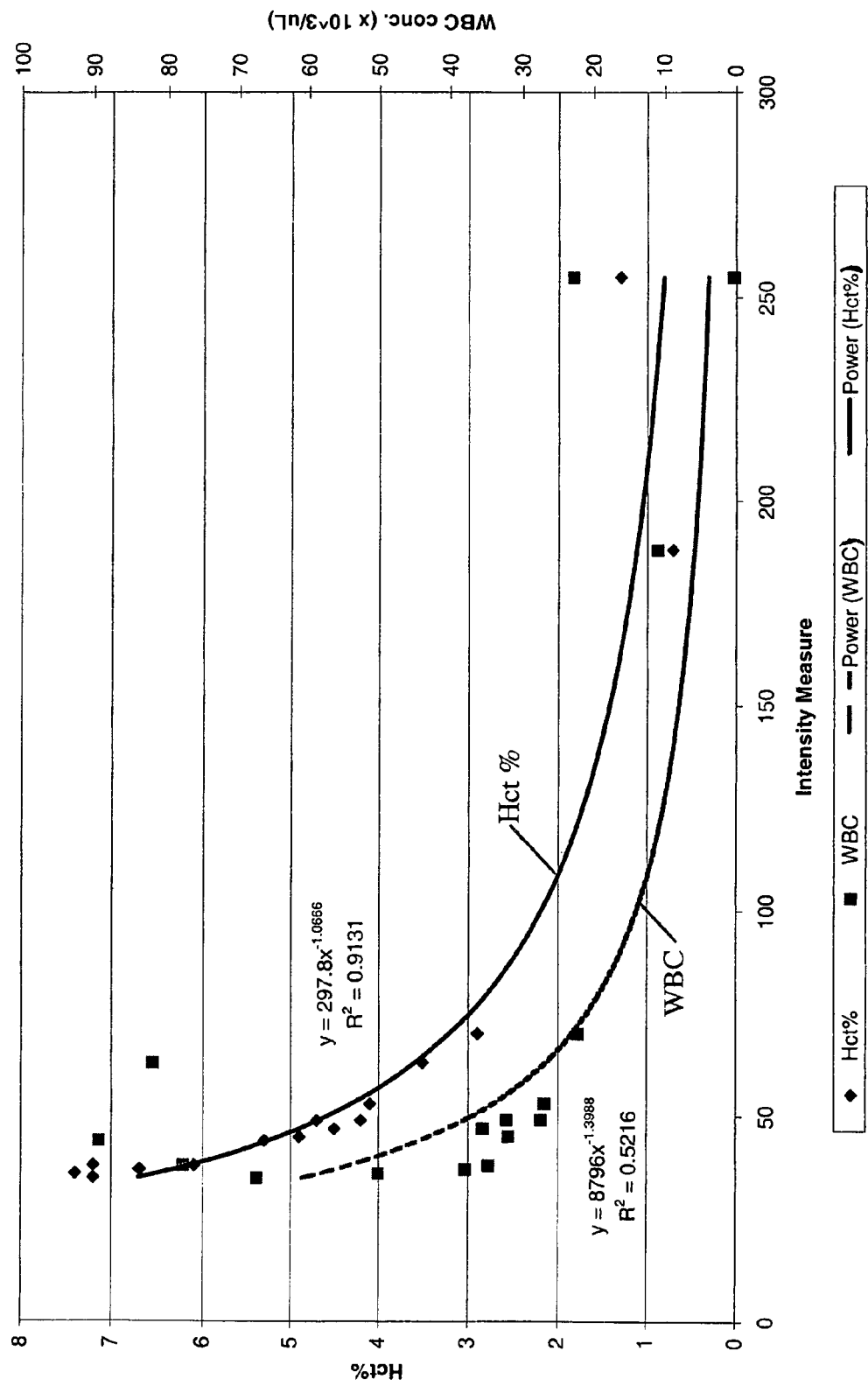
FIG. 27 provides plots of measurements of the white blood cell concentration (square markers) and hematocrit (diamond markers) of a separated blood component passing through an extraction port as function of the measured average intensity of light transmitted through the extraction port.

Optical monitoring and control systems of the present invention having a fixed position camera and fixed focus lens system are capable of providing very sensitive measurements of the compositions and fluxes of separated blood components through an extraction port. Systems of the present invention having a fixed position camera and fixed focus lens system are capable of measuring the hematocrit of an extracted blood component, such as a white blood cell containing component, passing through an extraction port to within about 1%. In addition, the two dimensional distribution of the intensities of light transmitted through an extraction cell also provides an accurate measurement of the cellular composition of an extracted blood component. FIG. 27 provides plots of the white blood cell concentration (square markers) and hematocrit (star markers) of a separated blood component passing through an extraction port as function of the measured average intensity of light transmitted through an observation region position on the extraction port. As illustrated by the plots the average intensity of transmitted light is strongly inversely correlated with both the white blood cell concentration and the hematocrit. Statistical analysis of the plots in FIG. 27 yields the following algorithms relating the average intensity of transmitted light to the white blood cell concentration and the hematocrit:

$$Hct(\%) = 297.8 \times (I)^{-1.0666}; \quad (V)$$

$$\text{Conc. } WBC = 8796 \times (I)^{-1.3988} \quad (VI)$$

wherein Hct(%) is the hematocrit, conc. WBC is the concentration of white blood cells multiplied by a factor of 1000 in units of number per microliter and I is the average intensity of light transmitted through the extraction port.

EXAMPLE 6

Density Centrifugation Methods for Processing Blood

The present invention provides methods for processing blood and blood components. Methods of the present invention are applicable for processing blood and blood components having a wide range of compositions, which make them especially well suited for therapeutic procedures for patient pools that often exhibit a large range of blood compositions. In addition, the methods of the present invention are particularly well suited for blood processing applications wherein the composition of a patient's extracted blood undergoes significant variation during a selected procedure.

1. Blood Processing Based on Optical Characterization of the Composition of Extracted Blood Components In one embodiment, the present invention provides a method of processing blood capable of providing extracted blood components having a selected composition. In the context of this description the term "composition" relates to the purity, cell-type, concentration and/or speciation of cellular and/or noncellular blood components in an extracted blood component. An advantage of this aspect of the present invention is that it is capable of optimizing a particular blood processing therapy, such as a blood component reduction therapy (e.g. leukapheresis therapy or therapeutic platelet depletion) or capable of providing blood components having compositions optimized for a particular therapeutic application, such as an infusion therapy.

In one embodiment, a user selects a desired blood component to be separated and extracted, and selects an optimal composition or range of compositions of the extracted blood component for an intended therapeutic application. The selected type of blood component and composition is then provided to a device controller of the present invention as input. The device controller configures and adapts the blood processing device to achieve separation and extraction conditions necessary for producing a blood component having the desired composition. In the context of blood processing via density centrifugation, for example, the optical monitoring and control system measures the concentration and type of an extract blood component in real time and iteratively adjust operating conditions, such as the flow rates of the inlet pump, flow rates of extraction pumps and rotational velocity of the centrifuge, to achieve and maintain the desired composition of an extracted blood component. The methods of this aspect of the present invention, however, are not limited to blood processing via density centrifugation and, are also applicable to processing via a range of filtration and diffusion-based separation techniques.

This aspect of the present invention is particularly useful for separating and extracting a white blood cell component of blood using density centrifugation. Using the present methods, images of an extraction port corresponding to a separated white blood cell component are be acquired and analyze in real time to provide a measurement of the purity of the extracted component. The measured composition is then be compared to the user selected composition, such as a selected concentration or purity of white blood cells. If the measured composition is within a desired range of the selected composition, operating conditions of the density centrifuge are maintained as long as the composition of the extract portion does not change so as to be outside of the desired range. If the measured composition is not within a desired range of the selected composition, the operating conditions are iteratively adjusted in a manner bringing the observed composition closer to the selected composition. In one embodiment, the concentration of red blood cells in the extracted white blood cell component is measured in real time and compared to a calculated red blood cell concentration corresponding to the selected white blood cell concentration. This exemplary method exploits well known relationships between the abundance of red blood cells in a white blood cell containing component generated by density centrifugation and the observed white blood cell concentration. In another method, the concentration of white blood cells is directly measured using the present optical monitoring methods and used to control blood processing. To facilitate direct monitoring and characterization of white bloods cells in the absence of red blood cells, operation conditions of the centrifuge can be modified to provide a buffy coat layer extending a larger thickness along the separation axes, such as by the addition of an intermediate density fluid or by selection of appropriate rotational velocities.

2. Coarse and Fine Control of Blood Processinq via Density Centrifugation

In another aspect of the present invention, simultaneous measurements of (1) the position of phase boundaries between two or more optically differentiable blood components and (2) the composition of an extracted blood component are used in combination to establish, optimize and maintain blood processing conditions in a density centrifuge blood processing system. In an exemplary method, the position of phase boundaries between two or more optically differentiable blood components is directly measured using the present methods and used to selectively adjust and establish a set of initial operating conditions of the density centrifuge corresponding to the flow rate of the inlet pump, the flow rates of one or more extraction pumps, the rotational velocity of the centrifuge or any combination of these. These initial conditions provide a composition of the extracted component within a first range of the selected composition corresponding to a coarse optimization of the composition.

Upon achieving a composition within the first range of the selected composition, direct measurements of the composition of the extracted component(s) flowing through an extraction port are acquired and used to selectively adjust the operating conditions of the density centrifuge. Particularly, the system operating conditions are iteratively adjusted to provide a composition of the extracted component with in a second range of the selected composition corresponding to a fine optimization of the composition. In this embodiment of the present invention, the second range is narrower than the first range. Upon achieving a composition within the second range of the selected composition, direct measurements of the composition of the extracted component(s) flowing through an extraction port are continuously acquired and compared to the selected composition. If necessary, the operating conditions are readjusted to maintain the composition of the extracted component within the first range. If for some reason the composition of the extracted component exceeds both first and second ranges, the coarse optimization procedure is repeated and followed by the fine optimization procedure.

3. Bias Collection Methods of Collecting White Blood Cells

The optical monitoring and control methods of the present invention are capable of very accurately measuring the position of phase boundaries in an interface region and optically characterizing separated blood components exiting a separating chamber via one or more extraction ports. As most classes of cellular blood components, such as white blood cells, red blood cells and platelets, can be further differentiated on the basis of density into sub-classes, methods of the present invention are also be capable of biased collection of blood components, wherein a blood component substantially enriched with a selected component sub-class is extracted and collected. In one embodiment, sub-classes of a given separated blood component are differentiated on the basis of their spatial distribution within a given separation layer in a separation chamber. Alternatively, specific sub-classes of cellular material are be selectively photoluminescently labeled to allow for optical differentiation, for example by fluorescent or phosphorescent labeling.

For example, white blood cells comprise a plurality of optically differentiable sub-classes, such as erythrocytes, eosinophils, basophils, monocytes, lymphocytes and granulocytes. These sub-classes can be differentiated on the basis of the distribution of these cell types in a separated buffy coat layer in a rotating density centrifuge. The large signal-to-noise ratios and high sensitivities for measuring the position of phase boundaries provided by the present optical monitoring methods allow very accurate positioning of selected regions of a given separated layer, such as a top region corresponding to a higher density sub-component or a bottom region corresponding to a lower density sub-component, relative to an extraction port. This functional capability in turn allows extracted components corresponding to fluid components enriched in selected sub-classes of white blood cells types to be extracted and collected using the present methods. For example, positioning the extraction port proximate to the top of the buffy layer results in a white blood cell containing component enriched in lymphocytes, and positioning the extraction port proximate to the bottom of the buffy layer results in a white blood cell containing component enriched in granulocytes.

Using the present methods, for example, the position of phase boundaries between optically differentiable white blood cell sub-classes can be directly measured and controlled to within about 0.005 inch. Thus, the positions of phase boundary layers may be selectively adjusted to achieve a position relative to an extraction port proximate for providing an extract component enriched in a desired white blood cell sub-class. Further, in some embodiments, the composition of the extracted white blood cell component is directly monitored and optically classified with respect to the populations of various sub-classes. Iterative adjustment of centrifuge operating conditions on the basis of the optical characterization of the material passing through the extraction port also allows for extraction and collection of a white blood cell component enriched with a selected white blood cell sub-component.

This aspect of the present invention is also applicable to red blood cell containing components and platelet containing components. For example, red blood cells or platelets in separated blood components having atypical shapes and sizes which gives rise to different densities of these materials. Accordingly, selective positioning of an extraction port in a separated red blood cell containing layer or platelet containing layer allow for extraction and collection of fluid components enriched in red blood cells or platelets in separated blood components having atypical shapes and sizes. Further, this concept may also be used to collect plasma containing components enriched in plasma proteins having selected densities and/or molecular weights.

4. Methods of Monitoring the Extent of Hemolysis During Blood Processing.

Hemolysis occurs when red blood cells are damaged and release at least a portion of their hemoglobin. Hemolysis occurs when blood components are subjected to stresses induced by centrifugal blood processing, such as stresses induced by pumping blood components, flowing blood components into, through and out of a separation chamber and/or applying a centrifugal field. When hemolysis occurs during centrifugal blood processing at least a portion of the free hemoglobin migrates to the separated, lower density plasma blood component.

The present invention provides a means for directly monitoring and controlling the extent of hemolysis occurring during blood processing via density centrifuge techniques. In this method, the intensity of light transmitted by the separated plasma component is monitored as a function of time. If appreciable hemolysis occurs the free hemoglobin that migrates to the separated plasma component will absorb light, particularly in the 500 nm to 600 nm region of the electromagnetic spectrum. Measurements of the decrease in transmitted light intensity, particularly over the wavelength range of 500 nm to 600 nm, are used to quantify the extent of hemolysis that has occurred during blood processing. In some embodiments, use of incident light beams having a wavelength distribution with a peak between 500 nm to 600 nm, such as light provided by one or more green LEDs or using of selectively transmissive optical filters, enhances the sensitivity of these measurements. The present invention also includes methods of controlling the extent of hemolysis during blood processing whereby the inlet and extraction flow rates are lowered upon observation of an appreciable extent of hemolysis.

5. Enhanced Separation Protocols.

The optical monitoring and control methods and devices of the present invention are particularly well suited for blood processing methods wherein the rotational velocity of a density centrifuge is selectively adjusted as a function of time. Enhanced separation protocols include protocols that require a level of control that is not possible using algorithm-based systems because of the complex steps that require precise operating conditions and trigger points. An exemplary embodiment includes multiple protocol stages, each requiring different image analysis data and different areas of interest. For example, the methods of the present invention provide simultaneous measurements of the changes in the positions of phase boundaries between optically differentiable blood components caused by changes in the rotational velocity of the centrifuge and/or changes in the subject's incoming blood.

In an embodiment of the present invention, an enhanced separation protocol comprises three major stages. In the first stage, the blood processing system primes the optical cell and its associated secondary separation chamber with fluid.

In the protocol's second stage, the buildup stage, the monitoring and control system measures the position of the phase boundary between a red blood cell containing and a buffy coat layer and the position of a phase boundary between a buffy coat layer and plasma containing component. In addition, the monitoring and control system establishes a position of the buffy coat layer proximate to the orifice of an extraction port of an optical cell. After the monitoring and control system establishes the positions of the buffy coat layer proximate to the orifice of an extraction port, the platelets, plasma, white blood cells and few red blood cells contained in the buffy coat layer are all extracted and passed into a secondary chamber, such as an elutriation chamber, to further separate the extracted blood components and enhance the purity of the selected components. Unselected components are returned to the patient, while the selected components, such as white blood cells, are collected in the secondary chamber. During the second stage, the monitoring and control system simultaneously measures the cellular flux of cells entering the secondary chamber, the position of the phase boundary between the buffy coat layer and the plasma containing layer, the position of the phase boundary between the buffy coat layer and the red blood cell containing layer, and the position of the buffy coat layer relative to the extraction port in order to maintain optimal performance and separation conditions. As a result of the ability of the monitoring and control system to view and optically characterize a plurality of areas of interest, the system can collect two-dimensional images of scattered or transmitted light from the secondary chamber itself, to help determine if the chamber is full and ready to enter the system's third stage.

In the protocol's third stage, the monitoring and control system evaluates the status of the secondary chamber. If the secondary chamber is full of a selected material, the optical monitoring and control system triggers a flush out of the secondary chamber. To flush the secondary chamber, for example, the monitoring and control system can simultaneously adjust the position of the phase boundary between the buffy coat layer and the plasma containing layer to a position wherein the extraction port is exclusively in contact with the plasma layer. This procedure ensures that the flux of cellular matter through the extraction port is minimized. The monitoring and control system also lowers the rotational velocity of the centrifuge and changes a valve position to flush the selected cells from the secondary chamber into a collection container. The synchronization and timing control provided by the present methods allows the system to maintain precise interface positions required to achieve the flush step of the protocol. The monitoring and control system is also important for determining when the chamber is sufficiently flushed to return to another buildup stage by monitoring the intensities of transmitted and/or scattered light from the secondary processing chamber.

In one embodiment, the blood processing system repeats alternating buildup and flush stages to achieve a desired endpoint, at least partially based on the cellular flux measurements.

Enhanced blood separation protocols of the present invention may be used to separate and collect a range of cellular and noncellular blood components including but not limited to, white blood cells, platelets, and plasma proteins. In one embodiment, the present invention provides a method of processing blood comprising the steps of: (1) providing a two stage blood processing system comprising a density centrifuge blood processing system and an elutriation blood processing system; (2) flowing blood into the two stage blood processing system, wherein the blood is separated into a plurality of components in the density centrifuge blood processing system including at least one desired component and a plasma containing component; (3) filling the elutriation blood processing system with the desired component until the elutriation blood processing system is in a filled operating state; and (4) flushing the elutriation blood processing system when in the filled operating state by flowing the plasma containing component into the elutriation blood processing system, thereby processing the blood. Methods of this aspect of the present invention may further comprise the step of collecting at least a portion of the desired component in a container.

Methods of this aspect of the present invention may further comprise additional steps wherein device components and/or fluid components undergoing processing are optically characterized in real time using the present methods and devices. Optionally, the method of the present invention further comprises the step of optically measuring the composition of blood components passing through an extraction port of the density centrifuge blood processing system into the elutriation blood processing system. Optionally, the method of the present invention further comprises the step of optically measuring the position of the desired component in a separation chamber of the density centrifuge blood processing system and an extraction port of the density centrifuge blood processing system. Optionally, the method of the present invention further comprises the step of optically measuring the composition and/or position of fluid components in the elutriation blood processing system.

Methods of this aspect of the present invention further comprises additional steps wherein the operating state of the elutriation blood processing system is directly evaluated via optical measurements. Optionally, the method of the present invention further comprises the step of determining when the elutriation blood processing system is in the filled operating state by optically measuring the composition and/or position of fluid components in the elutriation blood processing system. Optionally, the method of the present invention further comprises the step of determining when the elutriation blood processing system is in the filled operating state by optically measuring the composition, flux or both of blood components passing through an extraction port of the density centrifuge blood processing system into the elutriation blood processing system.

We claim:

1. A system for processing blood by separating fluid components comprising:
a density centrifuge blood processing system having a separation chamber rotating about a central rotation axis—and operable to extract and collect a separated, selected component from the chamber;
a light source in optical communication with said density centrifuge blood processing system for providing an incident light beam for illuminating an observation region on said separation chamber of said density centrifuge blood processing system, thereby generating light transmitted, scattered or both from said observation region;
a light collection element in optical communication with said density centrifuge blood processing system for collecting at least a portion of said light transmitted, scattered or both from said observation region and for directing at least a portion of said light transmitted, scattered or both from said observation region onto a two-dimensional detector;
the two-dimensional detector position to receive and detect said light transmitted, scattered or both from said observation region provided by said light collection element, thereby measuring a two-dimensional distribution of intensities of said light transmitted, scattered or both from said observation region; said two-dimensional distribution of the intensities of said light transmitted, scattered or both from said observation region comprising an image of at least a portion of said density centrifuge blood processing system, said two-dimensional distribution of the intensities of said light transmitted, scattered or both providing a measurement of the positions of one or more phase boundary between optically differentiable blood components in said seperation chamber, and wherein said two-dimensional detector generates an output signal corresponding to said two-dimensional distribution of the intensities of said light transmitted, scattered or both from said observation; and
a centrifugation device controller in communication with said two-dimensional detector for receiving said output signal, wherein said controller controls the positions of one or more phase boundary by adjusting a flow-related operating parameter of the density centrifuge blood processing system.

2. The system of claim 1 wherein said two-dimensional distribution of the intensities of said light transmitted, scattered or both from said observation region comprises an image of said at least a portion of said separation chamber.

3. The system of claim 1 wherein said two-dimensional distribution of the intensities of said light transmitted, scattered or both from said observation region comprise an image of said at least a portion of an optical cell of said separation chamber.

4. The system of claim 3 wherein the image of a phase boundary between optically differentiable blood components provides said measurement of the position of the phase boundary.

5. The system of claim 1 wherein at least a portion of said light transmitted, scattered or both from said observation region is light transmitted through the separation chamber.

6. The system of claim 1 wherein at least a portion of said light transmitted, scattered or both from said observation region is light scattered by the separation chamber or materials therein.

7. The system of claim 1 wherein said centrifugation device controller and said two-dimensional detector provide feedback control of the positions of one or more phase boundary between optically differentiable blood components in said separation chamber.

8. The system of claim 1 wherein said centrifugation device controller is capable of adjusting a plurality of operating parameters of the density centrifuge blood processing system.

9. The system of claim 1 wherein said operating parameter is selected from the group consisting of:
- a flow rate of a fluid component out of the separation chamber;
- a flow rate of a fluid into the separation chamber; and
- the rate of rotation of the separation chamber about the central rotation axis.

10. The system of claim 1 wherein the light collection element and two-dimensional detector are stationary and provided in fixed positions relative to the density centrifuge blood processing system.

11. The system of claim 1 wherein the light collection element and two-dimensional detector are stationary and provided in fixed orientations relative to said density centrifuge blood processing system.

12. The system of claim 1 wherein at least a portion of said observation region is positioned such that a phase boundary between optically differentiable blood components in said separation chamber is viewable by the two-dimensional detector.

13. The system of claim 1 wherein said two-dimensional distribution of the intensities of said light transmitted, scattered or both from said observation region comprises an image of a phase boundary between optically differentiable blood components.

14. The system of claim 1 wherein at least a portion of said observation region is positioned such that a separated blood component in said separation chamber is viewable by two-dimensional detector.

15. The system of claim 1 wherein said two-dimensional distribution of the intensities of said light transmitted, scattered or both from said observation region comprises an image of a separated blood component in the separation chamber.

16. The system of claim 15 wherein the image of the separated blood component in the separation chamber provides a measurement of the composition of the separated blood component.

17. The system of claim 15 wherein said separated blood component is selected from the group consisting of:
- a white blood cell containing component;
- a platelet containing component;
- a plasma containing component; and
- a red blood cell containing component.

18. The system of claim 1 wherein at least a portion of the observation region is positioned such that an extraction port of the separation chamber is viewable by the two dimensional detector.

19. The system of claim 1 wherein said two-dimensional distribution of the intensities of said light transmitted, scattered or both from said observation region comprises an image of an extraction port of the separation chamber.

20. The system of claim 19 wherein the image of the extraction port of the separation chamber provides a measurement of the composition of cellular components in said extraction port.

21. The system of claim 20 wherein said cellular components are selected from the group consisting of:
- red blood cells;
- white blood cells; and
- platelets.

22. The system of claim 19 wherein the image of the extraction port of the separation chamber provides a measurement of the flux of cellular components through the extraction port.

23. The system of claim 1 wherein said two-dimensional distribution of the intensities of said light transmitted, scattered or both from said observation region comprises an image of at least one phase boundary between optically differentiable blood components in the separation chamber and at least one extraction port of the separation chamber.

24. The system of claim 23 wherein the image provides simultaneous measurements of said position of at least one phase boundary between optically differentiable blood components and the composition of blood components in the extraction port of the separation chamber.

25. The system of claim 1 wherein the observation region is positioned such that leakage of fluid in said separation chamber is viewable by the two-dimensional detector.

26. The system of claim 1 wherein said two-dimensional distribution of the intensities of said light transmitted, scattered or both from said observation region comprises an image of a sample identification marker or kit identification marker corresponding to a blood sample undergoing processing.

27. The system of claim 26 wherein said sample identification marker or kit identification marker comprises a bar code.

28. The system of claim 1 wherein the observation region is positioned such that improper alignment of said separation chamber is detectable by the two dimensional detector.

29. The system of claim 1 wherein the two-dimensional detector is selected from the group consisting of:
- a charge coupled device;
- a two-dimensional photodiode array;
- a two-dimensional photoconductive array;
- a two-dimensional pyroelectric array;
- a CCD camera; and
- a complementary metal oxide semiconductor detector.

30. The system of claim 1 wherein the two-dimensional detector is a monochrome CCD camera.

31. The system of claim 1 wherein the two-dimensional detector is a color CCD camera.

32. The system of claim 1 wherein the light collection element comprises a lens.

33. The system of claim 1 wherein the light collection element comprises a lens system.

34. The system of claim 33 wherein the lens system has a selectively adjustable focal length.

35. The system of claim 1 wherein the light collection element comprises a fixed focus lens system.

36. The system of claim 1 wherein the light collection element has a fixed field of view.

37. The system of claim 1, wherein the light collection element has a selectively adjustable field of view.

38. The system of claim 1 wherein said two-dimensional detector and light collection element are selectively positionable along a detector axis oriented orthogonal to the central rotation axis.

39. The system of claim 1 wherein the light source is selected from the group comprising:
- a xenon lamp;
- a light emitting diode; and
- an array of light emitting diodes;.

40. The system of claim 1 wherein the light source is selected from the group comprising:
- a white light emitting diode;
- blue light-emitting diode;

a red light-emitting diode; and
a green light-emitting diode.

41. The system of claim 1 wherein the light source comprises a parabolic reflector element.

42. The system of claim 1 further comprising an additional light source, wherein said light source illuminates a first side of said separation chamber and said additional light source illuminates a second side of said separation chamber, and wherein said first and second sides are different sides.

43. The system of claim 42 wherein the additional light source is selected from the group comprising:
a xenon lamp;
a light emitting diode; and
an array of light emitting diodes.

44. The system of claim 1 wherein the light source provides an incident light beam comprising visible light.

45. The system of claim 1 wherein the light source provides an incident light beam comprising infrared light.

46. The system of claim 1 wherein the light source provides an incident light beam comprising ultraviolet light.

47. The system of claim 1 wherein the light source provides continuous illumination of the observation region on the separation chamber.

48. The system of claim 1 wherein the light source is capable of being switched on and off in a manner providing pulsed illumination of the observation region on the separation chamber.

49. The system of claim 1 wherein said separation chamber comprises an optical cell.

50. The system of claim 49 wherein said optical cell comprises:
an extraction chamber having a first external optical surface and a second external optical surface, wherein said first and second external optical surfaces of said extraction chamber are opposing planar surfaces; and
an extraction port having a first external optical surface and a second external optical surface, wherein said first and second external optical surfaces of said extraction chamber are opposing planar surfaces;
wherein said first optical surface of said extraction chamber and said first optical surface of said extraction port are both in the depth of field of the light collection element.

51. The system of claim 50 wherein first optical surface of said extraction chamber and said first optical surface of said extraction port are both substantially in the same plane.

52. The system of claim 1 further comprising a calibration marker, wherein said calibration marker is in said observation region.

53. The system of claim 52 wherein the calibration marker is in the depth of field of the light collection element.

54. The system of claim 52 wherein said two-dimensional distribution of the intensities of said light transmitted, scattered or both from said observation region comprises an image of said calibration marker.

55. The system of claim 1 further comprising an additional light collection element and an additional two-dimensional detector, wherein light transmitted, scattered or both from an additional observation region is collected by the additional light collection element and detected by the additional two-dimensional detector.

56. The system of claim 55 wherein said additional two-dimensional detector measures a two-dimensional distribution of the intensities of said light transmitted, scattered or both from said additional observation region.

57. The system of claim 1 wherein said fluid components are blood components.

58. The system of claim 1, wherein said centrifugation device controller determines the position of phase boundaries between said optically differentiable blood components.

59. The system of claim 1, wherein said centrifugation device controller determines one or more of the following:
a flux of cellular material out of the separation chamber;
a flux of noncellular material out of the separation chamber;
a composition of an extracted blood component;
a hematocrit of an extracted blood component; and
an extent of hemolysis in said blood.

60. A method of monitoring a density centrifuge blood processing system comprising the steps of:
providing said density centrifuge blood processing system having a separation chamber rotating about a central rotation axis and operable to extract and collect a separated, selected component from the chamber;
illuminating an observation region on a density centrifuge blood processing system with an incident light beam provided by a light source, thereby generating light transmitted, scattered or both from said observation region;
collecting at least a portion of light transmitted, scattered or both from said observation region and directing said light transmitted, scattered or both from said observation region onto a two-dimensional detector;
measuring two-dimensional distributions of intensities of said light transmitted, scattered or both from said observation region; said two-dimensional distributions of the intensities of said light transmitted, scattered or both from said observation region comprising images of at least a portion of said density centrifuge blood processing system, said two-dimensional distributions of the intensities of said light transmitted, scattered or both providing measurements of the positions of one or more phase boundary between optically differentiable blood components in said separation chamber;
generating output signals corresponding to said two-dimensional distributions of the intensities of said light transmitted, scattered or both from said observation region; and
providing a centrifugation device controller for receiving said output signals, wherein said controller provides feedback control of said positions of said one or more phase boundary based on said output signals, wherein said controller controls the positions of said one or more phase boundary by adjusting a flow-related operating parameter of the density centrifuge blood processing system.

61. The method of claim 60 wherein said two-dimensional distribution of the intensities of said light transmitted, scattered or both from said observation region comprises an image of said at least a portion of said separation chamber.

62. The method of claim 60 wherein said two-dimensional distribution of the intensities of said light transmitted, scattered or both from said observation region comprises an image of said at least a portion of an optical cell of said separation chamber.

63. The method of claim 62 wherein said phase boundary between optically differentiable components in the separation chamber is viewable in said image.

64. The method of claim 63 further comprising measuring the position of said phase boundary.

65. The method of claim 62 wherein an extraction port of the separation chamber is viewable in said image.

66. The method of claim 65 further comprising determining the average intensity of light transmitted through a selected portion of said extraction port.

67. The method of claim 66 further comprising measuring a composition of a component passing through said extraction port.

68. The method of claim 60 further comprising the step of providing a calibration marker in the depth of field of the light collection element.

69. The method of claim 60 wherein said step of illuminating the observation region comprises providing a pulsed incident light beam.

70. The method of claim 69 further comprising the step of selecting the rotational position of the separation chamber corresponding to the two-dimensional distribution of the intensities of said light transmitted, scattered or both from said observation region by selecting the timing and duration of the pulsed incident light beam.

71. The method of claim 70 further comprising the step of selecting different rotational positions of the separation chamber corresponding to the two-dimensional distribution of the intensities of said light transmitted, scattered or both from said observation region for different rotations of said separation chamber.

72. The method of claim 60 wherein said step of illuminating the observation region comprises providing a plurality of pulsed incident light beams.

73. A method of controlling a blood centrifuge blood processing system for separating fluid components comprising the steps of:
providing said density centrifuge blood processing system having a separation chamber rotating about a central rotation axis and operable to extract and collect a separated, selected component from the chamber;
illuminating an observation region on a density centrifuge blood processing system with an incident light beam provided by a light source, thereby generating light transmitted, scattered or both from said observation region;
collecting at least a portion of light transmitted, scattered or both from said observation region and directing said light transmitted, scattered or both from said observation region onto a two-dimensional detector;
measunng a two-dimensional distribution of intensities of said light transmitted, scattered or both from said observation region; said two-dimensional distributions of the intensities of said light transmitted, scattered or both from said observation region comprising an image of at least a portion of said density centrifuge blood processing system, wherein one or more phase boundary between optically differentiable blood components in said separation chamber is viewable in said image;
measuring the positions of said one or more phase boundary between optically differentiable blood components in said separation chamber; and
controlling the positions of said one or more phase boundary by selectively adjusting a flow-related operating parameter of said density centrifuge blood processing system based on said two-dimensional distribution of the intensities of said light transmitted, scattered or both from said observation region, wherein said flow-related operating parameter is selected from the group consisting of: a flow rate of a fluid component out of the separation chamber; a flow rate of a fluid into the separation chamber; and the rate of rotation of the separation chamber about the central rotation axis.

74. The method of claim 73 wherein said two-dimensional distribution of the intensities of said light transmitted, scattered or both from said observation region comprises an image of a phase boundary between optically differentiable components in said separation chamber.

75. The method of claim 74 further comprising the step of measuring the position of the phase boundary between optically differentiable components in said separation chamber.

76. The method of claim 75 wherein the operating parameter of said density centrifuge blood processing system is selectively adjusted on the basis of the position of the phase boundary between optically differentiable components in said separation chamber.

77. The method of claim 73 wherein said two-dimensional distribution of the intensities of said light transmitted, scattered or both from said observation region comprises an image of an extraction port of said separation chamber.

78. The method of claim 77 further comprising the step of measuring the composition of fluid components passing through said extraction port of said separation chamber.

79. The method of claim 78 wherein said operating parameter of said density centrifuge blood processing system is selectively adjusted on the basis of the composition of fluid components passing through said extraction port of said separation chamber.

80. The method of claim 78 wherein said operating parameter of said density centrifuge blood processing system is adjusted such that the composition of fluid components passing through said extraction port of said separation chamber is in a predefined range of compositions.

81. The method of claim 73 wherein said two-dimensional distribution of the intensities of said light transmitted, scattered or both from said observation region comprises an image of an extraction port of said separation chamber and said phase boundary between optically differentiable components in said separation chamber.

82. The method of claim 81 further comprising the step of measuring the composition of fluid components passing through said extraction port of said separation chamber and measuring the position of the phase boundary between optically differentiable components in said separation chamber.

83. The method of claim 81 wherein said operating parameter of said density centrifuge blood processing system is selectively adjusted on the basis of the composition of fluid components passing through said extraction port of said separation chamber and the position of the phase boundary between optically differentiable components in said separation chamber.

84. The method of claim 73 further comprising the step of providing a calibration marker in the depth of field of the light collection element.

85. The method of claim 73 further comprising the step of selectively adjusting a plurality of operating parameters of said density centrifuge blood processing system.

86. The method of claim 73 wherein said fluid components are blood components.

* * * * *

UNITED STATES PATENT AND TRADEMARK OFFICE
CERTIFICATE OF CORRECTION

PATENT NO. : 7,422,693 B2
APPLICATION NO. : 10/884877
DATED : September 9, 2008
INVENTOR(S) : Carter et al.

It is certified that error appears in the above-identified patent and that said Letters Patent is hereby corrected as shown below:

On the title page, item (73), replace "Caridianbct, Inc." with --CaridianBCT, Inc.--.

In claim 1, column 72, line 35, please insert --region-- after "from said observation".

In claim 1, column 72, line 38, please insert --said-- after "the positions of".

In claim 73, column 77, line 28, please delete "a blood centrifuge" and replace with --a density centrifuge--.

In claim 73, column 77, line 44, please delete "measunng" and replace with --measuring--.

In claim 73, column 77, line 46, please delete "distributions" and replace with --distribution--.

Signed and Sealed this

Twenty-seventh Day of October, 2009

David J. Kappos
*Director of the United States Patent and Trademark Office*